United States Patent [19]
Allen et al.

[11] Patent Number: 5,260,285
[45] Date of Patent: Nov. 9, 1993

[54] SUBSTITUTED IMIDAZOPYRIDAZINES AS ANGIOTENSIN II ANTAGONISTS

[75] Inventors: Eric E. Allen, Somerset; William J. Greenlee, Teaneck; Prasun K. Chakravarty, Edison; Malcolm MacCoss, Freehold; Arthur A. Patchett; Thomas F. Walsh, both of Westfield, all of N.J.

[73] Assignee: Merck & Co., Inc., Rahway, N.J.

[21] Appl. No.: 794,534

[22] Filed: Nov. 25, 1991

Related U.S. Application Data

[63] Continuation-in-part of Ser. No. 623,880, Dec. 7, 1990, abandoned.

[51] Int. Cl.$^5$ .................. A61K 31/675; A61K 31/50; A61K 31/505; C07D 487/04
[52] U.S. Cl. ..................... 514/81; 514/222.5; 514/228.5; 514/234.2; 514/245; 514/248; 514/258; 544/2; 544/61; 544/117; 544/180; 544/182; 544/232; 544/236; 544/281; 548/250; 548/253; 552/4; 558/411; 558/426; 558/434; 558/440; 556/95; 564/90; 560/102; 568/928
[58] Field of Search .................. 544/2, 117, 180, 182, 544/232, 236, 61; 514/81, 222.5, 234.2, 245, 248, 228.5

[56] References Cited

U.S. PATENT DOCUMENTS

| | | | |
|---|---|---|---|
| 4,880,804 | 11/1989 | Carini et al. | 514/234.5 |
| 5,102,880 | 4/1992 | Chakravarty et al. | 514/212 |
| 5,166,206 | 11/1992 | Allen et al. | 544/299 |

FOREIGN PATENT DOCUMENTS

| | | |
|---|---|---|
| 245637 | of 0000 | European Pat. Off. |
| 399731 | of 0000 | European Pat. Off. |
| 183848 | 6/1986 | European Pat. Off. |
| 400835 | 12/1990 | European Pat. Off. |
| 1135893 | 12/1968 | United Kingdom |
| 91/15209 | of 0000 | World Int. Prop. O. |

OTHER PUBLICATIONS

Chiu et al., Eur. J. Pharm. Exp. Ther. 157, pp. 13-21 (1988).
Wong et al., J. Pharm. Exp. Ther. 247, pp. 1-7 (1988).

*Primary Examiner*—Emily Bernhardt
*Attorney, Agent, or Firm*—Robert J. North; William H. Nicholson; Joseph F. DiPrima

[57] ABSTRACT

Novel substituted imidazopyridazines of formula (I) which are useful as angiotensin II antagonists, are disclosed.

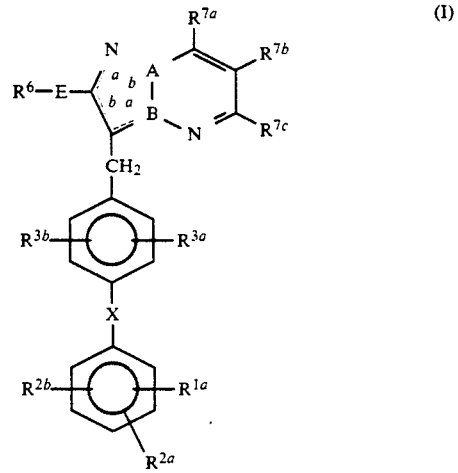

11 Claims, No Drawings

SUBSTITUTED IMIDAZOPYRIDAZINES AS ANGIOTENSIN II ANTAGONISTS

INTRODUCTION OF THE INVENTION

The present application is a continuation in part of copending application Ser. No. 623,880 filed on Dec. 7, 1990 (now abandoned).

This invention relates to novel substituted pyrazolopyrimidine and imidazopyridazine compounds and derivatives thereof which are useful as angiotensin II antagonists in the treatment of elevated blood pressure, in the treatment of congestive heart failure, and in the treatment of elevated intraocular pressure. Thus, the substituted pyrazolopyrimidine and imidazopyridazine compounds of the invention are useful as antihypertensives.

BACKGROUND OF THE INVENTION

Renin-angiotensin system (RAS) plays a central role in the regulation of normal blood pressure and seems to be critically involved in hypertension development and maintenance as well as congestive heart failure. angiotensin II (A II), an octapeptide hormone is produced mainly in the blood during the cleavage of angiotensin I by angiotensin converting enzyme (ACE) localized on the endothelium of blood vessels of lung, kidney, and many other organs, and is the end product of the RAS. A II is a powerful arterial vasoconstricter that exerts its action by interacting with specific receptors present on cell membranes. One of the possible modes of controlling the RAS is angiotensin II receptor antagonism. Several peptide analogs of A II are known to inhibit the effect of this hormone by competitively blocking the receptors, but their experimental and clinical applications have been limited by the partial agonist activity and lack of oral absorption [M. Antonaccio. *Clin. Exp. Hypertens.* A4, 27–46 (1982); D. H. P. Streeten and G. H. Anderson, Jr.—*Handbook of Hypertension, Clinical Pharmacology of Antihypertensive Drugs*, ed. A. E. Doyle, Vol. 5, pp. 246–271, Elsevier Science Publisher, Amsterdam, The Netherlands, 1984].

Recently, several non-peptide compounds have been described as A II antagonists. Illustrative of such compounds are those disclosed in U.S. Pat. Nos. 4,207,324; 4,340,598; 4,576,958; 4,582,847; and 4,880,804; in European Patent Applications 028,834; 245,637; 253,310; 291,969; 323,841; 324,377 and 380,959; and in articles by A. T. Chiu, et al. [*Eur. J. Pharm. Exp. Therap*, 157, 13–21 (1988)] and by P. C. Wong, et al. [*J. Pharm. Exp. Therap*, 247, 1–7 (1988): *Hypertension*, 13, 489–497 (1988)]. All of the U.S. Patents, European Patent Applications 028,834 and 253,310 and the two articles disclose substituted imidazole compounds which are generally bonded through a lower alkyl bridge to a substituted phenyl. European Patent Application 245,637 discloses derivatives of 4,5,6,7-tetrahydro-2H-imidazo[4,5-c]-pyridine-6-carboxylic acid and analogs thereof as antihypertensive agents.

DETAILED DESCRIPTION OF THE INVENTION

This invention relates to novel substituted pyrazolopyrimidine and imidazopyridazine compounds and derivatives thereof which are useful as angiotensin II antagonists and as antihypertensives, in the treatment of congestive heart failure, and in the treatment of elevated intraocular pressure. The compounds of this invention have the general formula (I):

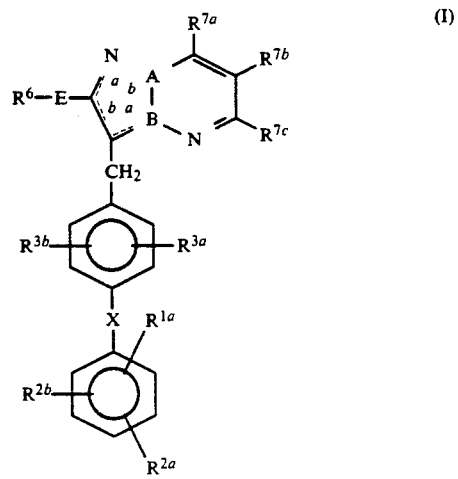

wherein:

A is N or C,

B is N or C, provided that one and only one of A or B is N;

a and b each represent a set of double bonds so that when A is N, a is a set of double bonds and when B is N, b is a set of double bonds.

Thus, the compounds of formula (I) can also be expressed as compounds having the formulae (Ia) and (Ib):

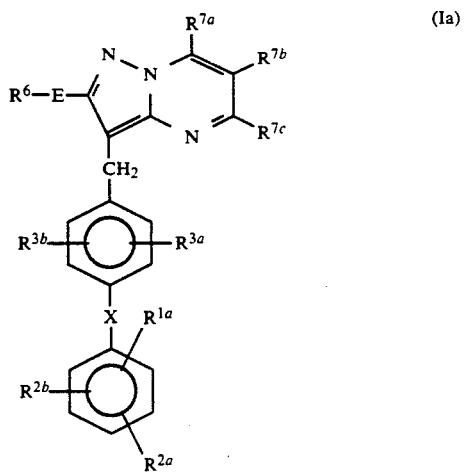

-continued (Ib)

[Structure showing pyridazine ring with substituents R⁶-E, R⁷ᵃ, R⁷ᵇ, R⁷ᶜ connected via CH₂ to a phenyl ring bearing R³ᵃ, R³ᵇ, linked by X to another phenyl ring bearing R¹ᵃ, R²ᵃ, R²ᵇ]

wherein:
$R^{1a}$ is:
- (a) —H,
- (b) —CO$_2$R$^{29}$,
- (c) —SO$_3$R$^5$,
- (d) —NHSO$_2$CF$_3$,
- (e) —PO(OR$^5$)$_2$,
- (f) —SO$_2$—NH—R$^8$,
- (g) —CONHOR$^5$,
- (h)

$$-\underset{R^8}{\overset{OH}{\underset{|}{C}}}-\overset{O}{\underset{OR^5}{\overset{\|}{P}}}-OR^5,$$

- (i) —CN,
- (j) —PO(OR$^5$)R$^4$,
- (k)

[5-methyl-1-R¹⁰-tetrazole] or [5-methyl-2-R¹⁰-tetrazole]

(l)

—CH$_2$-[1-R¹⁰-tetrazol-5-yl] or —CH$_2$-[2-R¹⁰-tetrazol-5-yl]

(m)

—CONH-[1-R¹⁰-tetrazol-5-yl] or —CONH-[2-R¹⁰-tetrazol-5-yl]

(n) —CONHNHSO$_2$CF$_3$,
(o)

[3-methyl-5-CF₃-1H-1,2,4-triazole, NH] (p)

[3-methyl-5-R¹¹-pyrazole, NH] (q)

[N-methyl-1,2,4-oxadiazolidine-3,5-dione, NH] (r)

[thiazolidinedione ring] (s)

[4-hydroxy-5-methyl-isothiazol-3(2H)-one 1,1-dioxide]

(t) CONHSO$_2$R$^{20}$,
(u) SO$_2$NHCOR$^{20}$,
(v) —SO$_2$NH-heteroaryl, wherein heteroaryl is an unsubstituted, monosubstituted or disubstituted five- or six-membered aromatic ring which can optionally contain 1 to 3 heteroatoms selected from the group consisting of O, N or S and wherein the substituents are members selected from the group consisting of: —OH, —SH, —(C$_1$-C$_4$)-alkyl, —(C$_1$-C$_4$)-alkoxy, Cl, Br, F, I, —NO$_2$, —CO$_2$H, —CO$_2$—(C$_1$-C$_4$)-alkyl, —NH$_2$, —NH[(C$_1$-C$_4$)-alkyl] and —N[(C$_1$-C$_4$)-alkyl]$_2$;
(w) —CH$_2$SO$_2$NH-heteroaryl,
(x) —CH$_2$SO$_2$NHCO—R$^{20}$,
(y) —CH$_2$CONH—SO$_2$R$^{20}$,
(z) —NHSO$_2$NHCO—R$^{20}$,
(aa) —NHCONHSO$_2$—R$^{20}$,
(ab) —CONHSO$_2$NR$^4$R$^{20}$,
(ac) —SO$_2$NHCONR$^4$R$^{20}$,
(ad) —SO$_2$N(R$^{22}$)OR$^{22}$,
(ae) —SO$_2$NHSO$_2$R$^{21}$,
(af) —SO$_2$NHPO(R$^{24}$)$_2$,
(ag) —CONHPO(R$^{24}$)$_2$,
(ah) —SO$_2$NHCN, (ai) —SO$_2$NHCOR$^{21}$,
(aj) —SO$_2$NHSO$_2$NR$^{26}$R$^{27}$
(ak) —SO$_2$NHSO$_2$N[CH$_2$CH$_2$]$_2$Y, wherein Y is O or S;
(al) —NHSO$_2$NHSO$_2$R$^{21}$,
(am) —NHSO$_2$NHPO(R$^{24}$)$_2$,
(an) —NHSO$_2$R$^{21}$,
(ao) —NR$^{26}$COCO$_2$H,
(ap) —SO$_2$NHCO$_2$R$^{20}$,
(aq)

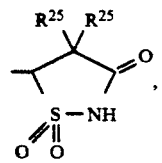

(ar)

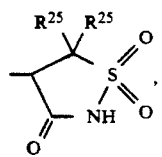

(as)

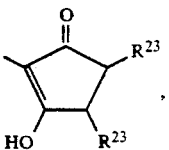

(at)

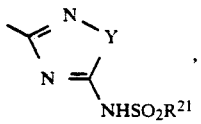

(au)

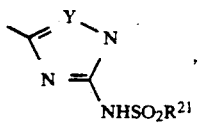

(av)

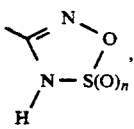

(aw)

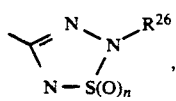

(ax)

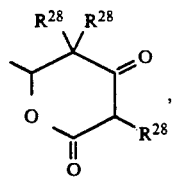

(ay)

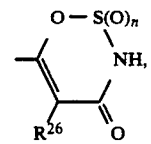

or (az)

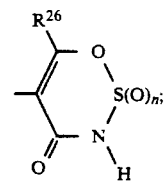

R$^1$ is:
(a) —CO$_2$H,
(b) —CO$_2$R$^{29}$,
(c) —CONH—SO$_2$—R$^{20}$,
(d) —CONHSO$_2$NR$^8$R$^8$,
(e) —CONHOR$^5$,
(f)

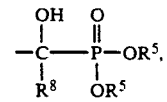

(g) —CN,
(h) CONHNHSO$_2$CF$_3$,
(i) CH$_2$SO$_2$NH-heteroaryl,
(j) CH$_2$SO$_2$NHCOR$^{20}$, or
(k) CH$_2$CONHSO$_2$R$^{20}$;
(l)

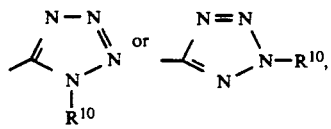

(m)

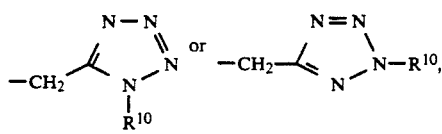

or
(n)

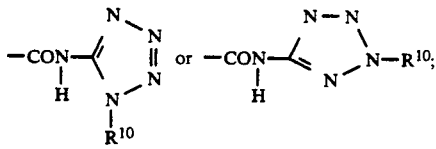

$R^{2a}$ and $R^{2b}$ are each independently
(a) H,
(b) Br, Cl, F, I,
(c) $NO_2$,
(d) $NH_2$,
(e) $NH[(C_1-C_4)\text{-alkyl}]$,
(f) $N[(C_1-C_4)\text{-alkyl}]_2$
(g) $SO_2NHR^8$,
(h) $CF_3$,
(i) $(C_1-C_6)$-alkyl, $(C_2-C_6)$-alkenyl, or $(C_2-C_6)$-alkynyl, or
(j) $(C_1-C_4)$-alkoxy;

$R^{3a}$ is
(a) H,
(b) Cl, Br, I, or F,
(c) $(C_1-C_6)$-alkyl,
(d) $(C_1-C_6)$-alkoxy,
(e) $(C_1-C_6)$-alkoxy-$(C_1-C_4)$-alkyl;

$R^{3b}$ is
(a) H,
(b) Cl, Br, I, or F,
(c) $NO_2$,
(d) $(C_1-C_6)$-alkyl, $(C_2-C_6)$-alkenyl, or $(C_2-C_6)$-alkynyl,
(e) $(C_1-C_6)$-alkanoyloxy,
(f) $(C_3-C_6)$-cycloalkyl,
(g) $(C_1-C_6)$-alkoxy,
(h) $-NHSO_2R^4$,
(i) hydroxy-$(C_1-C_4)$-alkyl,
(j) furyl,
(k) $(C_1-C_4)$-alkylthio,
(l) $(C_1-C_4)$-alkylsulfinyl,
(m) $(C_1-C_4)$-alkylsulfonyl,
(n) $NH_2$,
(o) $NH[(C_1-C_4)\text{-alkyl}]$,
(p) $N[(C_1-C_4)\text{-alkyl}]_2$,
(q) $(C_1-C_4)$-perfluoroalkyl,
(r) $-SO_2-NHR^8$,
(s) aryl, wherein aryl is phenyl unsubstituted or substituted with one or two substituents selected from the group consisting of Cl, Br, I, F or $(C_1-C_4)$-alkyl, which is substituted or unsubstituted with members selected from the group consisting of: $N(R^4)_2$, $CO_2R^4$, OH, $N(R^4)CO_2R^{20}$, $S(O)_nR^{20}$, wherein n is 0 to 2; $(C_1-C_4)$-alkoxy, $NO_2$, $CF_3$, $(C_1-C_4)$-alkylthio, OH, $NH_2$, $-NH[(C_1-C_4)\text{-alkyl}]$, $-N[(C_1-C_4)\text{-alkyl}]_2$, $-CO_2H$, $-CO_2-(C_1-C_4)$-alkyl, $N(R^4)CO_2R^{20}$, or

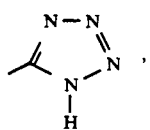

or
(t) aryl-$(C_1-C_4)$-alkyl;

$R^4$ is H, $(C_1-C_6)$-alkyl unsubstituted or substituted with aryl;
$R^{4a}$ is $(C_1-C_6)$-alkyl, aryl or aryl—$CH_2$—;
$R^5$ is H, or $-CHR^4OCOR^{4a}$;
E is a single bond, $-NR^{12}(CH_2)_s-$, $-S(O)_n(CH_2)_s-$ wherein n is 0 to 2 and s is 0 to 5, $-CH(OH)-$, $-O-$, CO—;
$R^6$ is
(a) aryl,
(b) $(C_1-C_6)$-alkyl, $(C_2-C_5)$-alkenyl or $(C_2-C_5)$-alkynyl each of which is unsubstituted or substituted with a substituent selected from the group consisting of: aryl, $C_3$-$C_7$-cycloalkyl, Cl, Br, I, F, $-OH$, $CF_3$, $-CF_2CF_3$, $CCl_3$, $-NH_2$, $-NH[(C_1-C_4)\text{-alkyl}]$, $-N[(C_1-C_4)\text{-alkyl}]_2$, $-NH-SO_2R^4$, $-COOR^4$, $-SO_2NHR^8$, $(C_1-C_4)$-alkoxy, $(C_1-C_4)$-alkyl-S;
(c) an unsubstituted, monosubstituted or disubstituted heteroaromatic 5 or 6 membered cyclic ring which can contain one or two members selected from the group consisting of: N, O, S, and wherein the substituents are members selected from the group consisting of: $-OH$, $-SH$, $(C_1-C_4)$-alkyl, $(C_1-C_4)$-alkyloxy $-CF_3$, Cl, Br, I, F, $NO_2$, $-CO_2H$, $-CO_2-(C_1-C_4)$-alkyl, $-NH_2-NH[(C_1-C_4)\text{-alkyl}]$, $-N[(C_1-C_4)\text{-alkyl}]_2$;
(d) $(C_3-C_7)$-cycloalkyl;

$R^{7a}$, $R^{7b}$ and $R^{7c}$ are independently
(a) H,
(b) aryl-$(C_1-C_4)$-alkyl-,
(c) heteroaryl-$(C_1-C_4)$-alkyl-,
(d) $(C_1-C_4)$-alkyl, unsubstituted or substituted with a substituent selected from the group consisting of: $-OH$, $-NH_2$, guanidino, $(C_1-C_4)$-alkoxy, $-S(O)_nR^{20}$, $(C_1-C_4)$-alkylamino, $(C_1-C_4)$-dialkylamino, $-COOR^4$, $-CON(R^4)R^{20}$, $-OCON(R^4)R^{20}$, $-O-COR^4$, $(C_3-C_5)$-cycloalkyl, $-N(R^4)CON(R^4)R^{20}$, $-N(R^4)COOR^{20}$, $-CONHSO_2R^{20}$, $-N(R^4)SO_2R^{20}$;
(e) $(C_2-C_4)$-alkenyl,
(f) $-CO$-aryl,
(g) $(C_3-C_7)$-cycloalkyl,
(h) Cl, Br, I, or, F
(i) $-OH$,
(j) $-OR^{20}$,
(k) $(C_1-C_4)$-perfluoroalkyl,
(l) $-SH$,
(m) $-S(O)_nR^{20}$,
(n) $-CHO$,
(o) $-CO_2R^4$,
(p) $-SO_3H$,
(q) $-N(R^4)_2$,
(r) $-N(R^4)CO_2R^{20}$,
(s) $-N(R^4)CONR^4R^{20}$,
(t) $-N(R^4)CSNR^4R^{20}$,
(u) $-N(R^4)CON[CH_2CH_2]_2G$, wherein G is $-CH_2-$, $-O-$ $-N(R^4)-$, or $-N(COR^{20})-$,
(v) $-SO_2NR^8R^9$,
(w) $-CH_2OCOR^4$,
(x) $-N(R^4)-SO_2-(C_1-C_4)$-alkyl,
(y) 5 or 6 membered saturated heterocycle containing one nitrogen atom and optionally containing one other heteroatom selected from N, O or S, such as pyrrolidine, morpholine, or piperazine,
(z) aryl,
(aa) heteroaryl,
(ab)

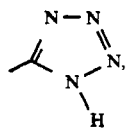

(ac) —NHSO$_2$—(C$_1$-C$_4$)-perfluoroalkyl,
(ad) —CONHSO$_2$R$^{20}$,
(ae) —SO$_2$NHCOR$^{20}$,
(af) —SO$_2$NH-heteroaryl,
(ag) —S(O)$_n$-aryl,
(ah) —S(O)$_n$CH$_2$-aryl,
(ai) —CON(R$^4$)$_2$,
(aj) —N[CH$_2$CH$_2$]$_2$G, or
(ak) CON[CH$_2$CH$_2$]$_2$G;

R$^8$ is H, (C$_1$-C$_5$)-alkyl, phenyl or benzyl;
R$^9$ is H, (C$_1$-C$_4$)-alkyl;
R$^{10}$ is H, (C$_1$-C$_6$)-alkyl, (C$_2$-C$_4$)-alkenyl, C$_1$-C$_4$-alkoxy alkyl, or —CH$_2$-C$_6$H$_4$R$^{19}$;
R$^{11}$ is —CN, —NO$_2$ or —CO$_2$R$^4$;
R$^{12}$ is H, (C$_1$-C$_4$)-acyl, (C$_1$-C$_6$)-alkyl, allyl, (C$_3$-C$_6$)-cycloalkyl, phenyl or benzyl;
R$^{13}$ is H, (C$_1$-C$_8$)-alkyl, (C$_1$-C$_8$)-perfluoroalkyl, (C$_3$-C$_6$)-cycloalkyl, phenyl or benzyl;
R$^{14}$ is H, (C$_1$-C$_6$)-alkyl;
R$^{15}$ is H, (C$_1$-C$_6$)-alkyl, (C$_3$-C$_6$)-cycloalkyl, phenyl or benzyl;
R$^{16}$ is —NR$^8$R$^9$, —OR$^9$, —NHCONH$_2$, —NHCSNH$_2$,

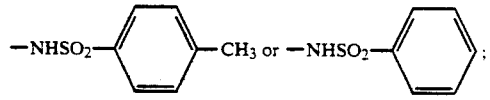

R$^{17}$ and R$^{18}$ are independently (C$_1$-C$_4$)-alkyl or taken together are —(CH$_2$)$_q$-, wherein q is 2 or 3;
R$^{19}$ is H, —NO$_2$, —NH$_2$, —OH or —OCH$_3$;
R$^{20}$ is
  (a) aryl,
  (b) heteroaryl,
  (c) (C$_1$-C$_8$)-alkyl, wherein the alkyl group is unsubstituted or substituted with a substituent selected from the group consisting of: aryl, heteroaryl, —OH, —SH, (C$_3$-C$_5$)-cycloalkyl, —O(C$_1$-C$_4$)-alkyl, —S—(C$_1$-C$_4$)-alkyl, —CF$_3$, Cl, Br, F, I, —NO$_2$, —CO$_2$H, —CO$_2$R$^4$, NHCOR$^{4a}$, —NH$_2$, —NH[(C$_1$-C$_4$)-alkyl], —N[(C$_1$-C$_4$)-alkyl]$_2$, PO$_3$H$_2$, PO(OH)(aryl), PO(OH)[(C$_1$-C$_4$)-alkyl];
  (d) C$_3$-C$_5$-cycloalkyl, unsubstituted or substituted with one or two substitutents selected from the group consisting of: (C$_1$-C$_6$)-alkyl, —OH, —NH$_2$, —NH[(C$_1$-C$_4$)-alkyl], —N[(C$_1$-C$_4$)-alkyl]$_2$, NHCOR$^{4a}$, —CO$_2$H, —CO$_2$R$^4$, Cl, Br, F, I, —CF$_3$, or
  (e) (C$_1$-C$_4$)-perfluoroalkyl;

X is
  (a) a carbon-carbon single bond,
  (b) —CO—,
  (c) —O—,
  (d) —S—,
  (e)

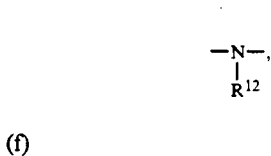

(f)

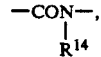

(g)

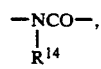

(h) —OCH$_2$—,
(i) —CH$_2$O—
(j) —SCH$_2$—,
(k) —CH$_2$S—,
(l) —NHC(R$^8$)(R$^9$),
(m) —NR$^8$SO$_2$—,
(n) —SO$_2$NR$^8$—,
(o) —C(R$^8$)(R$^9$)NH—,
(p) —CH=CH—,
(q) —CF=CF—,
(r) —CH=CF—,
(s) —CF=CH—,
(t) —CH$_2$CH$_2$—,
(u) —CF$_2$CF$_2$—,
(v)

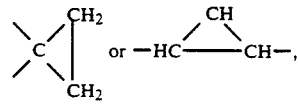

(w)

(x)

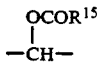

(y)

or
(z)

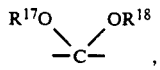

when R$^{1a}$ is H, then X can be:
(aa)

(ab)

$$-O-\overset{R^1}{\underset{|}{CH}},$$

(ac)

$$-\overset{R^1}{\underset{|}{CH}}-O-,$$

(ad)

$$-\overset{R^{15}R^1}{\underset{|}{N}}-CH-,$$

or $$-\overset{R^1}{\underset{|}{CH}}-\overset{R^{15}}{\underset{|}{N}};$$

$R^{21}$ is
 (a) aryl,
 (b) heteroaryl,
 (c) $(C_3-C_7)$-cycloalkyl,
 (d) $(C_1-C_6)$-alkyl or a substituted $(C_1-C_6)$-alkyl with one or two substituents selected from the group consisting of aryl, heteroaryl, —OH, —SH, $(C_1-C_4)$-alkyl, $(C_3-C_7)$-cycloalkyl, —O$(C_1-C_4)$-alkyl, —S$(C_1-C_4)$-alkyl, —CF$_3$, Cl, Br, F, I, —NO$_2$, —CO$_2$H, —CO$_2$—$(C_1-C_4)$-alkyl, —N[$(C_1-C_4)$-alkyl]$_2$, —PO$_3$H$_2$, —PO(OH)(O—$(C_1-C_4)$-alkyl, PO(OR$^{26}$)(R$^{27}$), morpholinyl or $(C_1-C_4)$-alkylpiperazinyl, or
 (e) —$(C_1-C_4)$-perfluoroalkyl; p1 $R^{22}$ is
 (a) hydrogen,
 (b) aryl,
 (c) heteroaryl,
 (d) $(C_3-C_7)$-cycloalkyl,
 (e) $(C_1-C_6)$-alkyl or a substituted $(C_1-C_6)$-alkyl with a substituent selected from the group consisting of aryl, heteroaryl, —OH, —SH, $(C_1-C_4)$-alkyl, —O$(C_1-C_4)$-alkyl, —S$(C_1-C_4)$-alkyl, —CF$_3$, Cl, Br, F, I —NO$_2$, —CO$_2$H, —CO$_2$—$(C_1-C_4)$-alkyl, —NH$_2$, —NH[$(C_1-C_4)$-alkyl], —N[$(C_1-C_4)$-alkyl]$_2$, —PO$_3$H$_2$, —PO(OH)-(O—$(C_1-C_4)$-alkyl), —PO(OR$^{26}$)(R$^{27}$), morpholinyl or $(C_1-C_4)$-alkylpiperazinyl, or
 (f) —$(C_1-C_4)$-perfluoroalkyl;
$R^{23}$ is
 (a) H,
 (b) aryl as defined above, or
 (c) $(C_1-C_6)$-alkyl optionally substituted with aryl, F, Cl, Br, —OH, —NH$_2$, —NH$(C_1-C_4)$-alkyl, —N[$(C_1-C_4)$-alkyl]$_2$, or CF$_3$;
$R^{24}$ is
 (a) aryl as defined above,
 (b) $(C_1-C_6)$-alkyl optionally substituted with aryl, F, Cl, Br, —OH, —NH$_2$, —NH$(C_1-C_4)$-alkyl, —N[$(C_1-C_4)$-alkyl]$_2$, CF$_3$, —COOR$^{26}$, or CN,
 (c) —OCH(R$^{26}$)—O—R$^{26a}$, or
 (d) —OH, —O—$(C_1-C_6)$-alkyl wherein alkyl is defined in (b);
$R^{25}$ is
 (a) H,
 (b) $(C_1-C_6)$-alkyl optionally substituted with aryl, F, Cl, Br, —OH, —NH$_2$, —NH[$(C_1-C_4)$-alkyl], —N[$(C_1-C_4)$-alkyl]$_2$, CF$_3$, —COOR$^{26}$, or CN, or
 (c) F, Cl, Br;
$R^{26}$ is H, aryl, $(C_1-C_6)$-alkyl, or substituted $(C_1-C_6)$-alkyl wherein the substituent was selected from the group consisting of: aryl or heteroaryl, wherein heteroaryl is an unsubstituted, monosubstituted or disubstituted heteroaromatic 5 or 6 membered ring which contains one to three heteroatoms selected from the group consisting of N, O, and S, and wherein the substituents are members selected from the group consisting of: —OH, —SH $(C_1-C_4)$-alkyl, $(C_1-C_4)$-alkoxy, —CF$_3$, Cl, Br, I, F, and NO$_2$;
$R^{26a}$ is aryl, $(C_1-C_6)$-alkyl or aryl-$(C_1-C_6)$-alkyl;
$R^{27}$ is H, $(C_1-C_5)$-alkyl, aryl or arylmethyl;
$R^{28}$ is H, $(C_1-C_6)$-alkyl, $(C_2-C_4)$-alkenyl, or $(C_1-C_4)$-alkoxyalkyl;
$R^{29}$ is:
 (a) $(C_1-C_4)$-alkyl,
 (b) CHR$^{30}$—O—COR$^{31}$,
 (c) CH$_2$CH$_2$—N[$(C_1-C_2)$-alkyl]$_2$,
 (d) CH$_2$CH$_2$—N[CH$_2$CH$_2$]$_2$O,
 (e) (CH$_2$CH$_2$O)$_y$—O—[$(C_1-C_4)$-alkyl], wherein y is 1 or 2,
 (f) aryl or CH$_2$-aryl, where aryl is as defined above or optionally substituted with CO$_2$—$(C_1-C_4)$-alkyl,
 (g)

(h)

(i)

or (j)

and $R^{30}$ and $R^{31}$ independently are $(C_1-C_6)$-alkyl or phenyl; or its pharmaceutically acceptable salt thereof.

One embodiment of the compounds of formula (I) are those compounds wherein:

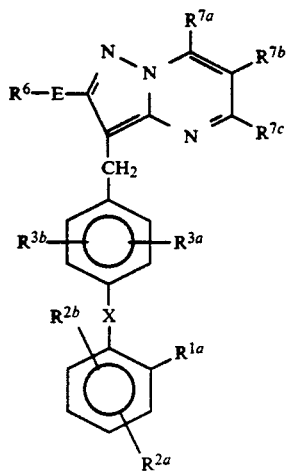

$R^{1a}$ is
(a) —COOH,
(b)

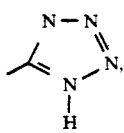

or
(c)

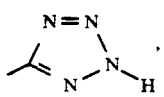

(d)

(e) —NH—SO$_2$CF$_3$,
(f) —CO$_2$R$^{29}$,
(g) —CONHSO$_2$R$^{20}$,
(h) —SO$_2$NHCOR$^{20}$,
(i) —SO$_2$NH-heteroaryl,
(j) —CH$_2$SO$_2$NH-heteroryl,
(k) —CH$_2$SO$_2$NCHO—R$^{20}$,
(l) —CH$_2$CONH—SO$_2$R$^{20}$,
(m) —NHSO$_2$NHCO—R$^{20}$,
(n) —NHCONHSO$_2$—R$^{20}$,
(o) —CONHSO$_2$NR$^4$R$^{20}$,
(p) —SO$_2$NHCONR$^4$R$^{20}$, or
(q) —SO$_2$NHCO$_2$R$^{20}$;

$R^{2a}$ and $R^{2b}$ are H, F, Cl, CF$_3$ or $(C_1-C_6)$-alkyl;
$R^{3a}$ is H;

$R^{3b}$ is H, F, Cl, CF$_3$, $(C_1-C_6)$-alkyl, $(C_5-C_6)$-cycoalkyl, —COOCH$_3$, —COOC$_2$H$_5$, —SO$_2$—CH$_3$, NH$_2$, —N[(C$_1$-C$_4$)-alkyl]$_2$ or —NH—SO$_2$CH$_3$;

E is a single bond, —O— or —S—;
$R^6$ is
(a) $(C_1-C_5)$-alkyl unsubstituted or substituted with a substituent selected from the group consisting of: Cl, CF$_3$, CCl$_3$, —O—CH$_3$, —OC$_2$H$_5$, —S—CH$_3$, —S—C$_2$H$_5$ or phenyl;
(b) $(C_2-C_5)$-alkenyl or $(C_2-C_5)$-alkynyl;
(c) $(C_3-C_5)$-cycloalkyl;

$R^{7a}$, $R^{7b}$ and $R^{7c}$ are independently
(a) H,
(b) $(C_1-C_4)$-alkyl,
(c) $(C_2-C_4)$-alkenyl,
(d) —OH,
(e) —CH$_2$OCOR$^4$,
(f) —NH$_2$,
(g)

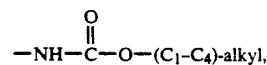

(h)

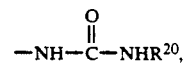

(i) —(C$_1$-C$_4$)-alkoxy,
(j) —NH[(C$_1$-C$_4$)-alkyl],
(k) —N[(C$_1$-C$_4$)-alkyl]$_2$,
(l) Cl, F, or Br,
(m) —CF$_3$,
(n) —CO$_2$R$^4$,
(o) —CH$_2$—OH,
(p) 5 to 6 membered saturated heterocycle containing one nitrogen atom and optionally containing one other heteroatom selected from N, O, or S, such as pyrrolidine, morpholine, or piperazine,
(q) —CO-aryl as defined above,
(r) —S(O)$_n$—(C$_1$-C$_4$)-alkyl,
(s) —SO$_2$—NH—(C$_1$-C$_4$)-alkyl,
(t) —SO$_2$—NH-aryl,
(u) —NH—SO$_2$CH$_3$,
(v) aryl,
(w) heteroaryl,
(x) —N[CH$_2$CH$_2$]G, or
(y) CON[CH$_2$CH$_2$]$_2$G
(z) CON(R$^4$)$_2$,
(aa)

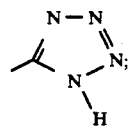

and,
x is a C—C single bond or —CO—.

In a class of this embodiment are those compounds wherein:
$R^{1a}$ is
(a) —COOH,
(b)

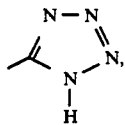

(c)

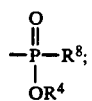

(d) —NH—SO$_2$—CF$_3$,
(e) —CONHSO$_2$R$^{20}$,
(f) —SO$_2$NHCOR$^{20}$,
(g) —SO$_2$NH-heteroaryl,
(h) —CH$_2$SO$_2$NH-heteroaryl,
(i) —CH$_2$SO$_2$NHCO—R$^{20}$,
(j) —CH$_2$CONH—SOR$^{20}$,
(k) —NHSO$_2$NHCO—R$^{20}$,
(l) —NHCONHSO$_2$—R$^{20}$,
(m) —CONHSO$_2$NR$^4$R$^{20}$,
(n) —SO$_2$NHCONR$^4$R$^{20}$, or
(o) —SO$_2$NHCO$_2$R$^{20}$, R$^{2a}$, R$^{2b}$, R$^{3a}$ and R$^{3b}$ are each H;
R$^6$ is n-propyl, n-butyl, methyl, ethyl, cyclopropyl, or —CH$_2$—S—CH$_3$;
R$^{7a}$ is —(C$_1$-C$_4$)-alkyl, aryl, heteroaryl, —(C$_1$-C$_4$)-perfluoroalkyl, —(C$_3$-C$_6$)-cycloalkyl;
R$^{7b}$ is —H, —F, —Cl, —(C$_1$-C$_4$)-alkyl, —(C$_1$-C$_4$)-perfluoroalkyl;
R$^{7c}$ is —(C$_1$-C$_4$)-alkyl, aryl, heteroaryl, —(C$_1$-C$_4$)-perfluoroalkyl, —(C$_3$-C$_6$)-cycloalkyl, CO$_2$R$^4$, 1H-tetrazol-5-yl, N[CH$_2$CH$_2$]$_2$NH, N[CH$_2$CH$_2$]$_2$NCOR$^{20}$, NHSO$_2$CF$_3$, SO$_2$NHCOR$^{20}$, or CON[(C$_1$-C$_2$)-alkyl]$_2$;

Exemplifying the foregoing class are the following compounds:

(1) 2-Butyl-3-[(2'-carboxybiphen-4-yl)methyl]-pyrazolo[1,5-a]pyrimidine;
(2) 3-[(2'-Carboxybiphen-4-yl)methyl]-2-propyl-pyrazolo[1,5-a]pyrimidine;
(3) 3-[(2'-Carboxybiphen-4-yl)methyl]-2-ethyl-pyrazolo[1,5-a]pyrimidine;
(4) 3-[(2'-Carboxbiphen-4-yl)methyl]-2-isopropyl-pyrazolo[1,5-a]pyrimidine;
(5) 3-[(2'-Carboxybiphen-4-yl)methyl]-2-cyclopropyl-pyrazolo[1,5-a]pyrimidine;
(6) 3-[(2'-Carboxybiphen-4-yl)methyl]-7-methyl-2-propylpyrazolo[1,5-a]pyrimidine;
(7) 3-[(2'-Carboxybiphen-4-yl)methyl]-7-ethyl-2-propyl-pyrazolo[1,5-a]pyrimidine;
(8) 3-[(2'-Carboxybiphen-4yl)methyl]-2-ethyl-7-methyl-pyrazolo[1,5-a]pyrimidine;
(9) 3-[(2'-Carboxybiphen-4-yl)methyl]-2,7-diethyl-pyrazolo[1,5-a]pyrimidine;
(10) 3-[(2'-Carboxybiphen-4-yl)methyl]-5,7-dimethyl-2-propylpyrazolo[1,5-a]pyrimidine;
(11) 3-[(2'-Carboxybiphen-4-yl)methyl]-5,7-dimethyl-2-ethylpyrazolo[1,5-a]pyrimidine;
(12) 3-[(2'-Carboxybiphen-4-yl)methyl]-2-cyclopropyl-5,7-dimethylpyrazolo[1,5-a]pyrimidine;
(13) 3-[(2'-Carboxybiphen-4-yl)methyl]-5-ethyl-7-methyl-2-propylpyrazolo[1,5-a]pyrimidine;
(14) 3-[(2'-Carboxybiphen-4-yl)methyl]-2,5-diethyl-7-methylpyrazolo[1,5-a]pyrimidine;
(15) 3-[(2'-Carboxybiphen-4-yl)methyl]-2-ethyl-7-methyl-5-methylaminopyrazolo[1,5-a]pyrimidine;
(16) 5-Amino-3-[(2'-carboxybiphen-4-yl)methyl]-7-methyl-2-ethylpyrazolo[1,5-a]pyrimidine;
(17) 3-[(2'-Carboxybiphen-4-yl)methyl]-2-ethyl-5-methylamino-7-trifluoromethylpyrazolo[1,5-a]pyrimidine;
(18) 3-[(2'-Carboxybiphen-4-yl)methyl]-2-ethyl-5-methyl-7-methylaminopyrazolo[1,5-a]pyrimidine;
(19) 3-[(2'-Carboxybiphen-4-yl)methyl]-7-dimethylamino-2-ethyl-5-methylpyrazolo[1,5-a]pyrimidine;
(20) 3-[(2'-Carboxybiphen-4-yl)methyl]-2-ethyl-5-methyl-7-phenylaminopyrazolo[1,5-a]pyrimidine;
(21) 3-[(2'-Carboxybiphen-4-yl)methyl]-2-ethyl-5-methyl-7-(morpholin-4-yl)pyrazolo[1,5-a]pyrimidine;
(22) 3-[(2'-Carboxybiphen-4-yl)methyl]-2-ethyl-7-methyl-5-(morpholin-4-yl)pyrazolo[1,5-a]pyrimidine;
(23) 3-[(2'-Carboxybiphen-4-yl)methyl]-2-ethyl-7-methoxy-5-methylpyrazolo[1,5-a]pyrimidine;
(24) 3-[(2'-Carboxybiphen-4-yl)methyl]-2-ethyl-5-hydroxymethyl-7-methylpyrazolo[1,5-a]pyrimidine;
(25) 5-Carboxy-3-[(2'-carboxybiphen-4-yl)methyl]-2-ethyl-7-methylpyrazolo[1,5-a]pyrimidine;
(26) 5-Carbomethoxy-3-[(2'-carboxybiphen-4-yl)methyl]-2-ethyl-7-methylpyrazolo[1,5-a]pyrimidine;
(27) 3-[(2'-Carboxybiphen-4-yl)methyl]-2-ethyl-7-methyl-5-phenylpyrazolo[1,5-a]pyrimidine;
(28) 3-[(2'-Carboxybiphen-4-yl)methyl]-5-(2-chloro)phenyl-2-ethyl-7-methylpyrazolo[1,5-a]pyrimidine;
(29) 3-[(2'-Carboxybiphen-4-yl)methyl]-5-(4-chloro)phenyl-2-ethyl-7-methylpyrazolo[1,5-a]pyrimidine;
(30) 3-[(2'-Carboxybiphen-4-yl)methyl]-2-ethyl-7-methyl-5-(2-trifluoromethyl)phenylpyrazolo[1,5-a]pyrimidine;
(31) 6-Amino-3-[(2'-carboxybiphen-4-yl)methyl]-5,7-dimethyl-2-ethylpyrazolo[1,5-a]pyrimidine;
(32) 3-[(2'-Carboxybiphen-4-yl)methyl]-5,7-dimethyl-2-ethyl-6-ethylaminopyrazolo[1,5-a]pyrimidine;
(33) 3-[(2'-Carboxybiphen-4-yl)methyl]-5,7-dimethyl-2-ethyl-6-fluoropyrazolo[1,5-a]pyrimidine;
(34) 3-[(2'-Carboxybiphen-4-yl)methyl]-5,7-dimethyl-2-(2,2,2-trifluoroethylpyrazolo[1,5-a]pyrimidine;
(35) 3-[(2'-Carboxybiphen-4-yl)methyl]-5,7-dimethyl-2-(pentafluoroethylpyrazolo[1,5-a]pyrimidine;
(36) 3-[(2'-Carboxybiphen-4-yl)methyl]-5,7-dimethyl-2-(3,3,3-trifluoroethylpyrazolo[1,5-a]pyrimidine;
(37) 3-[(2'-Carboxybiphen-4-yl)methyl]-5,7-dimethyl-2-(4,4,4-trifluorobutylpyrazolo[1,5-a]pyrimidine;
(38) 3-[(2'-Carboxybiphen-4-yl)methyl]-5,7-dimethyl-2-(2,2-difluoropropylpyrazolo[1,5-a]pyrimidine;
(39) 3-[(2'-Carboxybiphen-4-yl)methyl]-5,7-dimethyl-2-trans-2-butenylpyrazolo[1,5-a]pyrimidine;
(40) 3-[(2'-Carboxybiphen-4-yl)methyl]-5,7-dimethyl-2-trans-1-propenylpyrazolo[1,5-a]pyrimidine;
(41) 2-Allyl-3-[(2'-carboxybiphen-4-yl)methyl]-5,7-dimethylpyrazolo[1,5-a]pyrimidine;
(42) 3-[(2'-Carboxybiphen-4-yl)methyl]-5,7-dimethyl-2-(2-propynyl)pyrazolo[1,5-a]pyrimidine;
(43) 2-(2-Butynyl)-3-[(2'-carboxybiphen-4-yl)methyl]5,7-dimethylpyrazolo[1,5-a]pyrimidine;
(44) 3-[(2'-Carboxybiphen-4-yl)methyl]-5,7-dimethyl-2-(4,4,4-trifluoro-2-butynyl)pyrazolo[1,5-a]pyrimidine;
(45) 3-[(2'-Carboxybiphen-4-yl)methyl]-5,7-dimethyl-2-(2,2,2-trifluoroethoxy)pyrazolo[1,5-a]pyrimidine;

(46) 2-Butyl-3-[(2'-(tetrazol-5-yl)biphen-4-yl)methyl]-pyrazolo[1,5-a]pyrimidine;
(47) 2-Propyl-3-[(2'-(tetrazol-5-yl)biphen-4-yl)methyl]-pyrazolo[1,5-a]pyrimidine;
(48) 2-Ethyl-3-[(2'-(tetrazol-5-yl)biphen-4-yl)methyl]-pyrazolo[1,5-a]pyrimidine;
(49) 2-Isopropyl-3-[(2'-(tetrazol-5-yl)biphen-4-yl)methyl]pyrazolo[1,5-a]pyrimidine;
(50) 2-Cyclopropyl-3-[(2'-(tetrazol-5-yl)biphen-4-yl)methyl]pyrazolo[1,5-a]pyrimidine;
(51) 7-Methyl-2-propyl-3-[(2'-(tetrazol-5-yl)biphen-4-yl)methyl]pyrazolo[1,5-a]pyrimidine;
(52) 7-Ethyl-2-propyl-3-[(2'-(tetrazol-5-yl)biphen-4-yl)methyl]pyrazolo[1,5-a]pyrimidine;
(53) 2-Ethyl-7-methyl-3-[(2'-(tetrazol-5-yl)biphen-4-yl)methyl]pyrazolo[1,5-a]pyrimidine;
(54) 2,7-Diethyl-3-[(2'-(tetrazol-5-yl)biphen-4-yl)methyl]pyrazolo[1,5-a]pyrimidine;
(55) 5,7-Dimethyl-2-propyl-3-[(2'-(tetrazol-5-yl)biphen-4-yl)methyl]pyrazolo[1,5-a]pyrimidine;
(56) 5,7-Dimethyl-2-ethyl-3-[(2'-(tetrazol-5-yl)biphen-4-yl)methyl]pyrazolo[1,5-a]pyrimidine;
(57) 2-Cyclopropyl-5,7-dimethyl-3-[(2'-(tetrazol-5-yl)biphen-4-yl)methyl]pyrazolo[1,5-a]pyrimidine;
(58) 5-Ethyl-7-methyl-2-propyl-3-[(2'-(tetrazol-5-yl)biphen-4-yl)methyl]pyrazolo[1,5-a]pyrimidine;
(59) 2,5-Diethyl-7-methyl-3-[(2'-(tetrazol-5-yl)biphen-4-yl)methyl]pyrazolo[1,5-a]pyrimidine;
(60) 2-Ethyl-7-methyl-5-methylamino-3-[(2'-(tetrazol-5-yl)biphen-4-yl)methyl]pyrazolo[1,5-a]pyrimidine;
(61) 5-Amino-7-methyl-2-ethyl-3-[(2'-(tetrazol-5-yl)biphen-4-yl)methyl]pyrazolo[1,5-a]pyrimidine;
(62) 2-Ethyl-5-methylamino-7-trifluoromethyl-3-[(2'-(tetrazol-5-yl)biphen-4-yl)methyl]pyrazolo[1,5-a]pyrimidine;
(63) 2-Ethyl-5-methyl-7-methylamino-3-[(2'-(tetrazol-5-yl)biphen-4-yl)methyl]pyrazolo[1,5-a]pyrimidine;
(64) 7-Dimethylamino-2-ethyl-5-methyl-3-[(2'-(tetrazol-5-yl)biphen-4-yl)methyl]pyrazolo[1,5-a]pyrimidine;
(65) 2-Ethyl-5-methyl-7-phenylamino-3-[(2'-(tetrazol-5-yl)biphen-4-yl)methyl]pyrazolo[1,5-a]pyrimidine;
(66) 2-Ethyl-5-methyl-7-(morpholin-4-yl)-3-[(2'-(tetrazol-5-yl)biphen-4-yl)methyl]pyrazolo[1,5-a]pyrimidine;
(67) 2-Ethyl-7-methyl-5-(morpholin-4-yl)-3-[(2'-(tetrazol-5-yl)biphen-4-yl)methyl]pyrazolo[1,5-a]pyrimidine;
(68) 2-Ethyl-7-methoxy-5-methyl-3-[(2'-(tetrazol-5-yl)biphen-4-yl)methyl]pyrazolo[1,5-a]pyrimidine;
(69) 2-Ethyl-5-hydroxymethyl-7-methyl-3-[(2'-(tetrazol-5-yl)biphen-4-yl)methyl]pyrazolo[1,5-a]pyrimidine;
(70) 5-Carboxy-2-ethyl-7-methyl-3-[(2'-(tetrazol-5-yl)biphen-4-yl)methyl]pyrazolo[1,5-a]pyrimidine;
(71) 5-Carbomethoxy-2-ethyl-7-methyl-3-[(2'-(tetrazol-5-yl)biphen-4-yl)methyl]pyrazolo[1,5-a]pyrimidine;
(72) 2-Ethyl-7-methyl-5-phenyl-3-[(2'-(tetrazol-5-yl)biphen-4-yl)methyl]pyrazolo[1,5-a]pyrimidine;
(73) 5-(2-Chloro)phenyl-2-ethyl-7-methyl-3-[(2'-(tetrazol-5-yl)biphen-4-yl)methyl]pyrazolo[1,5-a]pyrimidine;
(74) 5-(4-Chloro)phenyl-2-ethyl-7-methyl-3-[(2'-(tetrazol-5-yl)biphen-4-yl)methyl]pyrazolo[1,5-a]pyrimidine;
(75) 2-Ethyl-7-methyl-5-(2-trifluoromethyl)phenyl-3-[(2'-(tetrazol-5-yl)biphen-4-yl)methyl]pyrazolo[1,5-a]pyrimidine;
(76) 6-Amino-5,7-dimethyl-2-ethyl-3-[(2'-(tetrazol-5-yl)biphen-4-yl)methyl]pyrazolo[1,5-a]pyrimidine;
(77) 5,7-Dimethyl-2-ethyl-6-ethylamino-3-[(2'-(tetrazol-5-yl)biphen-4-yl)methyl]pyrazolo[1,5-a]pyrimidine;
(78) 5,7-Dimethyl-2-ethyl-6-fluoro-3-[(2'-(tetrazol-5-yl)biphen-4-yl)methyl]pyrazolo[1,5-a]pyrimidine;
(79) 5,7-Dimethyl-3-[(2'-(tetrazol-5-yl)biphen-4-yl)methyl]-2-(2,2,2-trifluoroethylpyrazolo[1,5-a]pyrimidine;
(80) 5,7-Dimethyl-2-(pentafluoroethyl-3-[(2'-(tetrazol-5-yl)biphen-4-yl)methyl]pyrazolo[1,5-a]pyrimidine;
(81) 5,7-Dimethyl-3-[(2'-(tetrazol-5-yl)biphen-4-yl)methyl]-2-(3,3,3-trifluoropropylpyrazolo[1,5-a]pyrimidine;
(82) 5,7-Dimethyl-3-[(2'-(tetrazol-5-yl)biphen-4-yl)methyl]-2-(4,4,4-trifluorobutylpyrazolo[1,5-a]pyrimidine;
(83) 5,7-Dimethyl-2-(2,2-difluoropropyl-3-[(2'-(tetrazol-5-yl)biphen-4-yl)methyl]pyrazolo[1,5-a]pyrimidine;
(84) 5,7-Dimethyl-2-trans-2-butenyl-3-[(2'-(tetrazol-5-yl)biphen-4-yl)methyl]pyrazolo[1,5-a]pyrimidine;
(85) 5,7-Dimethyl-3-[(2'-(tetrazol-5-yl)biphen-4-yl)methyl]-2-trans-1-propenylpyrazolo[1,5-a]pyrimidine;
(86) 2-Allyl-5,7-dimethyl-3-[(2'-(tetrazol-5-yl)biphen-4-yl)methyl]pyrazolo[1,5-a]pyrimidine;
(87) 5,7-Dimethyl-2-(2-propynyl)-3-[(2'-(tetrazol-5-yl)biphen-4-yl)methyl]pyrazolo[1,5-a]pyrimidine;
(88) 2-(2-Butynyl)-5,7-dimethyl-3-[(2'-(tetrazol-5-yl)biphen-4-yl)methyl]pyrazolo[1,5-a]pyrimidine;
(89) 5,7-Dimethyl-3-[(2'-(tetrazol-5-yl)biphen-4-yl)methyl]-2-(4,4,4-trifluoro-2-butynyl)pyrazolo[1,5-a]pyrimidine;
(90) 5,7-Dimethyl-3-[(2'-(tetrazol-5-yl)biphen-4-yl)methyl]-2-(2,2,2-trifluoroethoxy)pyrazolo[1,5-a]-pyrimidine;
(91) 5,7-Dimethyl-2-ethyl-3-[(2'-(N-((phenylsulfonyl)carboxamido)biphen-4-yl)methyl]pyrazolo[1,5-a]pyrimidine;
(92) 5,7-Dimethyl-2-ethyl-3-[(2'-(N-((methylsulfonyl)carboxamido)biphen-4-yl)methyl]pyrazolo[1,5-a]pyrimidine;
(93) 5,7-Dimethyl-2-ethyl-3-[(2'-(N-((trifluoromethylsulfonyl)carboxamido)biphen-4-yl)methyl]-pyrazolo[1,5-a]pyrimidine;
(94) 3-[(2'-(N-((2-Aminoethyl)sulfonyl)carboxamido)biphen-4-yl)methyl]-5,7-dimethyl-2-ethylpyrazolo[1,5-a]pyrimidine;
(95) 5,7-Dimethyl-2-ethyl-3-[(2'-(N-((morpholin-4-yl)sulfonyl)carboxamido)biphen-4-yl)methyl]-pyrazolo[1,5-a]pyrimidine;
(96) 5,7-Dimethyl-[(2'-(N,N-dimethylaminosulfonyl)-carboxamido)biphen-4-yl)methyl]-2-ethyl-3-pyrazolo[1,5-a]pyrimidine;
(97) 3-[(2'-(N-(Cyclopentylsulfonyl)carboxamido)biphen-4-yl)methyl]-5,7-dimethyl-2-ethylpyrazolo[1,5-a]pyrimidine;
(98) 5,7-Dimethyl-2-ethyl-3-[(2'-(N-(pyrimidin-2-yl)biphen-4-yl)methyl]pyrazolo[1,5-a]pyrimidine;
(99) 5,7-Dimethyl-3-[(2'-(N-(4,6-dimethylpyrimidin-2-yl)sulfamido)biphen-4-yl)methyl]-2-ethylpyrazolo[1,5-a]pyrimidine;
(100) 5,7-Dimethyl-2-ethyl-3-[(2'-(N-((triazin-2-yl)sulfamido)biphen-4-yl)methyl]pyrazolo[1,5-a]pyrimidine;
(101) 5,7-Dimethyl-2-ethyl-3-[(2'-(N-(oxazol-2-yl)sulfamido)biphen-4-yl)methyl]pyrazolo[1,5-a]pyrimidine;

(102) 3-[(2'-(N-(Acetyl)sulfonamido)biphen-4-yl)methyl]-5,7-dimethyl-2-ethylpyrazolo[1,5-a]pyrimidine;

(103) 3-[(2'-(N-(Benzoyl)sulfonamido)biphen-4-yl)methyl]-5,7-dimethyl-2-ethylpyrazolo[1,5-a]pyrimidine;

(104) 5,7-Dimethyl-2-ethyl-3-[(2'-(N-(4-nitrobenzoyl)-sulfamido)biphen-4-yl)methyl]pyrazolo[1,5-a]pyrimidine;

(105) 3-[(2'-(N-(4-Chlorobenzoyl)sulfonamido)biphen4-yl)methyl]-5,7-dimethyl-2-ethylpyrazolo[1,5-a]-pyrimidine;

(106) 5,7-Dimethyl-2-ethyl-3-[(2'-(N-((morpholin-4-yl)carbonyl)sulfamido)biphen-4-yl)methyl]-pyrazolo[1,5-a]pyrimidine;

(107) 5,7-Dimethyl-2-ethyl-3-[(2'-(N-((piperazin-1-yl)carbonyl)sulfamido)biphen-4-yl)methyl]-pyrazolo[1,5-a]pyrimidine;

(108) 5,7-Dimethyl-2-ethyl-3-[(2'-((N-(trifluoromethyl)-carbonyl)sulfamido)biphen-4-yl)methyl]-pyrazolo[1,5-a]pyrimidine;

(109) 3-[(2'-(N-((2-Carboxyethyl)carbonyl)sulfamido)-biphen-4-yl)methyl]-5,7-dimethyl-2-ethyl-pyrazolo[1,5-a]pyrimidine;

(110) 5,7-Dimethyl-3-[(2'-((N-(2-ethoxyethyl)carbonyl)-sulfamido)biphen-4-yl)methyl]-2-ethylpyrazolo[1,5-a]pyrimidine;

(111) 5,7-Dimethyl-2-ethyl-3-[(2'-(N-((phenylsulfonyl)-carboxamido)methylbiphen-4-yl)methyl]-pyrazolo[1,5-a]pyrimidine;

(112) 5,7-Dimethyl-3-[(2'-(N-(4,6-dimethylpyrimidin-2-yl)sulfamido)methylbiphen-4-yl)methyl]-2-ethyl-pyrazolo[1,5-a]pyrimidine;

(113) 5-Carboethoxy-2-cyclopropyl-7-methyl-3-[(2'-(tetrazol-5-yl)biphen-4-yl)methyl]pyrazolo[1,5-a]pyrimidine;

(114) 5-Carboethoxy-7-methyl-2-propyl-3-[(2'-(tetrazol-5-yl)biphen-4-yl)methyl]pyrazolo[1,5-a]pyrimidine;

(115) 3-[(2'-(N-(Benzoyl)sulfonamido)biphen-4-yl)methyl]-5-carboethoxy-2-cyclopropyl-7-methyl-pyrazolo[1,5-a]pyrimidine; and, (116) 3-[(2'-(N-(Benzoyl)sulfonamido)biphen-4-yl)methyl]-5-carboethoxy-7-methyl-2-propylpyrazolo[1,5-a]pyrimidine.

(117) 2-Cyclopropyl-5,7-dimethyl-3-[(2'-(N-(butoxycarbonyl)sulfonamido)biphen-4-yl)methyl]pyrazolo[1,5-a]pyrimidine;

(118) 2-Cyclopropyl-5,7-dimethyl-3-[(2'-(N-(butoxycarbonyl)sulfonamido)-5'-isobutylbiphen-4-yl)methyl]pyrazolo[1,5-a]pyrimidine;

(119) 2-Cyclopropyl-5,7-dimethyl-3-[(2'-(N-(butoxycarbonyl)sulfonamido)-5'-propylbiphen-4-yl)methyl]pyrazolo[1,5-a]pyrimidine;

(120) 2-Cyclopropyl-5,7-dimethyl-3-[(2'-(N-(propoxycarbonyl)sulfonamido)-5'-isobutylbiphen-4-yl)methyl]pyrazolo[1,5-a]pyrimidine;

(121) 2-Cyclopropyl-5,7-dimethyl-3-[(2'-(N-(cyclopropanecarbonyl)sulfonamido)biphen-4-yl)methyl]pyrazolo[1,5-a]pyrimidine;

(122) 2-Cyclopropyl-5,7-dimethyl-3-[(2'-(N-((R)-2,2-dimethylcyclopropane-1-carbonyl)sulfonamido)biphen-4-yl)methyl]pyrazolo[1,5-a]pyrimidine;

(123) 2-Cycloproyl-5,7-dimethyl-3-[(2'-(N-((S)-2,2-dimethylcyclopropane-1-carbonyl)sulfonamido)biphen-4-yl)methyl]pyrazolo[1,5-a]pyrimidine;

(124) 2-Cyclopropyl-5,7-dimethyl-3-[(2'-(N-(cyano)sulfonamido)biphen-4-yl)methyl]pyrazolo[1,5-a]pyrimidine;

(125) 2-Cyclopropyl-5,7-dimethyl-3-[(2'-(N-(2-thiazolo)sulfonamido)biphen-4-yl)methyl]-pyrazolo[1,5-a]pyrimidine;

(126) N,N, 7-trimethyl-2-cyclopropyl-3-[(2'-(tetrazol-5-yl)biphen-4-yl)methyl]pyrazolo[1,5-a]pyrimidine-5-carboxamide;

(127) N,N-diethyl-2-cyclopropyl-7-methyl-3-[(2'-(tetrazol-5-yl)biphen-4-yl)methyl]pyrazolo[1,5-a]pyrimidine-5-carboxamide;

(128) N,N, 7-trimethyl-2-cyclopropyl-3-[(2'-(N-(cyclopropanecarbonyl)sulfonamido)biphen-4-yl)methyl]pyrazolo[1,5-a]pyrimidine-5-carboxamide;

(129) N,N, 7-trimethyl-2-cyclopropyl-3-[(2'-(N-((R)-2,2-dimethylcyclopropane-1-carbonyl)sulfonamido)-biphen-4-yl)methyl]pyrazolo[1,5-a]pyrimidine-5-carboxamide;

(130) N,N, 7-trimethyl-2-cyclopropyl-3-[(2'-(N-((S)-2,2-dimethylcyclopropane-1-carbonyl)sulfonamido)biphen-4-yl)methyl]pyrazolo[1,5-a]pyrimidine-5-carboxamide;

(131) N,N, 7-trimethyl-2-cyclopropyl-3-[(2'-(N-(cyano)sulfonamido)biphen-4-yl)methyl]pyrazolo[1,5-a]pyrimidine-5-carboxamide;

(132) N,N, 7-trimethyl-2-cyclopropyl-3-[(2'-(N-(2-thiazolo)sulfonamido)biphen-4-yl)methyl]pyrazolo[1,5-a]pyrimidine-5-carboxamide.

In a second embodiment are those compounds of formula (I)

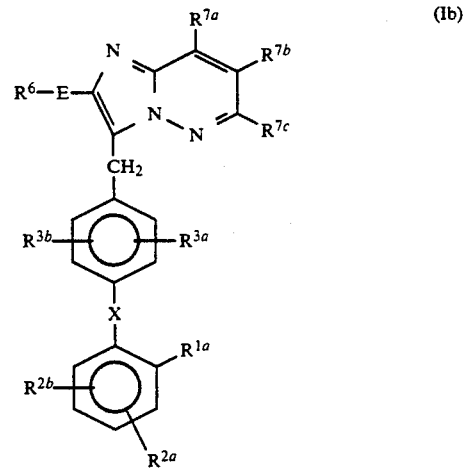

(Ib)

wherein:
$R^{1a}$ is (a) —COOH, (b)

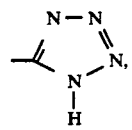

(c)

(d) —NH—SO$_2$CF$_3$, (e) —CO$_2$R$^{29}$,
(f) —CONHSO$_2$R$^{20}$,
(g) —SO$_2$NHCOR$^{20}$,
(h) —SO$_2$NH-heteroaryl,
(i) —CH$_2$SO$_2$NH-heteroaryl,
(j) —CH$_2$SO$_2$NHCO—R$^{20}$,
(k) —CH$_2$CONH—SO$_2$R$^{20}$,
(l) —NHSO$_2$NHCO—R$^{20}$,
(m) —NHCONHSO$_2$—R$^{20}$,
(n) —CONHSO$_2$NR$^4$R$^{20}$,
(o) —SO$_2$NHCONR$^4$R$^{20}$, or
(p) —SO$_2$NHCO$_2$R$^{20}$;

R$^{2a}$ and R$^{2b}$ are H, F, Cl, CF$_3$, (C$_1$-C$_6$)-alkyl, (C$_2$-C$_6$)-alkenyl, or (C$_2$-C$_6$)-alkynyl;

R$^{3a}$ is H, F or Cl;

R$^{3b}$ is H, F, Cl, CF$_3$, (C$_1$-C$_6$)-alkyl, (C$_2$-C$_6$)-alkenyl, (C$_2$-C$_6$)-alkynyl, (C$_5$-C$_6$)-cycloalkyl, —COOCH$_3$, —COOC$_2$H$_5$, —SO$_2$—CH$_3$, —N(R$^4$)$_2$ or —N-H—SO$_2$CH$_3$;

E is a single bond, —O— or —S—;

R$^6$ is
  (a) (C$_1$-C$_5$)-alkyl unsubstituted or substituted with a substituent selected from the group consisting of: Cl, CF$_3$, CCl$_3$, —O—CH$_3$, —OC$_2$H$_5$, —S—CH$_3$, —S—C$_2$H$_5$ or phenyl;
  (b) (C$_2$-C$_5$)-alkenyl or (C$_2$-C$_5$)-alkynyl, or
  (c) (C$_3$-C$_5$)-cycloalkyl;

R$^{7a}$, R$^{7b}$ and R$^{7c}$ are independently
  (a) H,
  (b) (C$_1$-C$_4$)-alkyl,
  (c) (C$_2$-C$_4$)-alkenyl,
  (d) —OH,
  (e) —CH$_2$OCOR$^4$,
  (f) —NH$_2$,
  (g)

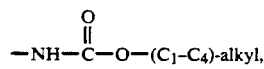

(h)

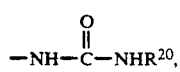

(i) —(C$_1$-C$_4$)-alkoxy,
  (j) —NH[(C$_1$-C$_4$)-alkyl],
  (k) —N[(C$_1$-C$_4$)-alkyl]$_2$,
  (l) Cl, F, Br,
  (m) —CF$_3$,
  (n) —CO$_2$R$^4$,
  (o) —CH$_2$—OH,
  (p) 5 or 6 membered saturated heterocycle,
  (q) —CO-aryl,
  (r) —S(O)$_n$—(C$_1$-C$_4$)-alkyl
  (s) —SO$_2$—NH—(C$_1$-C$_4$)-alkyl,
  (t) —SO$_2$—NH-aryl,
  (u) —NH—SO$_2$CH$_3$,
  (v) aryl,
  (w) heteroaryl,
  (x) —N[CH$_2$CH$_2$]G,
  (y) —CON[CH$_2$CH$_2$[$_2$G,
  (z) —CON(R$^4$)$_2$, or
  (aa)

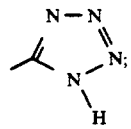

and,

X is a C—C single bond or —CO—.

In a class of this embodiment are those compounds wherein:

R$^{1a}$ is
  (a) —COOH,
  (b)

(c)

$$\begin{matrix} O \\ \| \\ -P-R^8; \\ | \\ OR^4 \end{matrix}$$

(d) —NH—SO$_2$—CF$_3$,
  (e) —CONHSO$_2$R$^{20}$;
  (f) —SO$_2$NHCOR$^{20}$;
  (g) —SO$_2$NH-heteroaryl,
  (h) —CH$_2$SO$_2$NH-heteroaryl,
  (i) —CH$_2$SO$_2$NHCO—R$^{20}$,
  (j) —CH$_2$CONH—SOR$^{20}$,
  (k) —NHSO$_2$NHCO—R$^{20}$,
  (l) —NHCONHSO$_2$—R$^{20}$,
  (m) —CONHSO$_2$NR$^4$R$^{20}$,
  (n) —SO$_2$NHCONR$^4$R$^{20}$, or
  (o) —SO$_2$NHCO$_2$R$^{20}$;

R$^{2a}$, R$^{2b}$, R$^{3a}$ and R$^{3b}$ are each H;

R$^6$ is n-propyl, n-butyl, methyl, ethyl, cyclopropyl or —CH$_2$—S—CH$_3$;

R$^{7a}$ is —(C$_1$-C$_4$)-alkyl, aryl, heteroaryl, —(C$_1$-C$_4$)-perfluoroalkyl, —(C$_3$-C$_6$)-cycloalkyl;

R$^{7b}$ is —H, —F, —Cl, —(C$_1$-C$_4$)-alkyl, —(C$_1$-C$_4$)-perfluoroalkyl;

R$^{7c}$ is —(C$_1$-C$_4$)-alkyl, aryl, heteroaryl, —(C$_1$-C$_4$)-perfluoroalkyl, CON(R$^4$)$_2$, —(C$_3$-C$_6$)-cycloalkyl, CO$_2$R$^4$, 1H-tetrazol-5-yl, N[CH$_2$CH$_2$]$_2$NH, N[CH$_2$CH$_2$]$_2$NCOR$^{20}$, NHSO$_2$CF$_3$, SO$_2$NH-COR$^{20}$, or CON[(C$_1$-C$_2$)-alkyl]$_2$;

E is a single bond or —S—; and,

X is a single bond.

Exemplifying the foregoing class are the following compounds:

(1) 2-Butyl-3-[(2'-carboxybiphen-4-yl)methyl-]imidazo[1,2-b]pyridazine;

(2) 3-[(2'-Carboxybiphen-4-yl)methyl]-2-propylimidazo[1,2-b]pyridazine;

(3) 3-[(2'-Carboxybiphen-4-yl)methyl]-2-ethylimidazo[1,2-b]pyridazine;

(4) 3-[(2'-Carboxybiphen-4-yl)methyl]-2-isopropylimidazo[1,2-b]pyridazine;

(5) 3-[(2'-Carboxybiphen-4-yl)methyl]-2-cyclopropylimidazo[1,2-b]pyridazine;

(6) 3-[(2'-Carboxybiphen-4-yl)methyl]-7-methyl-2-propylimidazo[1,2-b]pyridazine;
(7) 3-[(2'-Carboxybiphen-4-yl)methyl]-7-ethyl-2-propylimidazo[1,2-b]pyridazine;
(8) 3-[(2'-Carboxybiphen-4-yl)methyl]-2-ethyl-7-methylimidazo[1,2-b]pyridazine;
(9) 3-[(2'-Carboxybiphen-4-yl)methyl]-2,7-diethylimidazo[1,2-b]pyridazine;
(10) 3-[(2'-Carboxybiphen-4-yl)methyl]-5,7-dimethyl-2-propylimidazo[1,2-b]pyridazine;
(11) 3-[(2'-Carboxybiphen-4-yl)methyl]-5,7-dimethyl-2-ethylimidazo[1,2-b]pyridazine;
(12) 3-[(2'-Carboxybiphen-4-yl)methyl]-2-cyclopropyl-5,7-dimethylimidazo[1,2-b]pyridazine;
(13) 3-[(2'-Carboxybiphen-4-yl)methyl]-5-ethyl-7-methyl-2-propylimidazo[1,2-b]pyridazine;
(14) 3-[(2'-Carboxybiphen-4-yl)methyl]-2,5-diethyl-7-methylimidazo[1,2-b]pyridazine;
(15) 3-[(2'-Carboxybiphen-4-yl)methyl]-2-ethyl-7-methyl-5-methylaminoimidazo[1,2-b]pyridazine;
(16) 5-Amino-3-[(2'-carboxybiphen-4-yl)methyl]-7-methyl-2-ethylimidazo[1,2-b]pyridazine;
(17) 3-[(2'-Carboxybiphen-4-yl)methyl]-2-ethyl-5-methylamino-7-trifluoromethylimidazo[1,2-b]pyridazine;
(18) 3-[(2'-Carboxybiphen-4-yl)methyl]-2-ethyl-5-methyl-7-methylaminoimidazo[1,2-b]pyridazine;
(19) 3-[(2'-Carboxybiphen-4-yl)methyl]-7-dimethylamino-2-ethyl-5-methylimidazo[1,2-b]pyridazine;
(20) 3-[(2'-Carboxybiphen-4-yl)methyl]-2-ethyl-5-methyl-7-phenylaminoimidazo[1,2-b]pyridazine;
(21) 3-[(2'-Carboxybiphen-4-yl)methyl]-2-ethyl-5-methyl-7-(morpholin-4-yl)imidazo[1,2-b]pyridazine;
(22) 3-[(2'-Carboxybiphen-4-yl)methyl]-2-ethyl-7-methyl-5-(morpholin-4-yl)imidazo[1,2-b]pyridazine;
(23) 3-[(2'-Carboxybiphen-4-yl)methyl]-2-ethyl-7-methoxy-5-methylimidazo[1,2-b]pyridazine;
(24) 3-[(2'-Carboxybiphen-4-yl)methyl]-2-ethyl-5-hydroxymethyl-7-methylimidazo[1,2-b]pyridazine;
(25) 5-Carboxy-3-[(2'-carboxybiphen-4-yl)methyl]-2-ethyl-7-methylimidazo[1,2-b]pyridazine;
(26) 5-Carbomethoxy-3-[(2'-carboxybiphen-4-yl)methyl]-2-ethyl-7-methylimidazo[1,2-b]pyridazine;
(27) 3-[(2'-Carboxybiphen-4-yl)methyl]-2-ethyl-7-methyl-5-phenylimidazo[1,2-b]pyridazine;
(28) 3-[(2'-Carboxybiphen-4-yl)methyl]-5-(2-chloro)phenyl-2-ethyl-7-methylimidazo[1,2-b]pyridazine;
(29) 3-[(2'-Carboxybiphen-4-yl)methyl]-5-(4-chloro)phenyl-2-ethyl-7-methylimidazo[1,2-b]pyridazine;
(30) 3-[(2'-Carboxybiphen-4-yl)methyl]-2-ethyl-7-methyl-5-(2-trifluoromethyl)phenylimidazo[1,2-b]pyridazine;
(31) 6-Amino-3-[(2'-carboxybiphen-4-yl)methyl]-5,7-dimethyl-2-ethylimidazo[1,2-b]pyridazine;
(32) 3-[(2'-Carboxybiphen-4-yl)methyl]-5,7-dimethyl-2-ethyl-6-ethylaminoimidazo[1,2-b]pyridazine;
(33) 3-[(2'-Carboxybiphen-4-yl)methyl]-5,7-dimethyl-2-ethyl-6-fluoroimidazo[1,2-b]pyridazine;
(34) 3-[(2'-Carboxybiphen-4-yl)methyl]-5,7-dimethyl-2-(2,2,2-trifluoroethylimidazo[1,2-b]pyridazine;
(35) 3-[(2'-Carboxybiphen-4-yl)methyl]-5,7-dimethyl-2-(pentafluoroethylimidazo[1,2-b]pyridazine;
(36) 3-[(2'-Carboxybiphen-4-yl)methyl]-5,7-dimethyl-2-(3,3,3-trifluoroethylimidazo[1,2-b]pyridazine;
(37) 3-[(2'-Carboxybiphen-4-yl)methyl]-5,7-dimethyl-2-(4,4,4-trifluorobutylimidazo[1,2-b]pyridazine;
(38) 3-[(2'-Carboxybiphen-4-yl)methyl]-5,7-dimethyl-2-(2,2-difluoropropylimidazo[1,2-b]pyridazine;
(39) 3-[(2'-Carboxybiphen-4-yl)methyl]-5,7-dimethyl-2-trans-2-butenylimidazo[1,2-b]pyridazine;
(40) 3-[(2'-Carboxybiphen-4-yl)methyl]-5,7-dimethyl-2-trans-1-propenylimidazo[1,2-b]pyridazine;
(41) 2-Allyl-3-[(2'-carboxybiphen-4-yl)methyl]-5,7-dimethylimidazo[1,2-b]pyridazine;
(42) 3-[(2'-Carboxybiphen-4-yl)methyl]-5,7-dimethyl-2-(2-propynyl)imidazo[1,2-b]pyridazine;
(43) 2-(2-Butynyl)-3-[(2'-carboxybiphen-4-yl)methyl]-5,7-dimethylimidazo[1,2-b]pyridazine;
(44) 3-[(2'-Carboxybiphen-4-yl)methyl]-5,7-dimethyl-2-(4,4,4-trifluoro-2-butynyl)imidazo[1,2-b]pyridazine;
(45) 3-[(2'-Carboxybiphen-4-yl)methyl]-5,7-dimethyl-2-(2,2,2-trifluoroethoxy)imidazo[1,2-b]pyridazine;
(46) 2-Butyl-3-[(2'-(tetrazol-5-yl)biphen-4-yl)methyl]imidazo[1,2-b]pyridazine;
(47) 2-Propyl-3-[(2'-(tetrazol-5-yl)biphen-4-yl)methyl]imidazo[1,2-b]pyridazine;
(48) 2-Ethyl-3-[(2'-(tetrazol-5-yl)biphen-4-yl)methyl]imidazo[1,2-b]pyridazine;
(49) 2-Isopropyl-3-[(2'-(tetrazol-5-yl)biphen-4-yl)methyl]imidazo[1,2-b]pyridazine;
(50) 2-Cyclopropyl-3-[(2'-(tetrazol-5-yl)biphen-4-yl)methyl]imidazo[1,2-b]pyridazine;
(51) 7-Methyl-2-propyl-3-[(2'-(tetrazol-5-yl)biphen-4-yl)methyl]imidazo[1,2-b]pyridazine;
(52) 7-Ethyl-2-propyl-3-[(2'-(tetrazol-5-yl)biphen-4-yl)methyl]imidazo[1,2-b]pyridazine;
(53) 2-Ethyl-7-methyl-3-[(2'-(tetrazol-5-yl)biphen-4-yl)methyl]imidazo[1,2-b]pyridazine;
(54) 2,7-Diethyl-3-[(2'-(tetrazol-5-yl)biphen-4-yl)methyl]imidazo[1,2-b]pyridazine;
(55) 5,7-Dimethyl-2-propyl-3-[(2'-(tetrazol-5-yl)biphen-4-yl)methyl]imidazo[1,2-b]pyridazine;
(56) 5,7-Dimethyl-2-ethyl-3-[(2'-(tetrazol-5-yl)biphen-4-yl)methyl]imidazo[1,2-b]pyridazine;
(57) 2-Cyclopropyl-5,7-dimethyl-3-[(2'-(tetrazol-5-yl)biphen-4-yl)methyl]imidazo[1,2-b]pyridazine;
(58) 5-Ethyl-7-methyl-2-propyl-3-[(2'-(tetrazol-5-yl)biphen-4-yl)methyl]imidazo[1,2-b]pyridazine;
(59) 2,5-Diethyl-7-methyl-3-[(2'-(tetrazol-5-yl)biphen-4-yl)methyl]imidazo[1,2-b]pyridazine;
(60) 2-Ethyl-7-methyl-5-methylamino-3-[(2'-(tetrazol-5-yl)biphen-4-yl)methyl]imidazo[1,2-b]pyridazine;
(61) 5-Amino-7-methyl-2-ethyl-3-[(2'-(tetrazol-5-yl)biphen-4-yl)methyl]imidazo[1,2-b]pyridazine;
(62) 2-Ethyl-5-methylamino-7-trifluoromethyl-3-[(2'-(tetrazol-5-yl)biphen-4-yl)methyl]imidazo[1,2-b]pyridazine;
(63) 2-Ethyl-5-methyl-7-methylamino-3-[(2'-(tetrazol-5-yl)biphen-4-yl)methyl]imidazo[1,2-b]pyridazine;
(64) 7-Dimethylamino-2-ethyl-5-methyl-3-[(2'-(tetrazol-5-yl)biphen-4-yl)methyl]imidazo[1,2-b]pyridazine;
(65) 2-Ethyl-5-methyl-7-phenylamino-3-[(2'-(tetrazol-5-yl)biphen-4-yl)methyl]imidazo[1,2-b]pyridazine;
(66) 2-Ethyl-5-methyl-7-(morpholin-4-yl)-3-[(2'-(tetrazol-5-yl)biphen-4-yl)methyl]imidazo[1,2-b]pyridazine;
(67) 2-Ethyl-7-methyl-5-(morpholin-4-yl)-3-[(2'-(tetrazol-5-yl)biphen-4-yl)methyl]imidazo[1,2-b]pyridazine;
(68) 2-Ethyl-7-methoxy-5-methyl-3-[(2'-(tetrazol-5-yl)biphen-4-yl)methyl]imidazo[1,2-b]pyridazine;
(69) 2-Ethyl-5-hydroxymethyl-7-methyl-3-[(2'-(tetrazol-5-yl)biphen-4-yl)methyl]imidazo[1,2-b]pyridazine;
(70) 5-Carboxy-2-ethyl-7-methyl-3-[(2'-(tetrazol-5-yl)biphen-4-yl)methyl]imidazo[1,2-b]pyridazine;

(71) 5-Carbomethoxy-2-ethyl-7-methyl-3-[(2'-(tetrazol-5-yl)biphen-4-yl)methyl]imidazo[1,2-b]pyridazine;
(72) 2-Ethyl-7-methyl-5-phenyl-3-[(2'-(tetrazol-5-yl)biphen-4-yl)methyl]imidazo[1,2-b]pyridazine;
(73) 5-(2-Chloro)phenyl-2-ethyl-7-methyl-3-[(2'-(tetrazol-5-yl)biphen-4-yl)methyl]imidazo[1,2-b]pyridazine;
(74) 5-(4-Chloro)phenyl-2-ethyl-7-methyl-3-[(2'-(tetrazol-5-yl)biphen-4-yl)methyl]imidazo [1,2-b]pyridazine;
(75) 2-Ethyl-7-methyl-5-(2-trifluoromethyl)phenyl-3-[(2'-(tetrazol-5-yl)biphen-4-yl)methyl]imidazo[1,2-b]pyridazine;
(76) 6-Amino-5,7-dimethyl-2-ethyl-3-[(2'-(tetrazol-5-yl)biphen-4-yl)methyl]imidazo[1,2-b]pyridazine;
(77) 5,7-Dimethyl-2-ethyl-6-ethylamino-3-[(2'-(tetrazol-5-yl)biphen-4-yl)methyl]imidazo[1,2-b]pyridazine;
(78) 5,7-Dimethyl-2-ethyl-6-fluoro-3-[(2'-(tetrazol-5-yl)biphen-4-yl)methyl]imidazo[1,2-b]pyridazine;
(79) 5,7-Dimethyl-3-[(2'-(tetrazol-5-yl)biphen-4-yl)methyl]-2-(2,2,2-trifluoroethylimidazo[1,2-b]pyridazine;
(80) 5,7-Dimethyl-2-(pentafluoroethyl-3-[(2'-(tetrazol-5-yl)biphen-4-yl)methyl]imidazo[1,2-b]pyridazine;
(81) 5,7-Dimethyl-3-[(2'-(tetrazol-5-yl)biphen-4-yl)methyl]-2-(3,3,3-trifluoropropylimidazo[1,2-b]pyridazine;
(82) 5,7-Dimethyl-3-[(2'-(tetrazol-5-yl)biphen-4-yl)methyl]-2-(4,4,4-trifluorobutylimidazo[1,2-b]pyridazine;
(83) 5,7-Dimethyl-2-(2,2-difluoropropyl-3-[(2'-(tetrazol-5-yl)biphen-4-yl)methyl]imidazo[1,2-b]pyridazine;
(84) 5,7-Dimethyl-2-trans-2-butenyl-3-[(2'-(tetrazol-5-yl)biphen-4-yl)methyl]imidazo[1,2-b]pyridazine;
(85) 5,7-Dimethyl-3-[(2'-(tetrazol-5-yl)biphen-4-yl)methyl]-2-trans-1-propenylimidazo[1,2-b]pyridazine;
(86) 2-Allyl-5,7-dimethyl-3-[(2'-(tetrazol-5-yl)biphen-4-yl)methyl]imidazo[1,2-b]pyridazine;
(87) 5,7-Dimethyl-2-(2-propynyl)-3-[(2'-(tetrazol-5-yl)biphen-4-yl)methyl]imidazo[1,2-b]pyridazine;
(88) 2-(2-Butynyl)-5,7-dimethyl-3-[(2'-(tetrazol-5-yl)biphen-4-yl)methyl]imidazo[1,2-b]pyridazine;
(89) 5,7-Dimethyl-3-[(2'-(tetrazol-5-yl)biphen-4-yl)methyl]-2-(4,4,4-trifluoro-2-butynyl)imidazo[1,2-b]pyridazine;
(90) 5,7-Dimethyl-3-[(2'-(tetrazol-5-yl)biphen-4-yl)methyl]-2-(2,2,2-trifluoroethoxy)imidazo[1,2-b]-pyridazine;
(91) 5,7-Dimethyl-2-ethyl-3-[(2'-(N-((phenylsulfonyl)carboxamido)biphen-4-yl)methyl]imidazo[1,2-b]pyridazine;
(92) 5,7-Dimethyl-2-ethyl-3-[(2'-(N-((methylsulfonyl)carboxamido)biphen-4-yl)methyl]imidazo[1,2-b]pyridazine;
(93) 5,7-Dimethyl-2-ethyl-3-[(2'-(N-((trifluoromethylsulfonyl)carboxamido)biphen-4-yl)methyl-]imidazo[1,2-b]pyridazine;
(94) 3-[(2'-(N-((2-Aminoethyl)sulfonyl)carboxamido)biphen-4-yl)methyl]-5,7-dimethyl-2-ethylimidazo[1,2-b]pyridazine;
(95) 5,7-Dimethyl-2-ethyl-3-[(2'-(N-((morpholin-4-yl)sulfonyl)carboxamido)biphen-4-yl)methyl-]imidazo[1,2-b]pyridazine;
(96) 5,7-Dimethyl-[(2'-(N-(N,N-dimethylaminosulfonyl)carboxamido)biphen-4-yl)methyl]-2-ethyl-3-imidazo[1,2-b]pyridazine;
(97) 3-[(2'-(N-(Cyclopentylsulfonyl)carboxamido)biphen-4-yl)methyl]-5,7-dimethyl-2-ethylimidazo[1,2-b]pyridazine;
(98) 5,7-Dimethyl-2-ethyl-3-[(2'-(N-(pyrimidin-2-yl)biphen-4-yl)methyl]imidazo[1,2-b]pyridazine;
(99) 5,7-Dimethyl-3-[(2'-(N-(4,6-dimethylpyrimidin-2-yl)sulfamido)biphen-4-yl)methyl]-2-ethylimidazo[1,2-b]pyridazine;
(100) 5,7-Dimethyl-2-ethyl-3-[(2'-(N-(triazin-2-yl)sulfamido)biphen-4-yl)methyl]imidazo[1,2-b]pyridazine;
(101) 5,7-Dimethyl-2-ethyl-3-[(2'-(N-(oxazol-2-yl)sulfamido)biphen-4-yl)methyl]imidazo[1,2-b]pyridazine;
(102) 3-[(2'-(N-(Acetyl)sulfonamido)biphen-4-yl)methyl]-5,7-dimethyl-2-ethylimidazo[1,2-b]pyridazine;
(103) 3-[(2'-(N-(Benzoyl)sulfonamido)biphen-4-yl)methyl]-5,7-dimethyl-2-ethylimidazo[1,2-b]pyridazine;
(104) 5,7-Dimethyl-2-ethyl-3-[(2'-(N-(4-nitrobenzoyl)-sulfamido)biphen-4-yl)methyl]imidazo[1,2-b]pyridazine;
(105) 3-[(2'-(N-(4-Chlorobenzoyl)sulfonamido)biphen-4-yl)methyl]-5,7-dimethyl-2-ethylimidazo[1,2-b]-pyridazine;
(106) 5,7-Dimethyl-2-ethyl-3-[(2'-(N((morpholin-4-yl)carbonyl)sulfamido)biphen-4-yl)methyl-]imidazo[1,2-b]pyridazine;
(107) 5,7-Dimethyl-2-ethyl-3-[(2'-(N-((piperazin-1-yl)carbonyl)sulfamido)biphen-4-yl)methyl-]imidazo[1,2-b]pyridazine;
(108) 5,7-Dimethyl-2-ethyl-3-[(2'-((N-(trifluoromethyl)-carbonyl)sulfamido)biphen-4-yl)methyl]imidazo[1,2-b]pyridazine;
(109) 3-[(2'-(N-((2-Carboxyethyl)carbonyl)sulfamido)-biphen-4-yl)methyl]-5,7-dimethyl-2-ethylimidazo[1,2-b]pyridazine;
(110) 5,7-Dimethyl-3-[(2'-((N-(2-ethoxyethyl)carbonyl)-sulfamido)biphen-4-yl)methyl]-2-ethylimidazo[1,2-b]pyridazine;
(111) 5,7-Dimethyl-2-ethyl-3-[(2'-(N-((phenylsulfonyl)-carboxamido)methylbiphen-4-yl)methyl]imidazo[1,2-b]pyridazine;
(112) 5,7-Dimethyl-3-[(2'-(N-(4,6-dimethylpyrimidin-2-yl)sulfamido)methylbiphen-4-yl)methyl]-2-ethylimidazo[1,2-b]pyridazine;
(113) 5-Carboethoxy-2-cyclopropyl-7-methyl-3-[(2'-(tetrazol-5-yl)biphen-4-yl)methyl]imidazo[1,2-b]pyridazine;
(114) 5-Carboethoxy-7-methyl-2-propyl-3-[(2'-(tetrazol-5-yl)biphen-4-yl)methyl]imidazo[1,2-b]pyridazine;
(115) 3-[(2'-(N-(Benzoyl)sulfonamido)biphen-4-yl)methyl]-5-carboethoxy-2-cyclopropyl-7-methylimidazo[1,2-b]pyridazine; and
(116) 3-[(2'-(N-(Benzoyl)sulfonamido)biphen-4-yl)methyl]-5-carboethoxy-7-methyl-2-propylimidazo[1,2-b]pyridazine;
(117) 2-Cyclopropyl-5,7-dimethyl-3-[(2'-(N-(butoxycarbonyl)sulfonamido)biphen-4-yl)methyl]imidazo[1,2-b]pyridazine;
(118) 2-Cyclopropyl-5,7-dimethyl-3-[(2'-(N-(butoxycarbonyl)sulfonamido)-5'-isobutylbiphen-4-yl)methyl-]imidazo[1,2-b]pyridazine;
(119) 2-Cyclopropyl-5,7-dimethyl-3-[(2'-(N-(butoxycarbonyl)sulfonamido)-5'-propylbiphen-4-yl)methyl-]imidazo[1,2-b]pyridazine;
(120) 2-Cyclopropyl-5,7-dimethyl-3-[(2'-(N-(propoxycarbonyl)sulfonamido)-5'-isobutylbiphen-4-yl)methyl]imidazo[1,2-b]pyridazine;
(121) 2-Cyclopropyl-5,7-dimethyl-3-[(2'-(N-(cyclopropanecarbonyl)sulfonamido)biphen-4-yl)methyl-]imidazo[1,2-b]pyridazine;

(122) 2-Cyclopropyl-5,7-dimethyl-3-[(2'-(N-((R)-2,2-dimethylcyclopropane-1-carbonyl)sulfonamido)biphen-4-yl)methyl]imidazo[1,2-b]pyridazine;
(123) 2-Cyclopropyl-5,7-dimethyl-3-[(2'-(N-((S)-2,2-dimethylcyclopropane-1-carbonyl)sulfonamido)biphen-4-yl)methyl]imidazo[1,2-b]pyridazine;
(124) 2-Cyclopropyl-5,7-dimethyl-3-[(2'-(N-(cyano)sulfonamido)biphen-4-yl)methyl]imidazo[1,2-b]pyridazine;
(125) 2-Cyclopropyl-5,7-dimethyl-3-[(2'-(N-(2thiazolo)sulfonamido)biphen-4-yl)methyl]imidazo[1,2-b]pyridazine;
(126) N,N,7-trimethyl-2-cyclopropyl-3-[(2'-(tetrazol-5-yl)biphen-4-yl)methyl]imidazo[1,2-b]pyridazine-5-carboxamide;
(127) N,N-diethyl-2-cyclopropyl-7-methyl-3-[(2'-tetrazol-5-yl)biphen-4-yl)methyl]imidazo[1,2-b]pyridazine-5-carboxamide;
(128) N,N,5,7-tetramethyl-2-cyclopropyl-3-[(2'-(N-(cyclopropanecarbonyl)sulfonamido)biphen-4-yl)methyl]imidazo[1,2-b]pyridazine-5-carboxamide;
(129) N,N,5,7-tetramethyl-2-cyclopropyl-3-[(2'-(N-((R)-2,2-dimethylcyclopropane-1-carbonyl)sulfonamido)biphen-4-yl)methyl]imidazo[1,2-b]pyridazine-5-carboxamide;
(130) N,N,5,7-tetramethyl-2-cyclopropyl-3-[(2'-(N-((S)-2,2-dimethylcyclopropane-1-carbonyl)sulfonamido)biphen-4-yl)methyl]imidazo[1,2-b]pyridazine-5-carboxamide;
(131) N,N,5,7-tetramethyl-2-cyclopropyl-3-[(2'-(N-(cyano)sulfonamido)biphen-4-yl)methyl]imidazo[1,2-b]pyridazine-5-carboxamide;
(132) N,N,5,7-tetramethyl-2-cyclopropyl-3-[(2'-(N-(2-thiazolo)sulfonamido)biphen-4-yl)methyl]imidazo[1,2-b]pyridazine-5-carboxamide.

A third embodiment of the compounds of formula (I) are the compounds

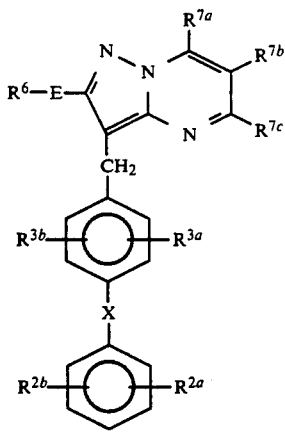

wherein:
$R^1$ is
  (a) —CO$_2$H,
  (b) —CO$_2$R$^{29}$,
  (c) —CONH—SO$_2$—R$^{20}$,
  (d) —CONHSO$_2$NR$^8$R$^8$,
  (e) —CONHOR$^5$,
  (f)

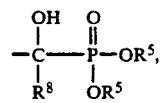

(g) —CN,
  (h) CONHNHSO$_2$CF$_3$,
  (i) CH$_2$SO$_2$NH-heteroaryl,
  (j) CH$_2$SO$_2$NHCOR$^{20}$,
  (k) CH$_2$CONHSO$_2$R$^{20}$,
  (l)

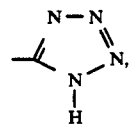

or
(m)

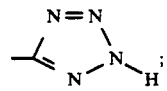

$R^{2a}$ and $R^{2b}$ are H, Br, I, F, Cl, CF$_3$ (C$_1$-C$_6$)-alkyl (C$_2$-C$_6$)-alkenyl, (C$_2$-C$_6$)-alkynyl, (C$_1$-C$_4$)-alkoxyl, or phenyl;

$R^{3a}$ and $R^{3b}$ are independently: Br, I, Cl, F, (C$_1$-C$_4$)-alkyl, (C$_2$-C$_4$)-alkenyl, (C$_2$-C$_4$)-alkynyl, (C$_1$-C$_4$)-alkoxyl, NO$_2$, CF$_3$, SO$_2$NR$^8$R$^8$, (C$_1$-C$_4$)-alkylthio, hydroxyl, or NR$^8$R$^8$;

E is a single bond, —O— or —S—;

$R^6$ is
  (a) (C$_1$-C$_5$)-alkyl unsubstituted or substituted with a substituent selected from the group consisting of: Cl, CF$_3$, CCl$_3$, —O—CH$_3$, —OC$_2$H$_5$, —S—CH$_3$, —S—C$_2$H$_5$ or phenyl;
  (b) (C$_2$-C$_5$)-alkenyl or (C$_2$-C$_5$)-alkynyl;
  (c) (C$_3$-C$_5$)-cycloalkyl;

$R^{7a}$, $R^{7b}$ and $R^{7c}$ are independently
  (a) H,
  (b) (C$_1$-C$_4$)-alkyl,
  (c) (C$_2$-C$_4$)-alkenyl,
  (d) —OH,
  (e) —CH$_2$OCOR$^4$,
  (f) —NH$_2$,
  (g)

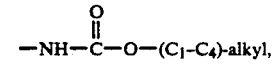

(h)

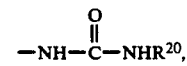

(i) —(C$_1$-C$_4$)-alkoxy,
  (j) —NH[(C$_1$-C$_4$)-alkyl],
  (k) —N[(C$_1$-C$_4$)-alkyl]$_2$,
  (l) Cl, F, or Br,
  (m) —CF$_3$,
  (n) —CO$_2$R$^4$,
  (o) —CH$_2$—OH, (p) 5 or 6 membered saturated heterocycle containing one nitrogen atom and optionally containing one other heteroatom selected from N, O, or S, such as pyrrolidine, morpholine, or piperazine;
(q) —CO-aryl as defined above,
(r) —S(O)$_n$—(C$_1$-C$_4$)-alkyl;
(s) —SO$_2$—NH—(C$_1$-C$_4$)-alkyl,
(t) —SO$_2$—NH-aryl,
(u) —NH—SO$_2$CH$_3$,
(v) aryl,
(w) heteroaryl,
(x) —N[CH$_2$CH$_2$]$_2$G,
(y) —CON[CH$_2$CH$_2$]$_2$G,
(z) —CON(R$^4$)$_2$
(aa)

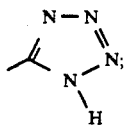

and,
X is —OCHR$^1$—, —R$^1$CHO—, —NR$^{15}$CHR$^1$— or —CHR$^1$NR$^{15}$—.

In a class of this embodiment are those compounds wherein:
R$^1$ is
(a) —CO$_2$H,
(b) —CO$_2$R$^{29}$,
(c) —CONH—SO$_2$—R$^{20}$,
(d) —CONHSO$_2$NR$^8$R$^8$,
(e) —CONHOR$^5$,
(f)

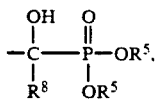

(g) —CN,
(h) CONHNHSO$_2$CF$_3$,
(i) CH$_2$SO$_2$NH-heteroaryl,
(j) CH$_2$SO$_2$NHCOR$^{20}$, or
(k) CH$_2$CONHSO$_2$R$^{20}$;
(l)

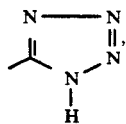

R$^{2a}$, R$^{2b}$, R$^{3a}$ and R$^{3b}$ are each H;
R$^6$ is n-propyl, n-butyl, methyl, ethyl, cyclopropyl, or —CH$_2$—S—CH$_3$;
R$^{7a}$ is —(C$_1$-C$_4$)-alkyl, aryl, heteroaryl, —(C$_1$-C$_4$)-perfluoroalkyl, —(C$_3$-C$_6$)-cycloalkyl;
R$^{7b}$ is —H, —F, —Cl, —(C$_1$-C$_4$)-alkyl, —(C$_1$-C$_4$)-perfluoroalkyl;
R$^{7c}$ is —(C$_1$-C$_4$)-alkyl, aryl, heteroaryl, —(C$_1$-C$_4$)-perfluoroalkyl, CON(R$^4$)$_2$, —(C$_3$-C$_6$)-cycloalkyl, CO$_2$R$^4$, 1H-tetrazol-5-yl, N[CH$_2$CH$_2$]$_2$NH, N[CH$_2$CH$_2$]$_2$NCOR$^{20}$, NHSO$_2$CF$_3$, SO$_2$NHCOR$^{20}$, or CON[(C$_1$-C$_2$)-alkyl]$_2$;
E is a single bond or —S—; and,
X is —OCHR$^1$— or —CHR$^1$—O—.

Exemplifying the foregoing class are the following compounds listed in the table below:

| # | R$^6$ | R$^{3b}$ | R$^{3a}$ | R$^{7c}$ | R$^1$ |
|---|---|---|---|---|---|
| 1 | cyPr | H | H | Me | —COOH |
| 2 | cyPr | H | H | Me | —COOMe |
| 3 | cyPr | H | H | Me | —CONHSO$_2$Ph |
| 4 | cyPr | H | H | Me | —CONHSO$_2$Me |
| 5 | cyPr | Cl | H | Me | —COOH |
| 6 | cyPr | Cl | H | Me | —COOMe |
| 7 | cyPr | Cl | H | Me | —CONHSO$_2$Ph |
| 8 | cyPr | Cl | H | Me | —CONHSO$_2$Me |
| 9 | cyPr | Cl | nPr | Me | —COOH |
| 10 | cyPr | Cl | nPr | Me | —COOMe |
| 11 | cyPr | Cl | nPr | Me | —CONHSO$_2$Ph |
| 12 | cyPr | Cl | nPr | Me | —CONHSO$_2$Me |
| 13 | cyPr | nPr | nPr | Me | —COOH |
| 14 | cyPr | nPr | nPr | Me | —COOMe |
| 15 | cyPr | nPr | nPr | Me | —CONHSO$_2$Ph |
| 16 | cyPr | nPr | nPr | Me | —CONHSO$_2$Me |
| 17 | cyPr | Cl | Cl | Me | —COOH |
| 18 | cyPr | Cl | Cl | Me | —COOMe |
| 19 | cyPr | Cl | Cl | Me | —CONHSO$_2$Ph |
| 20 | cyPr | Cl | Cl | Me | —CONHSO$_2$Me |
| 21 | Et | H | H | Me | —COOH |
| 22 | Et | H | H | Me | —COOMe |
| 23 | Et | H | H | Me | —CONHSO$_2$Ph |
| 24 | Et | H | H | Me | —CONHSO$_2$Me |
| 25 | Et | Cl | H | Me | —COOH |
| 26 | Et | Cl | H | Me | —COOMe |
| 27 | Et | Cl | H | Me | —CONHSO$_2$Ph |
| 28 | Et | Cl | H | Me | —CONHSO$_2$Me |
| 29 | Et | Cl | nPr | Me | —COOH |
| 30 | Et | Cl | nPr | Me | —COOMe |
| 31 | Et | Cl | nPr | Me | —CONHSO$_2$Ph |
| 32 | Et | Cl | nPr | Me | —CONHSO$_2$Me |
| 33 | Et | nPr | nPr | Me | —COOH |
| 34 | Et | nPr | nPr | Me | —COOMe |
| 35 | Et | nPr | nPr | Me | —CONHSO$_2$Ph |
| 36 | Et | nPr | nPr | Me | —CONHSO$_2$Me |
| 37 | Et | Cl | Cl | Me | —COOH |
| 38 | Et | Cl | Cl | Me | —COOMe |
| 39 | Et | Cl | Cl | Me | —CONHSO$_2$Ph |
| 40 | Et | Cl | Cl | Me | —CONHSO$_2$Me |
| 41 | Et | H | H | Me | —COOH |
| 42 | Et | H | H | Me | —COOMe |
| 43 | Et | H | H | Me | —CONHSO$_2$Ph |
| 44 | Et | H | H | Me | —CONHSO$_2$Me |
| 45 | Et | Cl | H | Me | —COOH |
| 46 | Et | Cl | H | Me | —COOMe |
| 47 | Et | Cl | H | Me | —CONHSO$_2$Ph |
| 48 | Et | Cl | H | Me | —CONHSO$_2$Me |
| 49 | Et | Cl | nPr | Me | —COOH |
| 50 | Et | Cl | nPr | Me | —COOMe |
| 51 | Et | Cl | nPr | Me | —CONHSO$_2$Ph |
| 52 | Et | Cl | nPr | Me | —CONHSO$_2$Me |
| 53 | Et | nPr | nPr | Me | —COOH |
| 54 | Et | nPr | nPr | Me | —COOMe |
| 55 | Et | nPr | nPr | Me | —CONHSO$_2$Ph |
| 56 | Et | nPr | nPr | Me | —CONHSO$_2$Me |

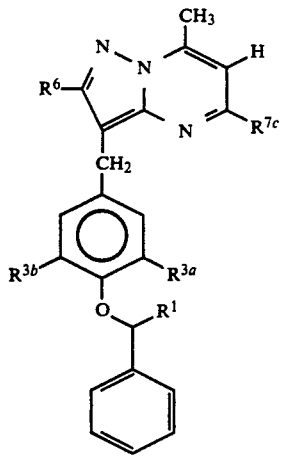

| # | R6 | R3b | R3a | R7c | R1 |
|---|---|---|---|---|---|
| 57 | Et | Cl | Cl | Me | —COOH |
| 58 | Et | Cl | Cl | Me | —COOMe |
| 59 | Et | Cl | Cl | Me | —CONHSO$_2$Ph |
| 60 | Et | Cl | Cl | Me | —CONHSO$_2$Me |
| 61 | nPr | H | H | Me | —COOH |
| 62 | nPr | H | H | Me | —COOMe |
| 63 | nPr | H | H | Me | —CONHSO$_2$Ph |
| 64 | nPr | H | H | Me | —CONHSO$_2$Me |
| 65 | nPr | Cl | H | Me | —COOH |
| 66 | nPr | Cl | H | Me | —COOMe |
| 67 | nPr | Cl | H | Me | —CONHSO$_2$Ph |
| 68 | nPr | Cl | H | Me | —CONHSO$_2$Me |
| 69 | nPr | Cl | nPr | Me | —COOH |
| 70 | nPr | Cl | nPr | Me | —COOMe |
| 71 | nPr | Cl | nPr | Me | —CONHSO$_2$Ph |
| 72 | nPr | Cl | nPr | Me | —CONHSO$_2$Me |
| 73 | nPr | nPr | nPr | Me | —COOH |
| 74 | nPr | nPr | nPr | Me | —COOMe |
| 75 | nPr | nPr | nPr | Me | —CONHSO$_2$Ph |
| 76 | nPr | nPr | nPr | Me | —CONHSO$_2$Me |
| 77 | nPr | Cl | Cl | Me | —COOH |
| 78 | nPr | Cl | Cl | Me | —COOMe |
| 79 | nPr | Cl | Cl | Me | —CONHSO$_2$Ph |
| 80 | nPr | Cl | Cl | Me | —CONHSO$_2$Me |
| 81 | nPr | H | H | Me | —COOH |
| 82 | nPr | H | H | Me | —COOMe |
| 83 | nPr | H | H | Me | —CONHSO$_2$Ph |
| 84 | nPr | H | H | Me | —CONHSO$_2$Me |
| 85 | nPr | Cl | H | Me | —COOH |
| 86 | nPr | Cl | H | Me | —COOMe |
| 87 | nPr | Cl | H | Me | —CONHSO$_2$Ph |
| 88 | nPr | Cl | H | Me | —CONHSO$_2$Me |
| 89 | nPr | Cl | nPr | Me | —COOH |
| 90 | nPr | Cl | nPr | Me | —COOMe |
| 91 | nPr | Cl | nPr | Me | —CONHSO$_2$Ph |
| 92 | nPr | Cl | nPr | Me | —CONHSO$_2$Me |
| 93 | nPr | nPr | nPr | Me | —COOH |
| 94 | nPr | nPr | nPr | Me | —COOMe |
| 95 | nPr | nPr | nPr | Me | —CONHSO$_2$Ph |
| 96 | nPr | nPr | nPr | Me | —CONHSO$_2$Me |
| 97 | nPr | Cl | Cl | Me | —COOH |
| 98 | nPr | Cl | Cl | Me | —COOMe |
| 99 | nPr | Cl | Cl | Me | —CONHSO$_2$Ph |
| 100 | nPr | Cl | Cl | Me | —CONHSO$_2$Me |

A fourth embodiment of the compounds of formula (I) are those compounds wherein:

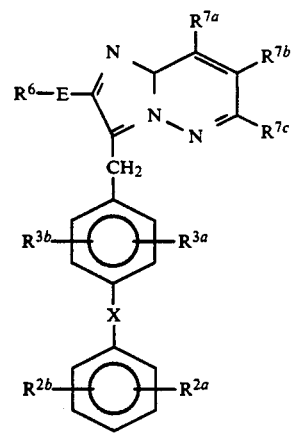

wherein:

$R^1$ is
- (a) —CO$_2$H,
- (b) —CO$_2$R$^{29}$,
- (c) —CONH—SO$_2$—R$^{20}$,
- (d) —CONHSO$_2$NR$^8$R$^8$,
- (e) —CONHOR$^5$,
- (f)

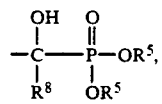

- (g) —CN,
- (h) CONHNHSO$_2$CF$_3$,
- (i) CH$_2$SO$_2$NH-heteroaryl,
- (j) CH$_2$SO$_2$NHCOR$^{20}$, or
- (k) CH$_2$CONHSO$_2$R$^{20}$;
- (l)

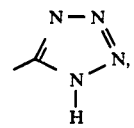

or
- (m)

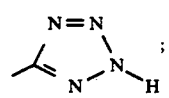

$R^{2a}$ and $R^{2b}$ are H, Br, I, F, Cl, CF$_3$ (C$_1$–C$_6$)-alkyl (C$_2$–C$_6$)-alkenyl, (C$_2$–C$_6$)-alkynyl, (C$_1$–C$_4$)-alkoxyl, or phenyl;

$R^{3a}$ and $R^{3b}$ are independently: Br, I, Cl, F, (C$_1$–C$_4$)-alkyl, (C$_2$–C$_4$)-alkenyl, (C$_2$–C$_4$)-alkynyl, (C$_1$–C$_4$)-alkoxyl, NO$_2$, CF$_3$, SO$_2$NR$^8$R$^8$, (C$_1$–C$_4$)-alkylthio, hydroxyl, or NR$^8$R$^8$;

E is a single bond, —O— or —S—;

$R^6$ is
- (a) (C$_1$–C$_5$)-alkyl unsubstituted or substituted with a substituent selected from the group consisting of: Cl, CF$_3$, CCl$_3$, —O—CH$_3$, —OC$_2$H$_5$, —S—CH$_3$, —S—C$_2$H$_5$ or phenyl;

(b) (C₂-C₅)-alkenyl or (C₂-C₅)-alkynyl;
(c) (C₃-C₅)-cycloalkyl;
R⁷ᵃ, R⁷ᵇ and R⁷ᶜ are independently
(a) H,
(b) (C₁-C₄)-alkyl,
(c) (C₂-C₄)-alkenyl,
(d) —OH,
(e) —CH₂OCOR⁴,
(f) —NH₂,
(g)

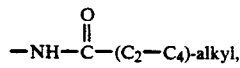
—NH—C(=O)—(C₂—C₄)-alkyl, (h)

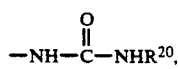
—NH—C(=O)—NHR²⁰, (i) —(C₁-C₄)-alkoxy,
(j) —NH[(C₁-C₄)-alkyl],
(k) —N[(C₁-C₄)-alkyl]₂,
(l) Cl, F, or Br,
(m) —CF₃,
(n) —CO₂R⁴,
(o) —CH₂—OH,
(p) 5 or 6 membered saturated heterocycle containing one nitrogen atom and optionally containing one other heteroatom selected from N, O, or S, such as pyrrolidine, morpholine, or piperazine;
(q) —CO-aryl as defined above,
(r) —S(O)ₙ—(C₁-C₄)-alkyl;
(s) —SO₂—NH—(C₁-C₄)-alkyl,
(t) —SO₂-NH-aryl,
(u) —NH—SO₂CH₃,
(v) aryl,
(w) heteroaryl, or
(x) —N[CH₂CH₂]₂G,
(y) —CON[CH₂CH₂]₂G,
(z) —CON(R⁴)₂,
(aa)

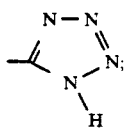

and,
X is —OCHR¹—, —R¹CHO—, NR¹⁵CHR¹—, or —CHR¹NR¹⁵—.

In a class of this embodiment are those compounds wherein:
R¹ is
(a) —CO₂H,
(b) —CO₂R²⁹,
(c) —CONH—SO₂—R²⁰,
(d) —CONHSO₂NR⁸R⁸,
(e) —CONHOR⁵,
(f)

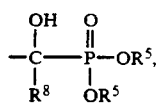

(g) —CN,
(h) CONHNHSO₂CF₃,
(i) CH₂SO₂NH-heteroaryl,
(j) CH₂SO₂NHCOR²⁰,
(k) CH₂CONHSO₂R²⁰, or
(l)

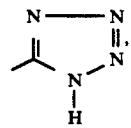

R²ᵃ, R²ᵇ, R³ᵃ and R³ᵇ are each H;
R⁶ is n-propyl, n-butyl, methyl, ethyl, cyclopropyl, or —CH₂—S—CH₃;
R⁷ᵃ is —(C₁-C₄)-alkyl, aryl, heteroaryl, —(C₁-C₄)-perfluoroalkyl, —(C₃-C₆)-cycloalkyl;
R⁷ᵇ is —H, —F, —Cl, —(C₁-C₄)-alkyl, —(C₁-C₄)-perfluoroalkyl;
R⁷ᶜ is —(C₁-C₄)-alkyl, aryl, heteroaryl, —(C₁-C₄)-perfluoroalkyl, —(C₃-C₆)-cycloalkyl, CO₂R⁴, 1H-tetrazol-5-yl, N[CH₂CH₂]₂NH, N[CH₂CH₂]₂NCOR²⁰, NHSO₂CF₃, SO₂NHCOR²⁰, or CON[(C₁-C₂)-alkyl]₂;
E is a single bond or —S—; and,
X is —OCHR¹— or —CHR¹—O—.

Exemplifying the foregoing class are the following compounds listed in the table below:

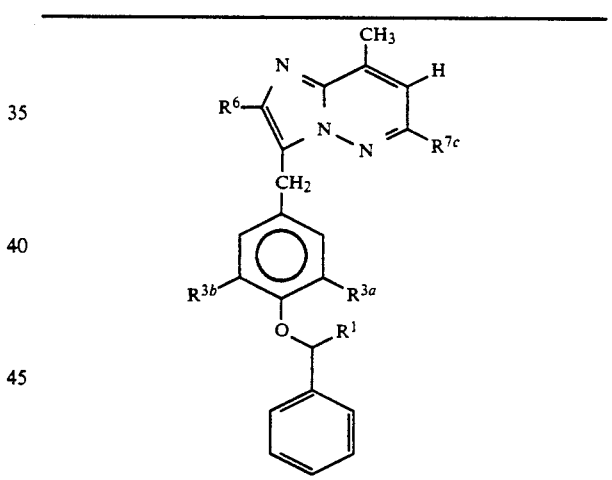

| # | R⁶ | R³ᵇ | R³ᵃ | R⁷ᶜ | R¹ |
|---|-----|-----|-----|-----|-----|
| 1 | cyPr | H | H | Me | —COOH |
| 2 | cyPr | H | H | Me | —COOMe |
| 3 | cyPr | H | H | Me | —CONHSO₂Ph |
| 4 | cyPr | H | H | Me | —CONHSO₂Me |
| 5 | cyPr | Cl | H | Me | —COOH |
| 6 | cyPr | Cl | H | Me | —COOMe |
| 7 | cyPr | Cl | H | Me | —CONHSO₂Ph |
| 8 | cyPr | Cl | H | Me | —CONHSO₂Me |
| 9 | cyPr | Cl | nPr | Me | —COOH |
| 10 | cyPr | Cl | nPr | Me | —COOMe |
| 11 | cyPr | Cl | nPr | Me | —CONHSO₂Ph |
| 12 | cyPr | Cl | nPr | Me | —CONHSO₂Me |
| 13 | cyPr | nPr | nPr | Me | —COOH |
| 14 | cyPr | nPr | nPr | Me | —COOMe |
| 15 | cyPr | nPr | nPr | Me | —CONHSO₂Ph |
| 16 | cyPr | nPr | nPr | Me | —CONHSO₂Me |
| 17 | cyPr | Cl | Cl | Me | —COOH |
| 18 | cyPr | Cl | Cl | Me | —COOMe |
| 19 | cyPr | Cl | Cl | Me | —CONHSO₂Ph |
| 20 | cyPr | Cl | Cl | Me | —CONHSO₂Me |
| 21 | Et | H | H | Me | —COOH |
| 22 | Et | H | H | Me | —COOMe |

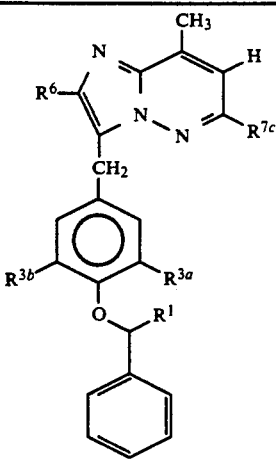

| # | R⁶ | R³ᵇ | R³ᵃ | R⁷ᶜ | R¹ |
|---|----|-----|-----|-----|-----|
| 23 | Et | H | H | Me | —CONHSO₂Ph |
| 24 | Et | H | H | Me | —CONHSO₂Me |
| 25 | Et | Cl | H | Me | —COOH |
| 26 | Et | Cl | H | Me | —COOMe |
| 27 | Et | Cl | H | Me | —CONHSO₂Ph |
| 28 | Et | Cl | H | Me | —CONHSO₂Me |
| 29 | Et | Cl | nPr | Me | —COOH |
| 30 | Et | Cl | nPr | Me | —COOMe |
| 31 | Et | Cl | nPr | Me | —CONHSO₂Ph |
| 32 | Et | Cl | nPr | Me | —CONHSO₂Me |
| 33 | Et | nPr | nPr | Me | —COOH |
| 34 | Et | nPr | nPr | Me | —COOMe |
| 35 | Et | nPr | nPr | Me | —CONHSO₂Ph |
| 36 | Et | nPr | nPr | Me | —CONHSO₂Me |
| 37 | Et | Cl | Cl | Me | —COOH |
| 38 | Et | Cl | Cl | Me | —COOMe |
| 39 | Et | Cl | Cl | Me | —CONHSO₂Ph |
| 40 | Et | Cl | Cl | Me | —CONHSO₂Me |
| 41 | Et | H | H | Me | —COOH |
| 42 | Et | H | H | Me | —COOMe |
| 43 | Et | H | H | Me | —CONHSO₂Ph |
| 44 | Et | H | H | Me | —CONHSO₂Me |
| 45 | Et | Cl | H | Me | —COOH |
| 46 | Et | Cl | H | Me | —COOMe |
| 47 | Et | Cl | H | Me | —CONHSO₂Ph |
| 48 | Et | Cl | H | Me | —CONHSO₂Me |
| 49 | Et | Cl | nPr | Me | —COOH |
| 50 | Et | Cl | nPr | Me | —COOMe |
| 51 | Et | Cl | nPr | Me | —CONHSO₂Ph |
| 52 | Et | Cl | nPr | Me | —CONHSO₂Me |
| 53 | Et | nPr | nPr | Me | —COOH |
| 54 | Et | nPr | nPr | Me | —COOMe |
| 55 | Et | nPr | nPr | Me | —CONHSO₂Ph |
| 56 | Et | nPr | nPr | Me | —CONHSO₂Me |
| 57 | Et | Cl | Cl | Me | —COOH |
| 58 | Et | Cl | Cl | Me | —COOMe |
| 59 | Et | Cl | Cl | Me | —CONHSO₂Ph |
| 60 | Et | Cl | Cl | Me | —CONHSO₂Me |
| 61 | nPr | H | H | Me | —COOH |
| 62 | nPr | H | H | Me | —COOMe |
| 63 | nPr | H | H | Me | —CONHSO₂Ph |
| 64 | nPr | H | H | Me | —CONHSO₂Me |
| 65 | nPr | Cl | H | Me | —COOH |
| 66 | nPr | Cl | H | Me | —COOMe |
| 67 | nPr | Cl | H | Me | —CONHSO₂Ph |
| 68 | nPr | Cl | H | Me | —CONHSO₂Me |
| 69 | nPr | Cl | nPr | Me | —COOH |
| 70 | nPr | Cl | nPr | Me | —COOMe |
| 71 | nPr | Cl | nPr | Me | —CONHSO₂Ph |
| 72 | nPr | Cl | nPr | Me | —CONHSO₂Me |
| 73 | nPr | nPr | nPr | Me | —COOH |
| 74 | nPr | nPr | nPr | Me | —COOMe |
| 75 | nPr | nPr | nPr | Me | —CONHSO₂Ph |
| 76 | nPr | nPr | nPr | Me | —CONHSO₂Me |
| 77 | nPr | Cl | Cl | Me | —COOH |
| 78 | nPr | Cl | Cl | Me | —COOMe |
| 79 | nPr | Cl | Cl | Me | —CONHSO₂Ph |
| 80 | nPr | Cl | Cl | Me | —CONHSO₂Me |
| 81 | nPr | H | H | Me | —COOH |
| 82 | nPr | H | H | Me | —COOMe |
| 83 | nPr | H | H | Me | —CONHSO₂Ph |
| 84 | nPr | H | H | Me | —CONHSO₂Me |
| 85 | nPr | Cl | H | Me | —COOH |
| 86 | nPr | Cl | H | Me | —COOMe |
| 87 | nPr | Cl | H | Me | —CONHSO₂Ph |
| 88 | nPr | Cl | H | Me | —CONHSO₂Me |
| 89 | nPr | Cl | nPr | Me | —COOH |
| 90 | nPr | Cl | nPr | Me | —COOMe |
| 91 | nPr | Cl | nPr | Me | —CONHSO₂Ph |
| 92 | nPr | Cl | nPr | Me | —CONHSO₂Me |
| 93 | nPr | nPr | nPr | Me | —COOH |
| 94 | nPr | nPr | nPr | Me | —COOMe |
| 95 | nPr | nPr | nPr | Me | —CONHSO₂Ph |
| 96 | nPr | nPr | nPr | Me | —CONHSO₂Me |
| 97 | nPr | Cl | Cl | Me | —COOH |
| 98 | nPr | Cl | Cl | Me | —COOMe |
| 99 | nPr | Cl | Cl | Me | —CONHSO₂Ph |
| 100 | nPr | Cl | Cl | Me | —CONHSO₂Me |

The alkyl substitutents recited above denote straight and branched chain hydrocarbons of the length specified such as methyl, ethyl, isopropyl, isobutyl, neopentyl, isopentyl, etc.

The alkenyl and alkynyl substituents denote alkyl groups as described above which are modified so that each contains a carbon to carbon double bond or triple bond, respectively, such as vinyl, allyl and 2-butenyl.

Cycloalkyl denotes rings composed of 3 to 8 methylene groups, each which may be substituted or unsubstituted with other hydrocarbon substituents, and include for example cyclopropyl, cyclopentyl, cyclohexyl and 4-methylcyclohexyl.

The alkoxy substituent represents an alkyl group as described above attached through an oxygen bridge.

The aryl substituent recited above represents phenyl or naphthyl.

The heteroaryl substituent recited above represents any 5- or 6-membered aromatic ring containing from one to three heteroatoms selected from the group consisting of nitrogen, oxygen, and sulfur, for example, pyridyl, thienyl, furyl, imidazolyl, and thiazolyl.

TABLE OF ABBREVIATIONS USED

| Reagents: | |
|---|---|
| NBS | N-bromosuccinimide |
| AIBN | Azo(bis)isobutyronitrile |
| DDQ | Dichlorodicyanoquinone |
| Ac₂O | acetic anhydride |
| TEA | triethylamine |

TABLE OF ABBREVIATIONS USED-continued

| | |
|---|---|
| DMAP | 4-dimethylaminopyridine |
| PPh3 | triphenylphosphine |
| TFA | trifluroacetic acid |
| TMS-Cl | trimethylsilyl chloride |
| Im | imidazole |
| AcSK | potassium thioacetate |
| p-TsOH | p-toluenesulfonic acid |
| Solvents: | |
| DMF | dimethylformamide |
| HOAc (AcOH) | acetic acid |
| EtOAc (EtAc) | ethyl acetate |
| Hex | hexane |
| THF | tetrahydrofuran |
| DMSO | dimethylsulfoxide |
| MeOH | methanol |
| iPrOH | isopropanol |
| Others: | |
| rt | room temperature |
| TBDMS | t-butyldimethylsilyl |
| OTf | $OSO_2CF_3$ |
| OTs | $OSO_2$—(4-methyl)phenyl |
| OMs | $OSO_2CH_3$ |
| Ph | phenyl |
| FAB-MS (FABMS) | Fast atom bombardment mass spectroscopy |
| NOE | Nuclear Overhauser Effect |
| $SiO_2$ | silica gel |
| trityl | triphenylmethyl |

Processes and methods for preparing the compounds of the invention are illustrated in the following reaction Schemes.

Pyrazolo[1,5-a]pyrimidines such as 5 are readily synthesized as shown in Schemes 1, 2, and 4. In Scheme 1, cyanoacetic acid is doubly deprotonated with two equivalents of n-butyllithium and the dianion is quenched with an $R^6$ acyl chloride. Upon acidification, the product decarboxylates to give the β-ketonitrile 1.[1] This material may then be alkylated with the desired sidechain with NaH, DMSO, and an alkyl halide 2 to give 3. Condensation of β-ketonitrile 3 with hydrazine in refluxing ethanol gives aminopyrazole 4 (not usually isolated) and then with an appropriate dicarbonyl (or dicarbonyl equivalent) compound gives pyrazolo[1,5-a]pyrimidine 5.[2]

Scheme 2 provides an additional route to biaryl A-II antagonists such as 12. Alkylation of 1 with a p-iodo benzyl group such as 6 provides the corresponding β-ketonitrile 7. Condensation of this material as in Scheme 1 provides the expected 3-p-iodobenzyl-pyrazolo[1,5-a]pyrimidine 10. Biaryl coupling of this material with the organotin reagent 11 (or the related diorganozinc reagent 13) gives the 3-biarylmethyl-pyrazolo[1,5-a]pyrimidine 12.[3]

Scheme 3 illustrates a preparation of a dicarbonyl equivalent used in Scheme 4. This material allows for the regiospecific introduction of groups at the 5-position of the pyrazolo[1,5-a]pyrimidines,[4] as illustrated in Scheme 4. Condensation of this material with the generalized 5-aminopyrazole 4 followed by peroxide oxidation gives the 5-(methylsulfonyl)pyrazolo[1,5-a]pyrimidine derivative 16. Conversion of this material to a nitrile can be accomplished using CuCN in pyridine or quinoline with heat or with NaCN in DMF or DMSO and heat.[5] The nitrile may then be readily converted to carboxylic esters[6], a carboxylic acid, ketones, or alkyls.

Scheme 5 provides a route to pyrazolo[1,5-a]pyrimidines where E is S. The bromomethyl group of 2 may be converted to an aldehyde with DMSO and heat. This material may be condensed with the phosphonate anion shown then converted to a ketenedithioacetal as shown previously. Condensation with hydrazine and a dicarbonyl will give final compound 21.

Scheme 6 provides a route to pyrazolo[1,5-a]pyrimidines where E is N. Alkylation of malononitrile with bromide 2 gives 22. Condensation with hydrazine and a dicarbonyl will give 21 which may then be alkylated and/or acylated to give 25.

Sulfide 21 may be easily converted to the corresponding alkoxy derivative upon treatment with a sodium alkoxide as shown in Scheme 7.[7] Conversion of the sulfide to a sulfone might assist in the displacement reaction.

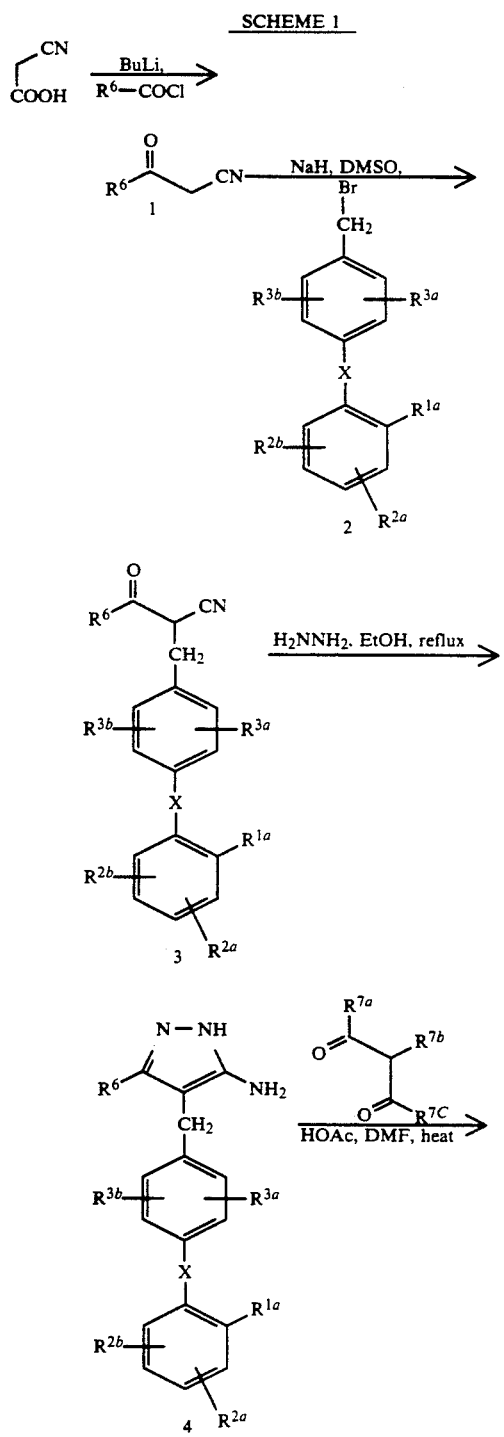

-continued
SCHEME 1
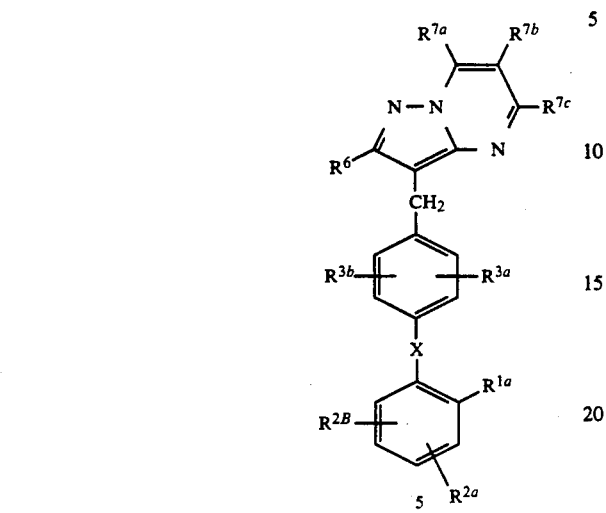
5
SCHEME 2
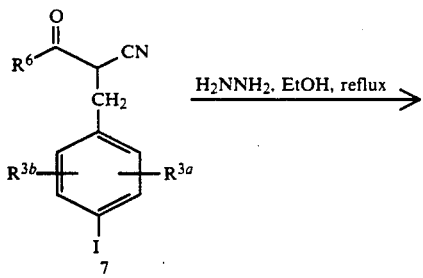
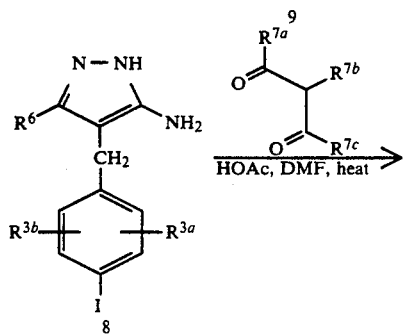
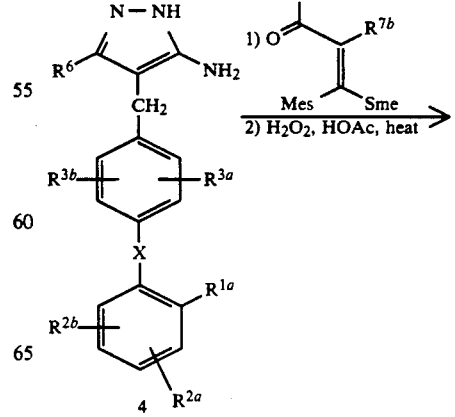
8
-continued
SCHEME 2
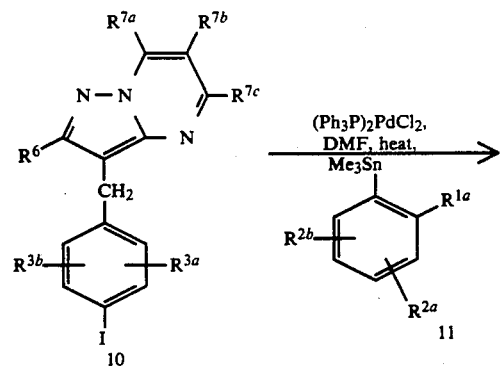
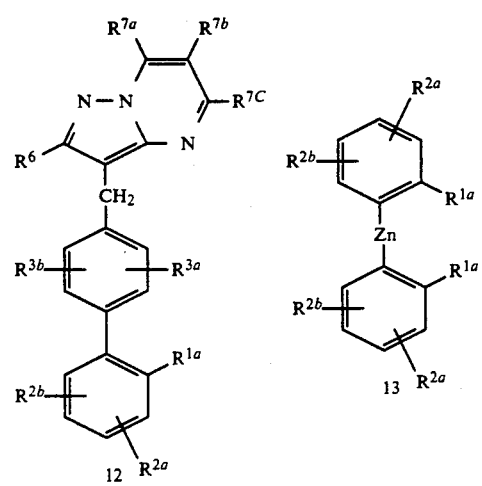
SCHEME 3
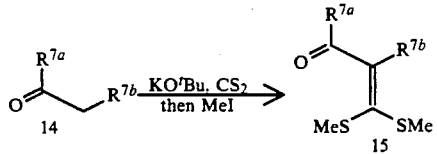
SCHEME 4

SCHEME 4
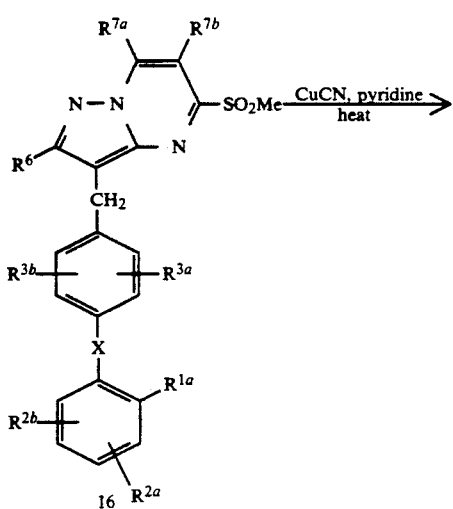
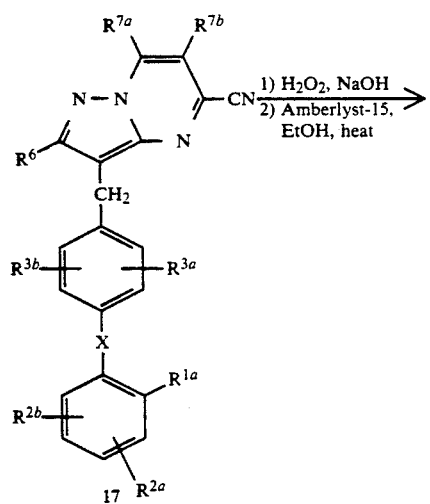
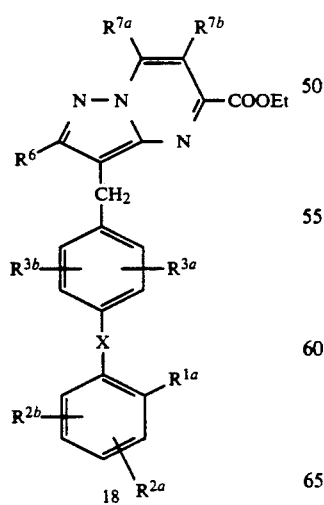
SCHEME 5
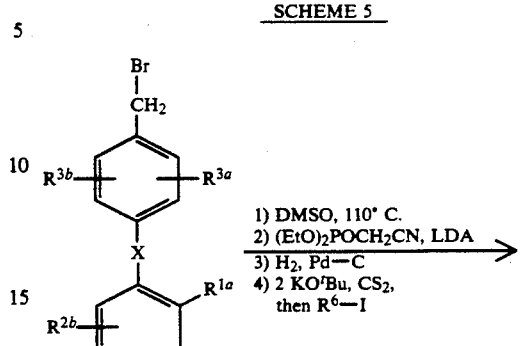
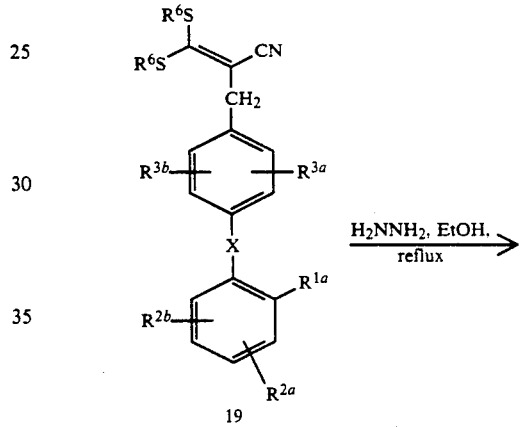
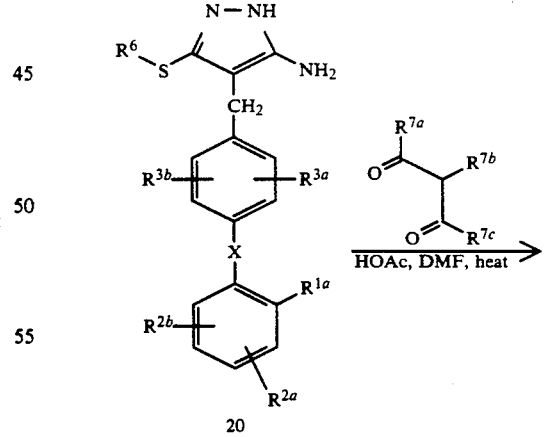
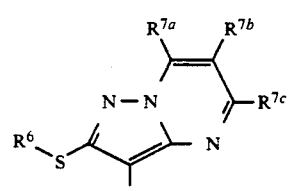

-continued
SCHEME 5
SCHEME 6
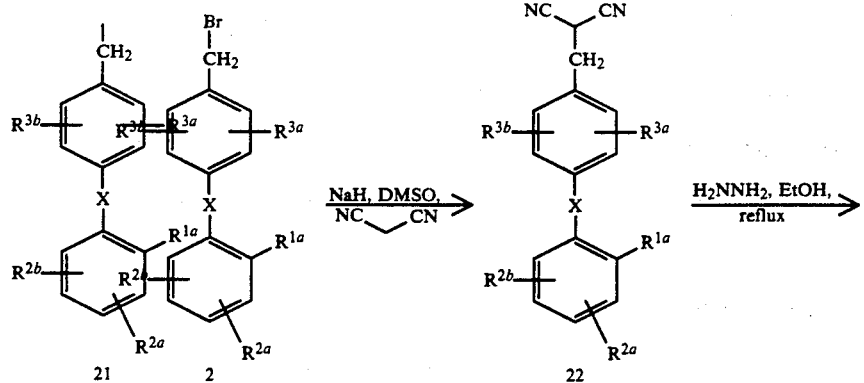
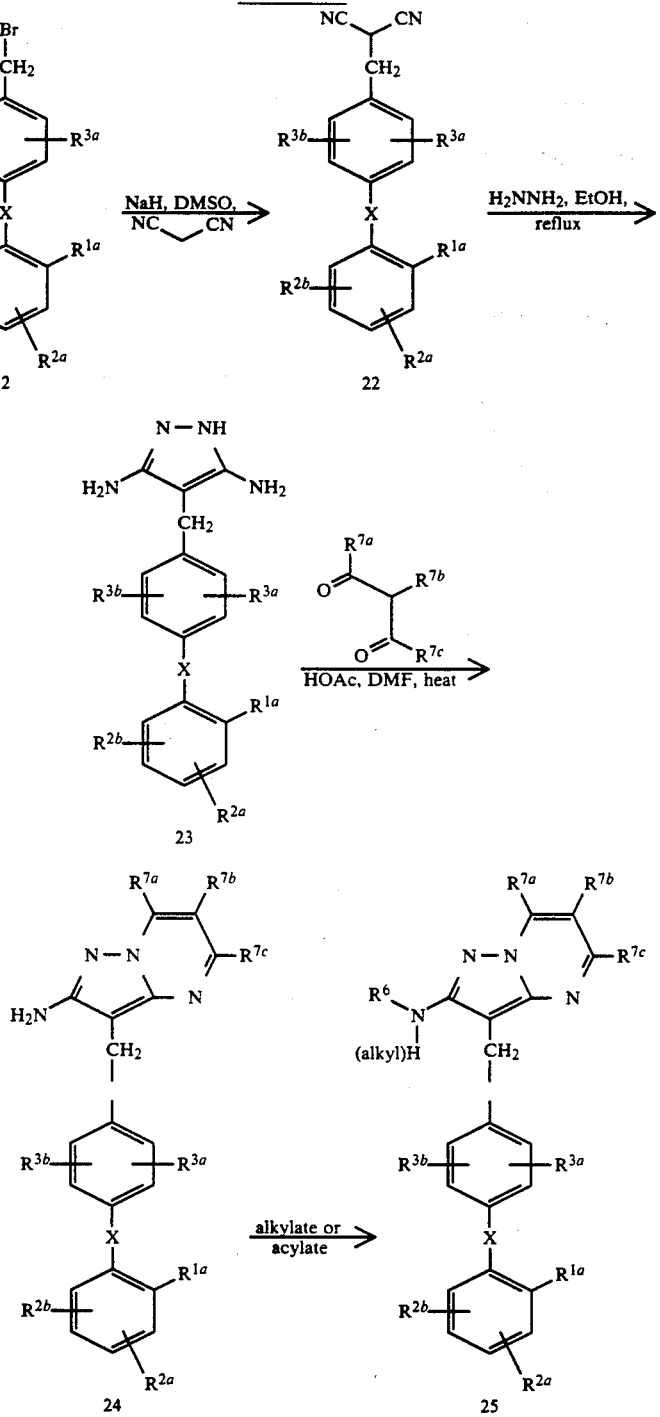

SCHEME 7

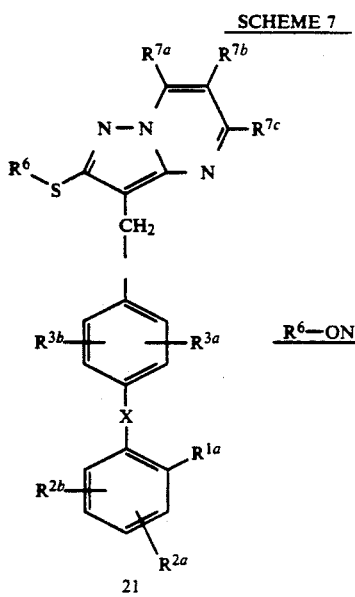

SCHEME 8

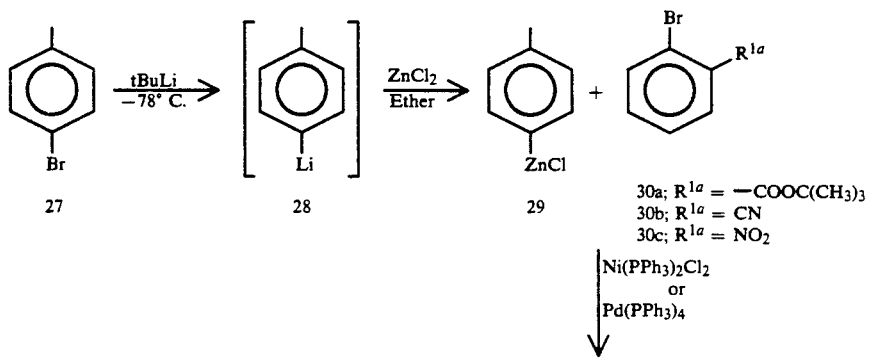

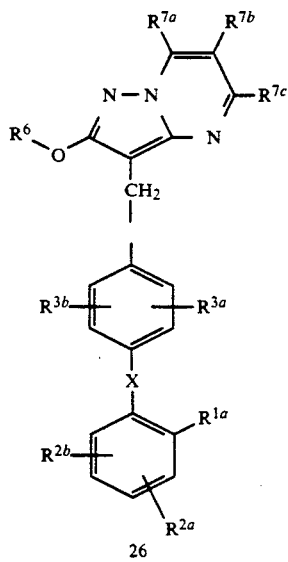

The substituted benzyl halides (2) including the more preferred alkylating agents (32a and 32b and 32c, Scheme 8) can be prepared as described in European Patent Applications 253,310 and 291,969 and the references cited therein. In addition a preferred method to prepare the biphenyl precursors 31a, 31b and 31c using Ni(O) or Pd(O) catalyzed cross-coupling reaction [E. Negishi, T. Takahashi, and A. O. King, *Org. Synthesis*, 66, 67 (1987)] is outlined in Scheme 8. As shown in Scheme 8, treatment of 4-bromotoluene (27) with t-BuLi, followed by the addition of a solution of $ZnCl_2$, produces the organo-zinc compound (29). Compound (29) is then coupled with 30a or 30b in the presence of $Ni(PPh_3)Cl_2$ catalyst to produce the desired biphenyl compound 31a or 31b. Similarly, 1-bromo-2-nitrobenzene (30c) is coupled with organo-zinc compound 29 in the presence of $Pd(PPh_3)_4$ catalyst [prepared by treating $Cl_2Pd(PPh_3)_2$ with $(i-Bu)_2AlH$ (2 equiv.)] to give the biphenyl compound 31c. These precursors, 31a, 31b and 31c, are then transformed into halomethylbiphenyl derivatives 32a, 32b and 32c, respectively, according to procedures described in European Patent Applications 253,310 and 291,969.

When there is additional substitution on the second phenyl ring ($R^2$ not hydrogen) the preferred method to prepare the biphenyl precursors 36 and 37, using the Pd(O) catalyzed cross-coupling reaction [J. K. Stille, *Angew. Chem. Int. Ed. Engl.*, 25, 508 (1986)], is outlined in reaction Scheme 9. As shown in Scheme 9, p-tolytrimethyltin (33) is coupled with 34 or 35 in refluxing toluene in the presence of 5 mole % of $Pd(PPh_3)_4$ to produce the desired biphenyl compounds 36 and 37. Table I illustrates the synthetic utility of this protocol. Compounds 36 ($R^2=NO_2$) and 37 ($R^2=NO_2$) could be converted to their respective chlorides by catalytic hydrogenation, diazotization and treatment with copper (I) chloride. The biphenyl fluorides which could not be obtained by direct coupling to a fluoro arylbromide were prepared from 36 ($R^2=NO_2$) and 37 ($R^2=NO_2$) via reduction, formation of the diazonium tetrafluoroborate salt and thermal decomposition. These precursors 36 ($R^2=NO_2$ or F or Cl) and 37 ($R^2=NO_2$ or F or Cl) are then transformed into the halomethyl biphenyl derivatives 38 and 39, respectively according to the procedures described in European Patent Applications 253,310 and 292,969.

SCHEME 8 -continued

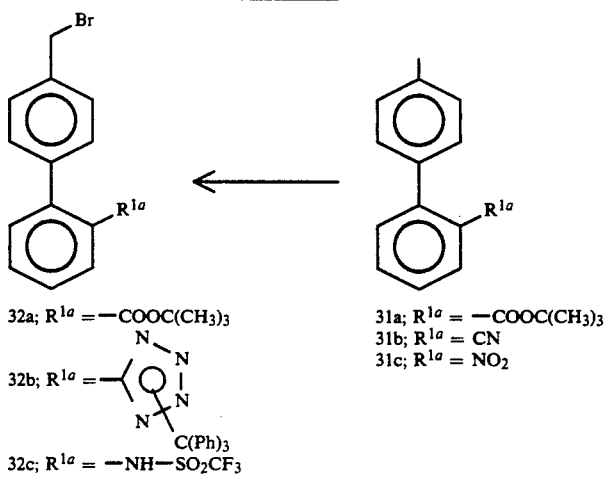

32a; $R^{1a}$ = —COOC(CH$_3$)$_3$
32b; $R^{1a}$ = [tetrazole-C(Ph)$_3$]
32c; $R^{1a}$ = —NH—SO$_2$CF$_3$ 31a; $R^{1a}$ = —COOC(CH$_3$)$_3$
31b; $R^{1a}$ = CN
31c; $R^{1a}$ = NO$_2$

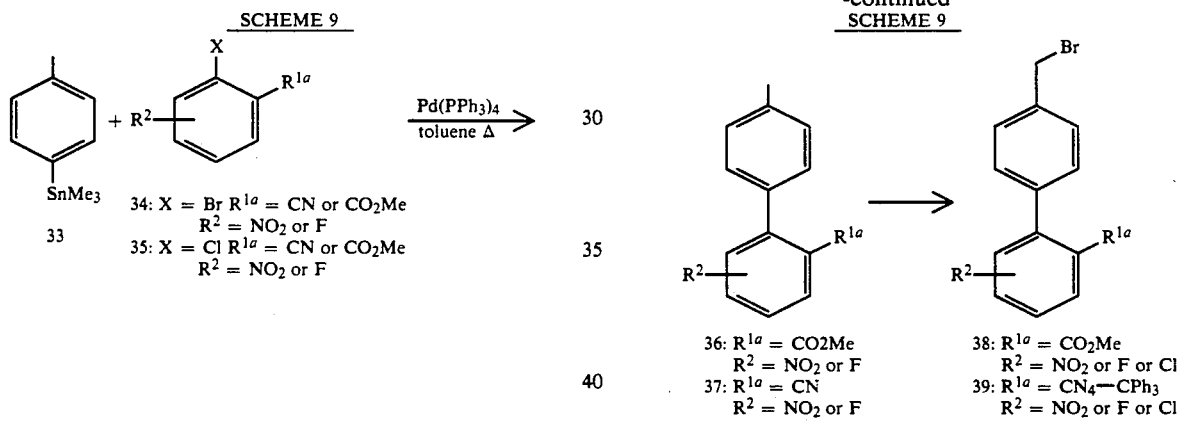

SCHEME 9

33

34: X = Br $R^{1a}$ = CN or CO$_2$Me
    $R^2$ = NO$_2$ or F
35: X = Cl $R^{1a}$ = CN or CO$_2$Me
    $R^2$ = NO$_2$ or F

-continued SCHEME 9

36: $R^{1a}$ = CO2Me
    $R^2$ = NO$_2$ or F
37: $R^{1a}$ = CN
    $R^2$ = NO$_2$ or F

38: $R^{1a}$ = CO2Me
    $R^2$ = NO$_2$, F or Cl
39: $R^{1a}$ = CN$_4$—CPh$_3$
    $R^2$ = NO$_2$, F or Cl

TABLE I
Biphenyl Synthesis

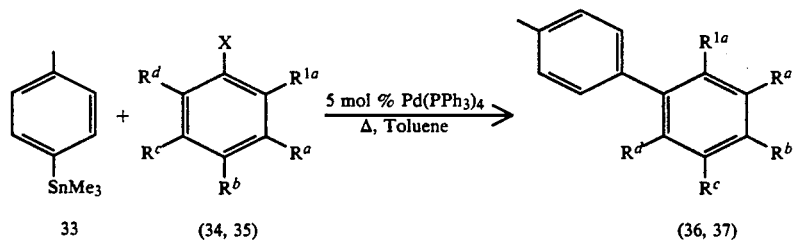

| X | $R^{1a}$ | $R^a$ | $R^b$ | $R^c$ | $R^d$ | Product ($R^a$) | Rf (solvent) | Yield |
|---|---|---|---|---|---|---|---|---|
| Br | CO$_2$Me | NO$_2$ | H | H | H | 36 (3'-nitro) | 0.35 (15:1 Hex/EtOAc) | 71% |
| Br | CN | H | NO$_2$ | H | H | 37 (4'-nitro) | 0.62 (2 × 6:1 Hex/EtOAc) | 74% |
| Br | CO$_2$Me | H | F | H | H | 36 (4'-fluoro) | 0.43 (15:1 Hex/EtOAc) | 83% |
| Cl | CO$_2$Me | H | H | NO$_2$ | H | 36 (5'-nitro) | 0.22 (15:1 Hex/EtOAc) | 70% |
| Br | CO$_2$Me | H | H | H | NO$_2$ | 36 (6'-nitro) | 0.24 (15:1 Hex/EtOAc) | 79% |
| Br | CN | H | F | H | H | 37 (4'-fluoro) | 0.44 (15:1 Hex/EtOAc) | 64% |
| Cl | CN | H | H | F | H | 37 (5'-fluoro) | 0.40 (15:1 Hex/EtOAc) | 62% |

SCHEME 10
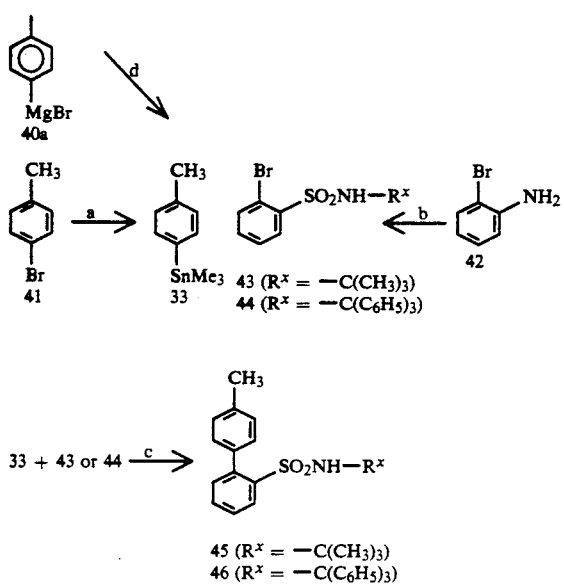
a. t-BuLi/ether, −78° C.
b. i) NaNO₂/HCl ii) SO₂, CuCl₂
c. Pd(PPh₃)₄, Toluene or (PPh₃)₂PdCl₂, DMF, 90° C.
d. Me₃SnCl.
SCHEME 11
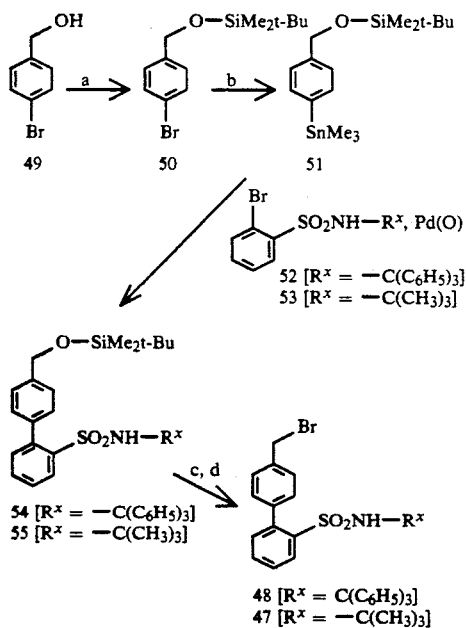
a. t-BuMe₂Si—Cl/Imidazole, DMF
b. t-BuLi, −78° C., Me₃SnCl
c. Tetrabutylammonium fluoride
d. CBr₄/Ph₃P.
SCHEME 12
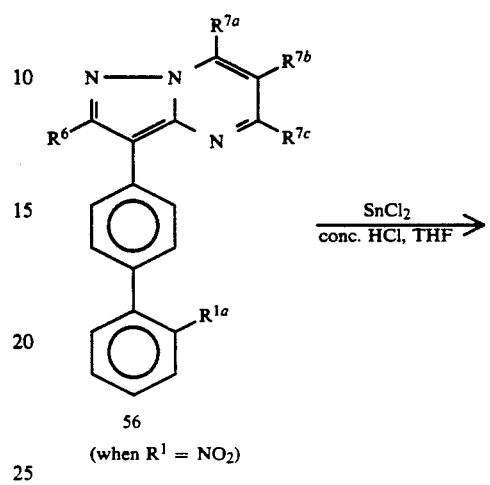
(when R¹ = NO₂)
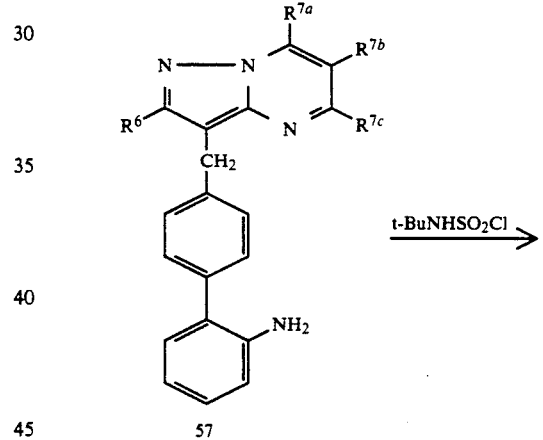
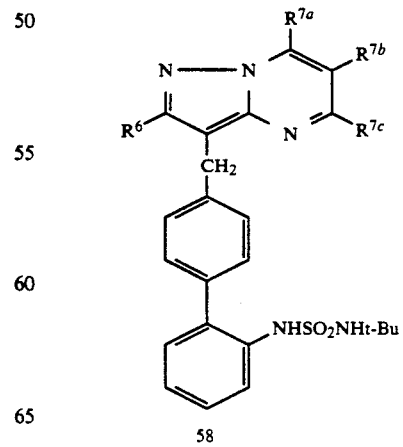

-continued
SCHEME 12
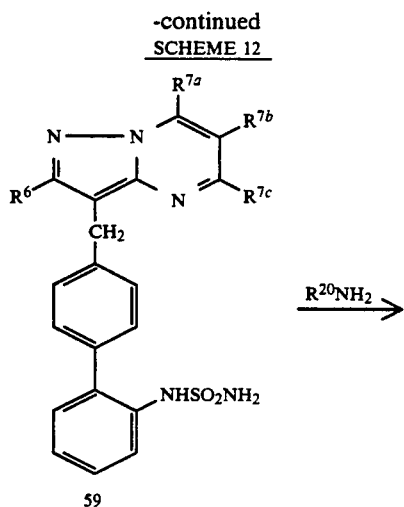
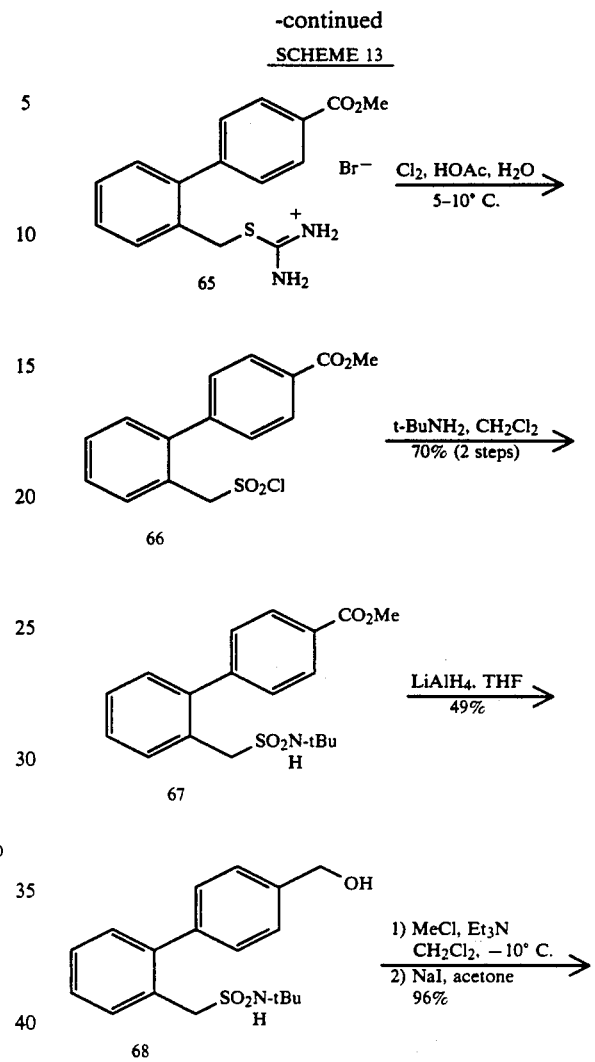
SCHEME 13
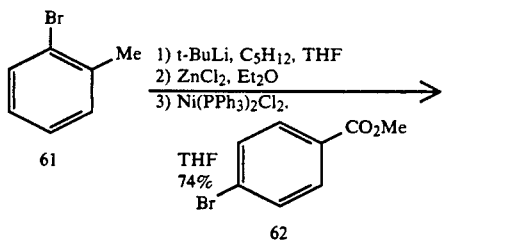
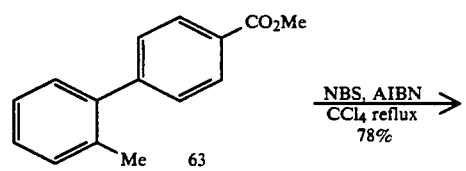
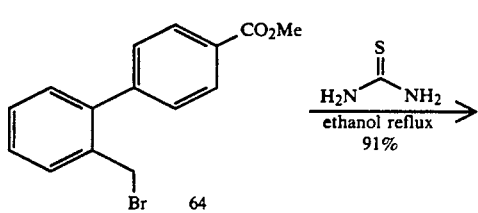
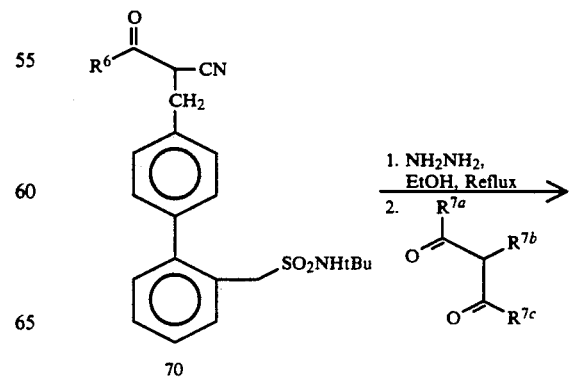

SCHEME 13 -continued

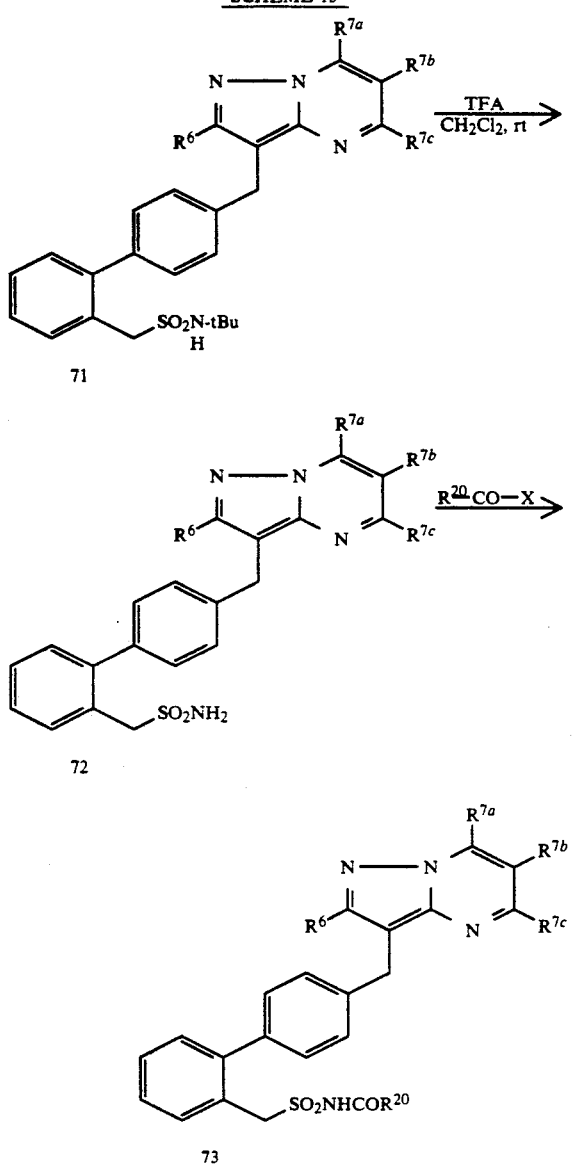

12. The compound 59 may be obtained from the corresponding N-t-butylsulfamide 58 after treatment with anhydrous trifluoroacetic acid [J. D. Catt and W. L. Matier, *J. Org. Chem.*, 39, 566 (1974)], which may be prepared by the reaction of the aromatic amine 57 with t-butylsulfamoyl chloride [W. L. Matier, W. T. Comer and D. Deitchman, *J. Med. Chem.*, 15, 538 (1972)]. Compound 57 is obtained from the corresponding nitro derivative 56.

Antagonists of Formula I in which $R^1=$—$CH_2SO_2NHCOR^{20}$ may be prepared as illustrated in Scheme 13. 2-Bromotoluene (61) is treated with t-butyllithium abd then zinc chloride. Coupling of the resulting metallo-zinc species with 4-bromobenzoic acid methyl ester (62) is then carried out with bis(triphenylphosphine)nickle(II) chloride as catalyst. Bromination of the resulting biphenyl (63) is then carried out using N-bromosuccinimide, affording bromide 64. Treatment of the bromide with thiourea affords the salt 65 which is treated with chlorine to yield sulfonyl chloride 66. Treatment of 66 with t-butylamine affords sulfonamide 67, which is converted by treatment with lithium aluminum hydride to the alcohol 68. Conversion of 68 of the corresponding iodide 69 is carried out by treatment with methanesulfonyl chloride to afford a sulfonate ester, followed by treatment with sodium iodide in acetone. The iodide 69 is used to alkylate the sodium salt of an appropriate β-keto nitrile affording the sulfonamide 70. The corresponding pyrazolo[1,5-a]pyrimidine 71 is then prepared by the treatment of 70 with hydrazine in refluxing ethanol hydrate followed by reaction with an appropriate 1,3-dicarbonyl compound, which on further treatment with trifluoroacetic acid and then with an appropriate acylating agent affords the desired acylsulfonamides 73.

The biaryl sulfonamides 45 and 46 can be prepared alternatively using palladium(0) catalyzed cross-coupling reactions of appropriate aryl-organotin precursors [J. K. Stille, *Pure Appl. Chem.*, 57, 1771 (1985); T. R. Bailey, *Tetra Lett.*, 27, 4407 (1986); D. A. Widdowson and Y. Z. Zhang, *Tetrahedon*, 42, 2111 (1986)], as outlined in Scheme 10. The organotin compound 33 [S. M. Moerlein, *J. Organometallic Chem.*, 319, 29 (1987)], obtained from the aromatic precursor 41 or 40, may be coupled with aryl sulfonamides 43 and 44 using Pd(PPh3)4 or (PPh3)2PdCl2 as catalysts to give biaryl sulfonamides 45 and 46, respectively, which may then be converted into the corresponding biphenyl methyl bromides 47 and 48. The biphenyl metyl bromides 47 and 48 may be alternatively prepared from the appropriate organotin precursor 51 using the Pd(0) catalyzed cross-coupling reaction as outlined in Scheme 11.

Compounds where $R^{1a}=$—$NHSO_2NHR^{20}$ may be prepared by the reaction of appropriate primary amines with the sulfamide 59 [S. D. McDermott and W. J. Spillane, *Synthesis*, 192 (1983)], as described in Scheme

SCHEME 14

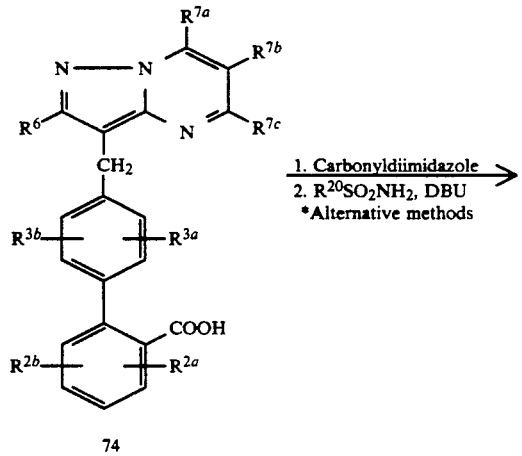

1. Carbonyldiimidazole
2. $R^{20}SO_2NH_2$, DBU
*Alternative methods

-continued
SCHEME 14

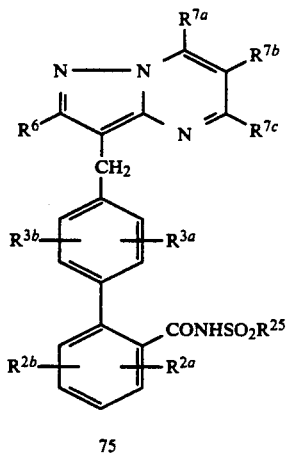

75

*Alternative methods:
<sup>a</sup>(i) SOCl<sub>2</sub>, reflux (ii) R<sup>20</sup>SO<sub>2</sub>NH<sup>−</sup>M<sup>+</sup> (where M is Na, K or Li)
<sup>b</sup>(i) (COCl)<sub>2</sub>·DMF, −20 C. (ii) R<sup>20</sup>SO<sub>2</sub>NH<sup>−</sup>M<sup>+</sup>
<sup>c</sup>(i) N(N,N-Diphenylcarbamoyl)pyridinium chloride/Aq. NaOH (ii) R<sup>20</sup>SO<sub>2</sub>NH<sup>−</sup>M<sup>+</sup>

Compounds of formula I and formula Ia where $R^{1a}$ is —CONHSO$_2$R$^{20}$ (where R$^{20}$=alkyl, aryl or heteroaryl) may be prepared from the corresponding carboxylic acid derivatives (74) as outlined in Scheme 14. The carboxylic acid (74), obtained as described earlier can be converted into the corresponding acid chloride by treatment with refluxing thionyl chloride or preferably with oxalylchloride and a catalytic amount of dimethylformamide at low temperature [A. W. Burgstahler, L. O. Weigel, and C. G. Shaefer—*Synthesis*, 767, (1976)]. The acid chloride then can be treated with the alkali metal salt of R$^{20}$SO$_2$NH$_2$ to form the desired acylsulfonamide 75. Alternatively, these acylsulfonamides may be also prepared from the carboxylic acids using N,N-diphenylcarbamoyl anhydride intermediates [F. J. Brown et at—*European* Patent Application, EP 199543; K. L. Shepard and W. Halczenko—*J. Het. Chem.*, 16, 321 (1979)]. Preferably the carboxylic acids (74) can be converted into acyl-imidazole intermediates, which can be then treated with an appropriate aryl or alkylsulfonamide and 1,8-diazabicyclo[5.4.o]undec-7-ene (DBU) to give the desired acylsulfonamide 75 [J. T. Drummond and G. Johnson—*Tetra. Lett.*—29, 1653 (1988)].

Angiotensin II antagonists containing imidazo[1,2-b]pyridazines of general structure Ib are readily synthesized as shown in Schemes 15 through 24. Schemes 15 and 16 illustrate the synthesis of substituted 3-aminopyridazines (79) which are intermediates used for the synthesis of imidazo[1,2-b]pyridazines. In Scheme 15, 4-amino-1,2,4-triazole is condensed with a substituted b-dicarbonyl compound (76) to afford intermediates such as 77. Alkylation of 77 with phenacyl bromide yields salts such as 78 which upon subsequent basic hydrolysis afford substituted 3-aminopyridazines (79).[8] Alternatively, 3-aminopyridazines where R$^{7c}$ is an ester group may be prepared according to Scheme 16. In Scheme 16, a substituted succinic ester (80) is condensed with dimethyloxalate in basic media to provide adduct 81.[9] Decarboalkoxylation[10] of 81 affords the substituted ketoglutaric esters 82, which are then condensed with hydrazine hydrate to yield dihydropyridazones 83.[11] These intermediates (83) are then oxidized to pyridazones 84 with bromine in hot acetic acid, and then converted to substituted 3-chloropyridazines (85) by reaction with phosphorous oxychloride.[12] Chloropyridazines 85 are converted directly to 3-aminopyridazines 79 (R$^{7c}$ is CO$_2$Me) with ammonia at high temperature in a sealed reactor, or they may be reacted with benzylamine and subsequently debenzylated by hydrogenolysis. Substituted 3-amino-6-arylpyridazines (79 where R$^{7c}$ is aryl) are also readily prepared from acetophenone derivatives by a strategy similar to Scheme 16.[13]

SCHEME 15

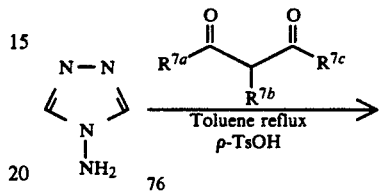

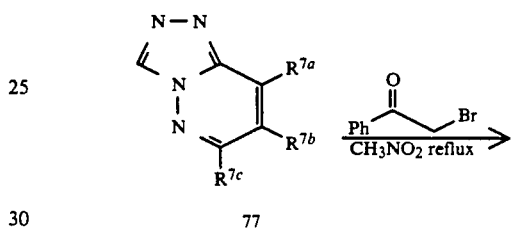

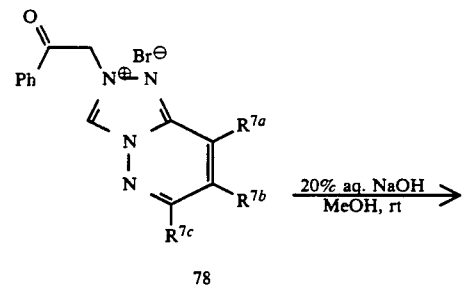

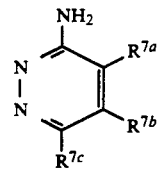

79

SCHEME 16

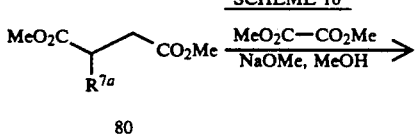

80

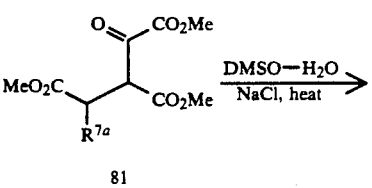

81

-continued
SCHEME 16

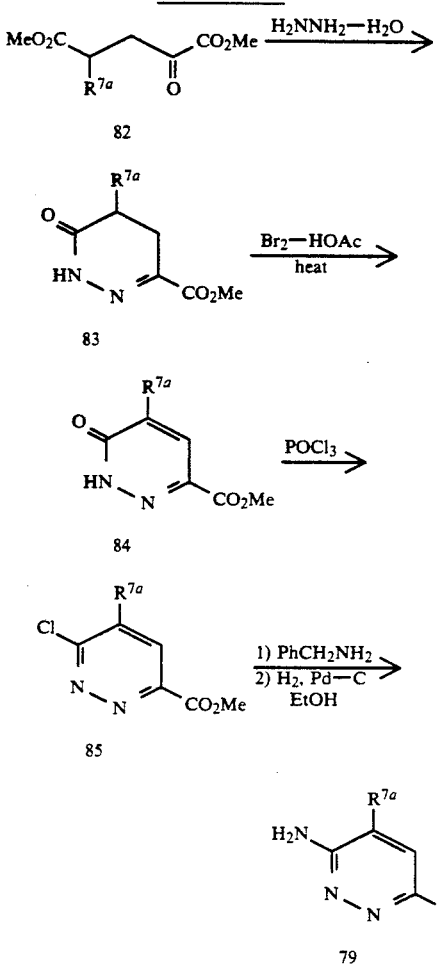

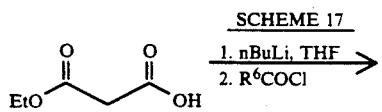

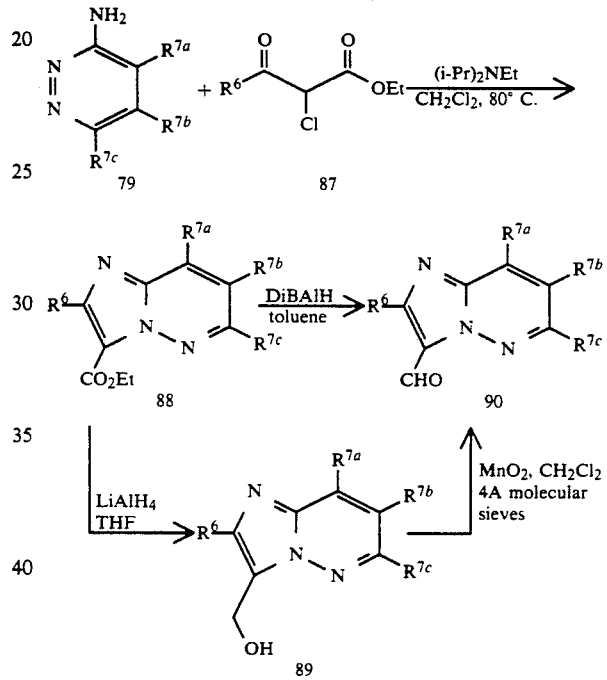

90 may be accomplished using diisobutylaluminum hydride in a solvent such as toluene or methylene chloride at low temperature.

Scheme 17 illustrates the general route for the preparation of α-chloro-β-ketoesters (87) containing the $R^6$ substituent which are required for reaction with 3-aminopyridazines (79) to form the imidazo[1,2-b]pyridazine ring. When it is desired that $R^6$ be methyl or ethyl the appropriate b-ketoeters (86) are commercially available. Alternatively, β-ketoesters bearing various $R^6$ substituents are readily prepared by acylation of the dianion derived from ethyl malonic acid with an acid chloride. Acidification of the reaction mixture results in decarboxylation to provide the b-ketoester 86 as shown in Scheme 17.[14] The β-ketoester 86 is then chlorinated with sulfuryl chloride to provide α-chloro-β-ketoester 87.[15]

Scheme 18 illustrates the next stage in the synthesis of substituted imidazo[1,2-b]pyridazine angiotensin II antagonists. Reaction of a substituted 3-aminopyridazine 79 with an a-chloro-b-ketoester 87 in the presence of an amine base at elevated temperature affords the imidazo[1,2-b]pyridazine ester 88. The reaction may be conducted conveniently in methylene chloride at 80° C. in a sealed pressure vessel or alternatively, a higher boiling halocarbon solvent may be substituted allowing the reaction to be performed at atmospheric pressure. The imidazo[1,2-b]pyridazine ester 88 is then reduced to the alcohol 89 with lithium aluminum hydride in THF, then oxidized to the aldehyde 90 using manganese dioxide in the presence of powdered molecular sieves. Alternatively, a single step conversion of ester 88 to aldehyde In the next stage of the synthesis of imidazo[1,2-b]pyridazine containing angiotensin II antagonists the aldehyde 90 is elaborated to the benzyl substituted imidazo[1,2-b]pyridazine 96 as shown in Scheme 19. A Grignard reagent (91) is first prepared from the t-butyl-dimethylsilylether of a suitably substituted 4-bromophenol. This Grignard reagent is allowed to react with aldehyde 90 in THF at 0° C. and after workup, the alcohol 92 is isolated. The silyl protecting group is then removed from alcohol 92 with tetra-n-butylammonium fluoride which provides the phenol 93. The secondary alcohol of 93 is reduced to a methylene group using in situ generated diiododimethylsilane in acetonitrile at room temperature which affords 94.[16]

Imidazo[1,2-b]pyridazine containing angiotensin II antagonists of general structure Ib wherein X=O may be prepared from the intermediate phenol 94 as shown in Scheme 20. A modified Ullmann coupling of phenol 94 with a substituted 2-chlorobenzoic acid gives antagonists such as 95 where X=O and $R^{1a}$ is a carboxylic acid group.[17] Similar reaction of 94 with a substituted 2-bromobenzonitrile followed by reaction of the nitrile (96) with trimethyltin azide in toluene at elevated temperature gives antagonists such as 97 where X=O and $R^{1a}$ is a tetrazole group.
SCHEME 19
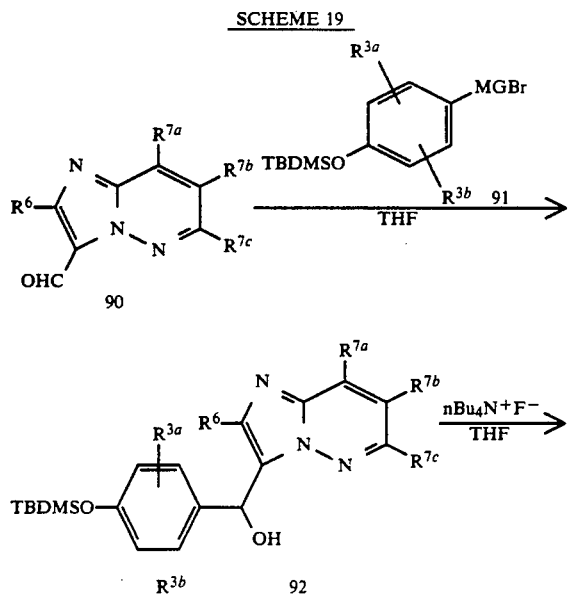
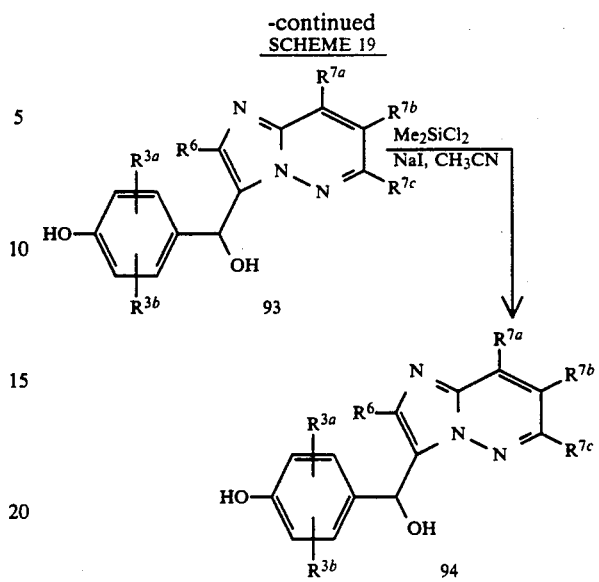
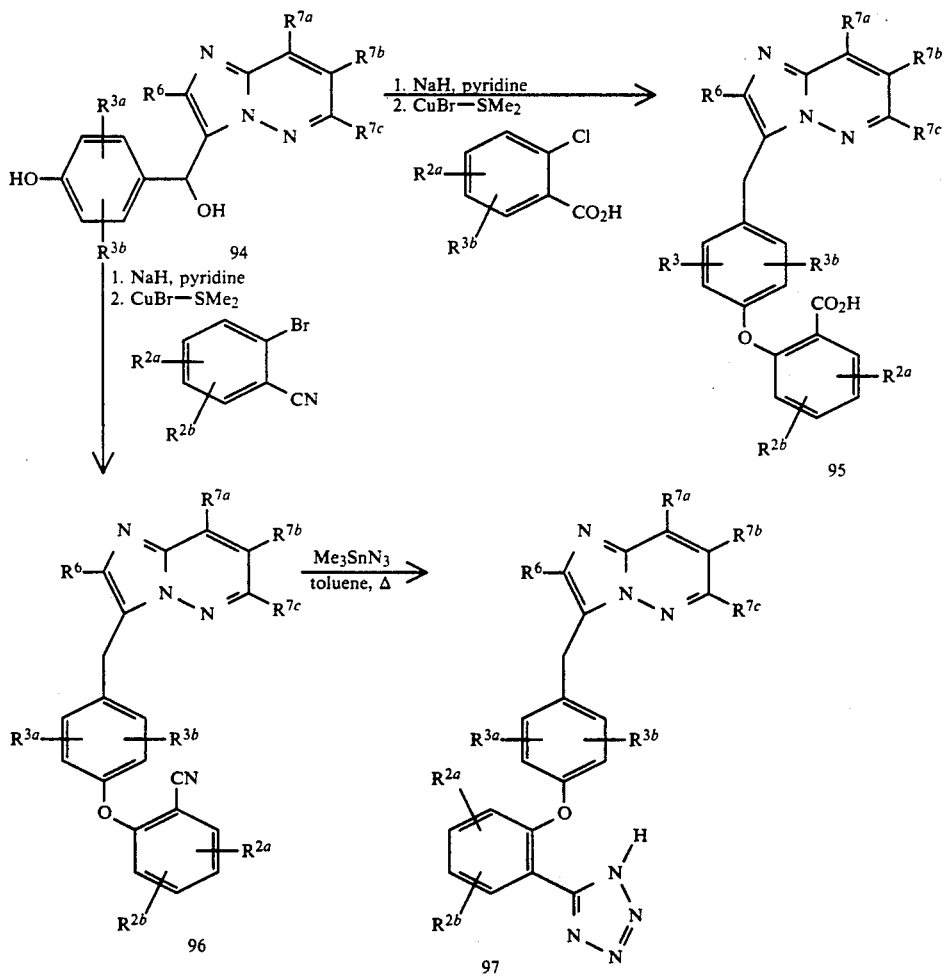
Preparation of imidazo[1,2-b]pyridazine containing angiotensin II antagonists of general structure Ib wherein X is a single bond are prepared from the intermediate substituted phenols 94 as shown in Schemes 21-24. Scheme 21 illustrates the final steps of the synthesis for antagonists wherein $R^{1a}$ is either a carboxylic acid (101) or an acidic equivalent group derived from a carboxylic acid such as 102 or 103. Phenol 94 is first converted to the phenol triflate 98 using trifluoromethanesulfonic anhydride in pyridine. The triflate 98 is in turn converted to the versatile aryltrimethylstannane 99 by a palladium catalyzed reaction of triflate 98 with hexamethylditin.[18] The stannane 99 may then be employed in palladium catalyzed cross coupling reactions with various substituted aryl halides to prepare angiotensin II antagonists of general structure Ib with differing $R^{1a}$, $R^{2a}$ and $R^{2b}$ substituents.[19] In this scheme, the palladium catalyzed cross coupling of stannane 99 with a substituted t-butyl 2-iodobenzoate affords esters such as 100. Acidic hydrolysis of the t-butyl ester group in 100 gives the desired carboxylic acids 101. Acylsulfonamides such as 102 in which the acyl group is directly attached to the aromatic ring bearing the $R^{2a}$ and $R^{2b}$ substituents may be prepared from 101 by activation of the carboxylic with carbonyldiimidazole in refluxing THF, followed by reaction with a sulfonamide in the presence of DBU. Similarly, activation of the carboxylic acid 101 with carbonyldiimidazole followed by reaction with a substituted 5-aminotetrazole leads to antagonists with structures such as 103.

SCHEME 21

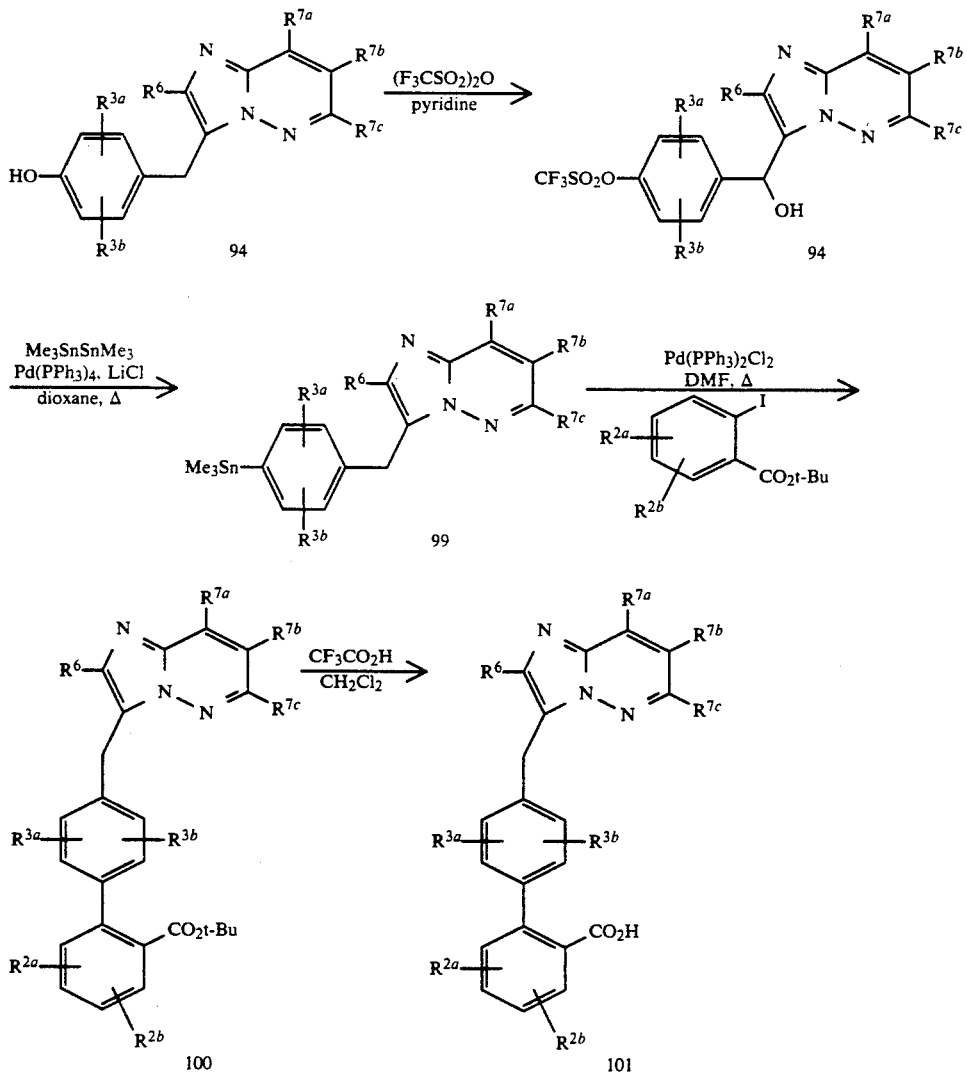

-continued
SCHEME 21

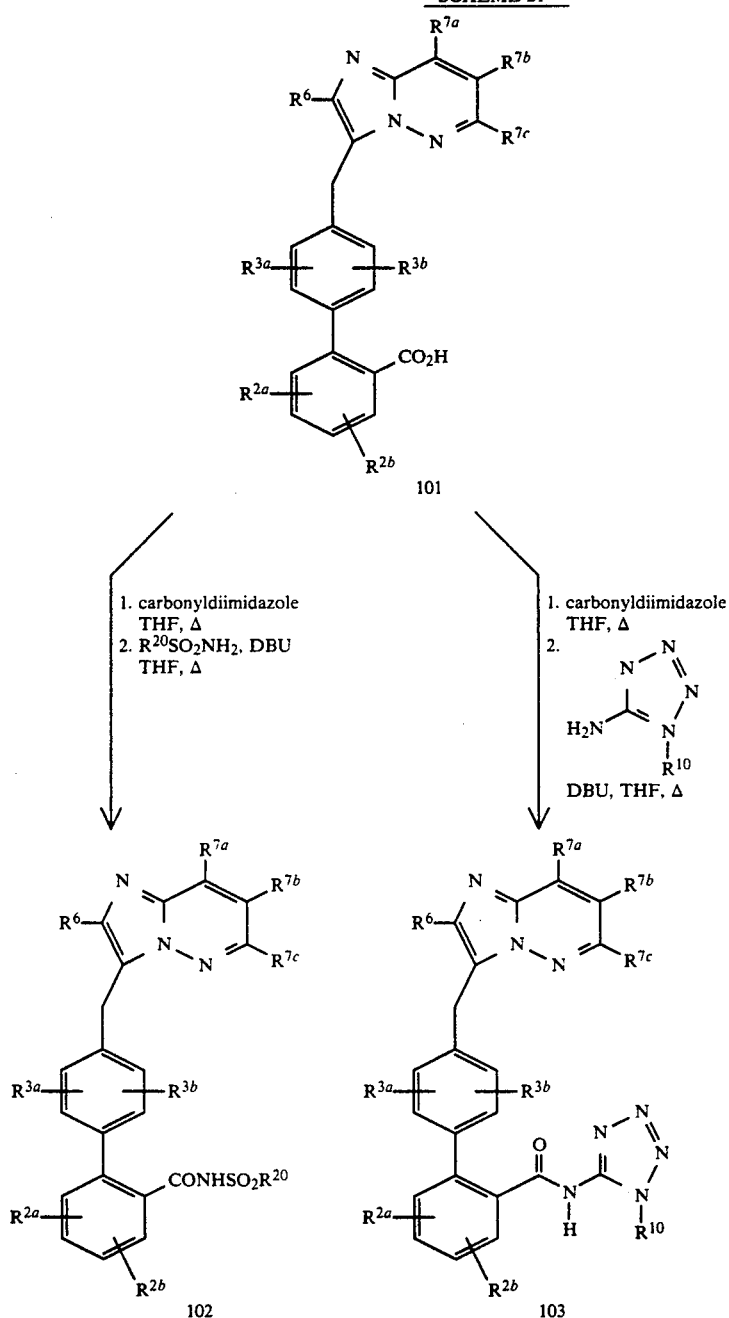

In Scheme 22 the steps leading from stannane 99 to angiotensin II antagonists wherein X is a single bond and $R^{1a}$ is a trifluoromethanesulfonamide group are shown. Palladium catalyzed cross coupling of stannane 99 with a substituted 2-bromonitrobenzene affords nitrobiphenyls like 104. The nitro group of 104 may be reduced to an amino group (105) by catalytic hydrogenation or alternatively using reducing agents such as stannous chloride in hydrochloric acid. The amine 105 may then be reacted with trifluoromethanesulfonic anhydride in the presence of a base such as pyridine to provide the trifluoromethanesulfonamides related to 106.

Scheme 23 illustrates the preparation of angiotensin II antagonists of general structure Ib wherein X is a single bond and $R^{1a}$ is a tetrazole group. The palladium catalyzed cross coupling reaction of the stannane 99 with a substituted 2-bromobenzonitrile leads to cyanobiphenyls with general structure 107. These cyano compounds may be converted to tetrazoles such as 108 upon reaction with trimethyltin azide at elevated temperatures in a suitable solvent such as toluene.

Scheme 24 illustrates the synthesis of angiotensin II antagonists of general structure Ib where X is a single bond and $R^{1a}$ is an acylsulfonamide in which the sulfonyl group is attached directly to the aromatic ring bearing the $R^{2a}$ and $R^{2b}$ substituents. The palladium catalyzed cross coupling reaction of the stannane 99 with a substituted N-t-butyl-2-bromosulfonamide affords the t-butyl protected biphenylsulfonamide 109. After the coupling reaction the t-butyl protecting group is no longer required and it may be removed under acidic conditions such as trifluoroacetic acid in methylene chloride to provide sulfonamides such as 110. Reaction of the biphenylsulfonamides (110) with a preformed acylimidazole (prepared from a carboxylic acid $R^{20}CO_2H$, and carbonyldiimidazole) with a base such as DBU in a solvent such as THF at elevated temperatures gives the acylsulfonamides related to 111.

SCHEME 22

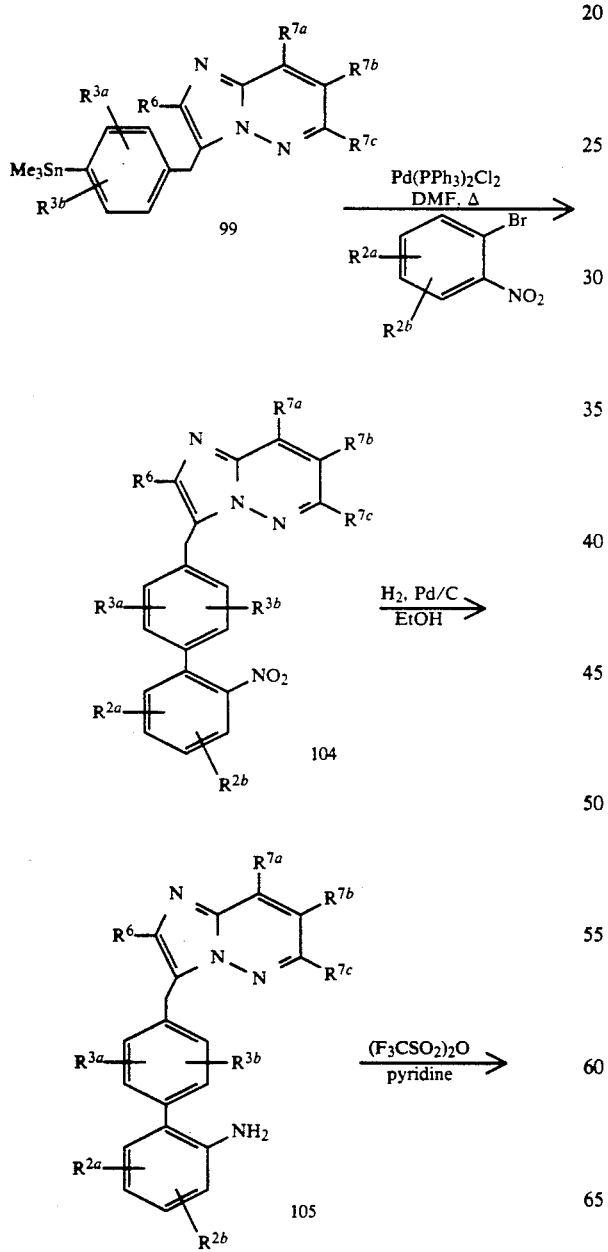

-continued

SCHEME 22

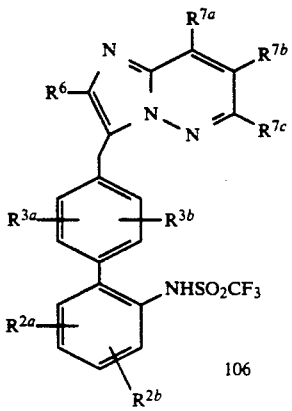

SCHEME 23

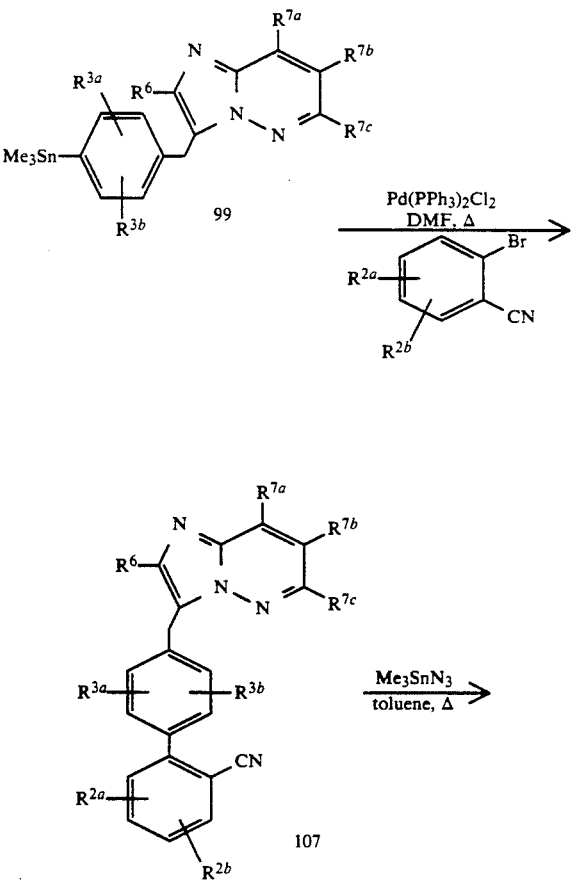

-continued
SCHEME 23

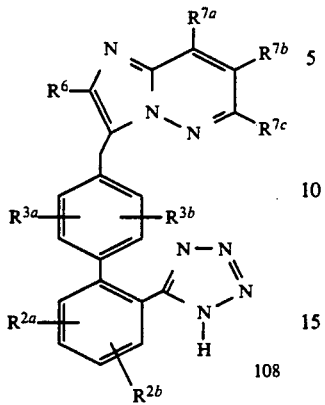

108

SCHEME 24

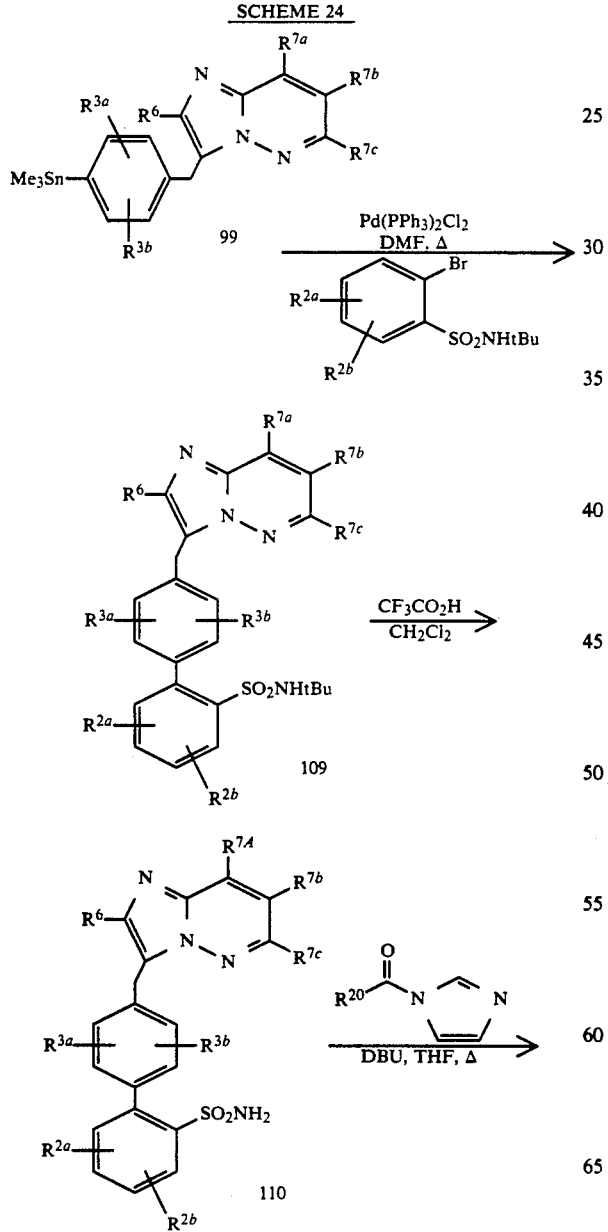

-continued
SCHEME 24

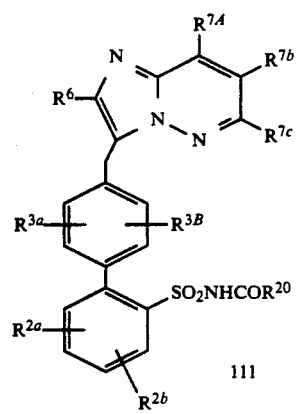

111

The 3,5-dioxo-1,2,4-oxadiazolidine group has been shown to function as a bioisostere for carboxylic acids and tetrazoles.[20] The synthesis of angiotensin II antagonists of general formula Ib wherein X is a single bond and $R^{1a}$ is a 3,5-dioxo-1,2,4-oxadiazolidine ring is shown in Scheme 25. The nitro group of intermediate 104 which was presented in Scheme 22, may be partially reduced to the hydroxylamino containing intermediate such as 112 using powdered zinc and an aqueous ammonium chloride solution with ethanol as cosolvent. Reaction of the substituted hydroxylamino intermediate 112 with ethoxycarbonylisocyanate in methylene chloride affords adducts such as 113 which may then be cyclized with Triton B in methanol to provide substituted angiotensin II antagonists like 114 bearing a 3,5-dioxo-1,2,4-oxadiazolidine ring as $R^{1a}$.

Scheme 26 illustrates a preferred embodiment of the invention of angiotensin II antagonists of general formula Ib wherein X is defined as the —O—CHR$^1$— group. The synthesis of antagonists with this structure begin with the phenolic intermediate 94 which was presented in Scheme 19. Phenols such as 94 may be reacted with a substituted a-bromophenylacetic ester under basic reaction conditions such as potassium carbonate in refluxing acetone which provides substituted phenoxyphenylacetic esters such as 115. The ester group of intermediate 115 is hydrolysed by sodium hydroxide in methanol to furnish the carboxylic acid bearing angiotensin II antagonists 116 ($R^1$=CO$_2$H). Acids such as 115 may in turn be activated as their acylimidazole derivatives with 1,1'-carbonyldiimidazole (THF, heat) and then reacted with a sulfonamide ($R^{20}SO_2NH_2$) in ..e presence of DBU to give the substituted acylsulfonamides 117 as shown. Alternatively, the intermediate acylimidazole can react with 5-aminotetrazole to lead to derivatives of general structure Ib such as 118. In this scheme $R^{10}$ may include substituents which function as a protecting group, and which are removed after the coupling reaction to give compounds of structure 118 wherein $R^{10}$ is hydrogen.

SCHEME 25
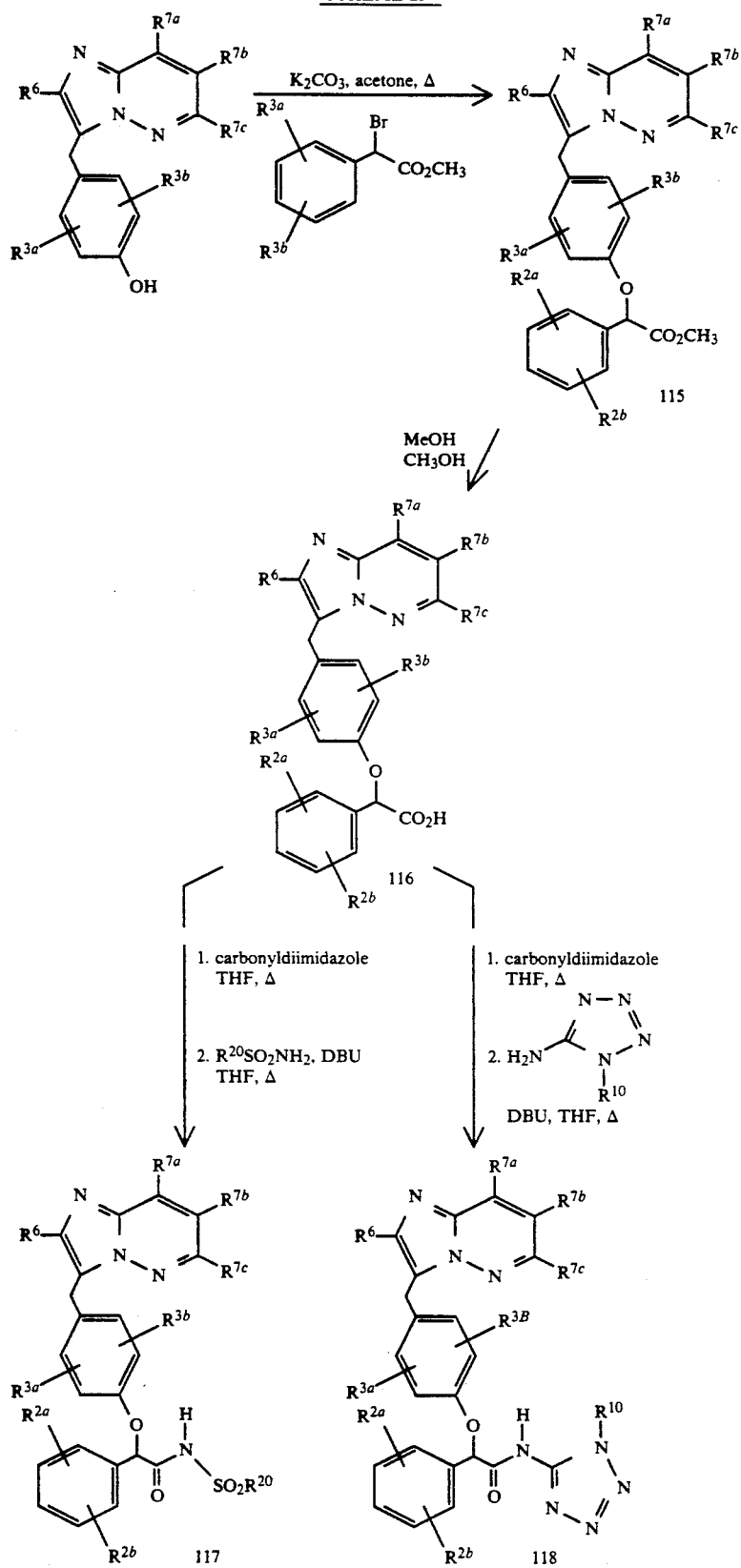
It should be appreciated that compounds such as 116 shown in Scheme 26 are produced as a racemic mixture and that these mixtures may be resolved into enantiomerically pure compounds using techniques known in the art. Diasteromeric salts of the enantiomers may be separated by techniques such as fractional crystallization and the pure enantiomers regenerated. Alternatively, diasteromeric esters, amides, imides or other carboxylic acid derivatives may be prepared from enantiomerically pure alcohols, amines or amides and the racemic acids of general structure 116. The diastereomers may then be separated chromatographically or by crystallization, and then converted back to the individual enantiomers. The preferred enantiomer is the more active compound as determined by the biological assay.

REFERENCES CITED

[1] J. C. Krauss, T. L. Cupps, D. S. Wise, L. B. Townsend, *Synthesis* (1983) 308.

[2] M. H. Elnagdi, M. R. H. Elmoghayar, G. E. H. Elgemeie, *Advances in Heterocyclic Chemistry*: Chemistry of Pyrazolopyrimidines (1987) 41, 319–376.
G. Muhmel, R. Hanke, E. Breitmaier, *Synthesis* (1982) 673.
J. S. Bajwa, P. J. Sykes, *J. Chem. Soc., Perkin I* (1980) 481.
J. J. Vaquero, L. Fuentes, J. C. Del Castillo, M. I. Perez, J. L. Garcia, J. L. Soto, *Synthesis* (1987) 33.
C. K. Chu, J. J. Suh, M. Mesbah, S. J. Cutler, *J. Het. Chem.* (1986) 23, 349.

[3] J. K. Stille, *Pure & Appl. Chem.* (1985) 57, 1771.
T. R. Bailey, *Tet. Lett.* (1986) 37, 4407.
I. P. Beletskaya, *J. Organomet. Chem.* (1983) 250, 551.
D. A. Widdowson, Y. Z. Zhang, *Tetrahedron* (1986) 42, 2111.
J. K. Stille, *Angew. Chem. Int. Ed. Engl.* (1986) 25, 508.
M. Kumada, *Pure & Appl. Chem.* (1980) 52, 669.
K. Tamao, K. Sumitani, Y. Kiso, M. Zembayashi, A. Fujioka, S. Kodama, I. Nakajima, A. Minato, M. Kumada, *Bull. Chem. Soc. Jap.* (1976) 49, 1958.

[4] S. M. S. Chauhan, J. Junjappa, *Tetrahedron* (1976) 32, 1779.
H. Junjappa, *Tetrahedron* (1990) 46, 577. [5] J. R. Beck, S. A. Ackmann, M. A. Staszak, F. L. Wright, *J. Het. Chem.* (1988) 25, 955.
T. J. Schwan, H. Tieckelmann, *J. Het. Chem.* (1964) 1, 201.

[6] W. J. Greenlee, E. D. Thorsett, *J. Org. Chem.* (1981) 46, 5351.

[7] See Chauhan, Ref. 4.

[8] Becker. H. G. O.; Böttcher, H. *Tetrahedron* 1968, 2687.

[9] Blaise, E. E.; Gault, H. *Bull. Soc. Chim.* 1911, 9, 451.

[10] Krapcho, A. P. *Tetrahedron Lett.* 1973, 957.

[11] Mitsui, S.; Saito H. *Nippon Kagaku Zasshi* 1957, 78, 577.

[12] McMillan, F. H.; Kun, K. A.; McMillan, C. B.; Schwartz, B. J.; King, J. A. *J. Am. Chem. Soc.* 1957, 78, 577.

[13] Wermuth, C. -G.; Schlewer, G.; Bourguignon, J. -J.; Maghioros, G.; Bouchet, M. -J.; Moire, C.; Kan, J. -P.; Worms, P.; Biziere, K. *J. Med. Chem.* 1989, 32, 528.

[14] Wierenga, W.; Skulnick, H. I. *Org. Synth.* 1983, Vol. 61, 5.

[15] Boehme, W. R. *Org. Synth.* 1963, Col. Vol. 4, 590.
Allihn, Ber., 1878, 11, 567.

[16] Wiggins, J. M. *Synth. Commun.* 1988, 18, 741.

[17] Boger, D. L.; Yohannes, D. *J. Org. Chem.* 1990, 55, 6000.

[18] Echavarren, A. M.; Stille, J. K. *J. Am. Chem. Soc.* 1987, 109, 5478.

[19] Milstein, D.; Stille, J. K. *J. Am. Chem. Soc.* 1979, 101, 4992.

[20] Kraus, J. L. *Pharmacol. Res. Commun.* 1983, 15, 119.
Kraus, J. L.; Dugenet, P.; Yaouanc, J. -J. *J. Heterocyclic Chem.* 1982, 19, 971.

[21] A. A. Sinkula in *Annual Reports in Medicinal Chemistry*, Vol. 10, R. V. Heinzelman, Ed., Academic Press, New York-London, 1975, Ch. 31, pp. 306–326.

It will be appreciated by those skilled in the art that functional group transformations can be conducted on aryl and heterocyclic rings to afford desired analogs. For example, esters may be converted to amides by heating them with amines and an amide nitrogen if present in the heterocycle may be alkylated using bases such as sodium hydride in DMF with the appropriate alkyl halide. Functional group protection throughout these syntheses will be chosen to be compatible with subsequent reaction conditions. Ultimately such protecting groups will be removed to generate the desired optimally active compounds of Formula I.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, $H_2SO_4$, $H_3PO_4$, methanesulfonic, toluenesulfonic, maleic, fumaric, camphorsulfonic. The non-toxic, physiologically, acceptable salts are preferred, although other salts are also useful; e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

It will be further appreciated that the compounds of general Formula I in this invention may be derivatised at functional groups to provide prodrug derivatives which are capable of conversion back to the parent compounds in vivo. The concept of prodrug administration has been extensively reviewed (e.g. A. A. Sinkula in *Annual Reports in Medicinal Chemistry*, Vol 10, R. V. Heinzelman, Ed., Academic Press, New York London, 1975, Ch. 31, pp. 306-326), H. Ferres, *Drugs of Today*, Vol. 19, 499–538 (1983) and *J. Med. Chem.*, 18, 172 (1975). Examples of such prodrugs include the physiologically acceptable and metabolically labile ester derivatives, such as lower alkyl (e.g. methyl or ethyl esters), aryl (e.g. 5-indanyl esters), alkenyl (e.g. vinyl esters), alkoxyalkyl (e.g. methoxymethyl esters), alkylthioalkyl (e.g. methylthiomethyl esters), alkanoyloxyalkyl (e.g. pivaloyloxymethyl esters), and substituted or unsubstituted aminoethyl esters (e.g. 2-dimethylaminoethyl esters). Additionally, any physiologically acceptable equivalents of the compounds of general Formula I, similar to the metabolically labile esters, which are capable of producing the parent compounds of general Formula I in vivo, are within the scope of this invention.

Angiotensin II (AII) is a powerful arterial vasoconstrictor, and it exerts its action by interacting with specific receptors present on cell membranes. The compounds described in the present invention act as competitive antagonists of AII at the receptors. In order to identify AII antagonists and determine their efficacy in vitro, the following two ligand-receptor binding assays were established.

Receptor binding assay using rabbit aortae membrane preparation

Three frozen rabbit aortae (obtained from Pel-Freeze Biologicals) were suspended in 5 mM Tris-0.25M Sucrose, pH 7.4 buffer (50 ml) homogenized, and then centifuged. The mixture was filtered through a cheesecloth and the supernatant was centrifuged for 30 minutes at 20,000 rpm at 4° C. The pellet thus obtained was resuspended in 30 ml of 50 mM Tris-5 mM MgCl$_2$ buffer containing 0.2% Bovine Serum Albumin and 0.2 mg/ml Bacitration and the suspension was used for 100 assay tubes. Samples tested for screening were done in duplicate. To the membrane preparation (0.25 ml) there was added $^{125}$I-Sar$^1$Ile$^8$-angiotensin II [obtained from New England Nuclear] (10 ml; 20,000 cpm) with or without the test sample and the mixture was incubated at 37° C. for 90 minutes. The mixture was then diluted with ice-cold 50 mM Tris-0.9% NaCl, pH 7.4 (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration (IC$_{50}$) of potential AII antagonist which gives 50% displacement of the total specifically bound $^{125}$I-Sar$^1$Ile$^8$-angiotensin II was presented as a measure of the efficacy of such compounds as AII antagonists.

Receptor assay using Bovine adrenal cortex preparation

Bovine adrenal cortex was selected as the source of AII receptor. Weighed tissue (0.1 g is needed for 100 assay tubes) was suspended in Tris. HCl (50 mM), pH 7.7 buffer and homogenized. The homogenate was centrifuged at 20,000 rpm for 15 minutes. Supernatant was discarded and pellets resuspended in buffer [Na$_2$HPO$_4$ (10 mM)-NaCl (120 mM)-disodium EDTA (5 mM) containing phenylmethane sulfonyl fluoride (PMSF) (0.1 mM)]. (For screening of compounds, generally duplicates of tubes are used). To the membrane preparation (0.5 ml) there was added 3H-angiotensin II (50 mM) (10 ml) with or without the test sample and the mixture was incubated at 37° C. for 1 hour. The mixture was then diluted with Tris buffer (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration (IC$_{50}$) of potential AII antagonist which gives 50% displacement of the total specifically bound $^3$H-angiotensin II was presented as a measure of the efficacy of such compounds as AII antagonists.

Using the methodology described above, representative compounds of the invention were evaluated and were found to exhibit an activity of at least IC$_{50}$<50 mM thereby demonstrating and confirming the utility of the compounds of the invention as effective AII antagonists.

The potential antihypertensive effects of the compounds described in the present invention may be evaluated using the methodology described below: Male Charles River Sprague-Dawley rats (300–375 gm) were anesthetized with methohexital (Brevital; 50 mg/kg i.p.). The trachea was cannulated with PE 205 tubing. A stainless steel pithing rod (1.5 mm thick, 150 mm long) was inserted into the orbit of the right eye and down the spinal column. The rats were immediately placed on a Harvard Rodent Ventilator (rate—60 strokes per minute, volumn—1.1 cc per 100 grams body weight). The right carotid artery was ligated, both left and right vagal nerves were cut, the left carotid artery was cannulated with PE 50 tubing for drug administration, and body temperature was maintained at 37° C. by a thermostatically controlled heating pad which received input from a rectal temperature probe. Atropine (1 mg/kg i.v.) was then administered and 15 minutes later propranolol (1 mg/kg i.v.). Thirty minutes later antagonists of formula I were administered intravenously or orally. Angiotensin II was then typically given at 5, 10, 15, 30, 45 and 60 minute intervals and every half-hour thereafter for as long as the test compound showed activity. The change in the mean arterial blood pressure was recorded for each angiotensin II challenge and the percent inhibition of the angiotensin II response was calculated.

Thus, the compounds of the invention are useful in treating hypertension. They are also of value in the management of acute and chronic congestive heart failure. These compounds may also be expected to be useful in the treatment of secondary hyperaldosteronism, primary and secondary pulmonary hyperaldosteronism, primary and secondary pulmonary hypertension, renal failure such as diabetic nephropathy, glomerulonephritis, scleroderma, glomerular sclerosis, proteinuria of primary renal disease, end stage renal disease, renal transplant therapy, and the like, renal vascular hypertension, left ventricular dysfunction, diabetic retinapathy and in the management of vascular disorders such as migraine, Raynaud's disease, luminal hyperclasia, and to minimize the atherosclerotic process. The application of the compounds of this invention for these and similar disorders will be apparent to those skilled in the art.

The compounds of this invention are also useful to treat elevated intraocular pressure and to enhance retinal blood flow and can be administered to patients in need of such treatment with typical pharmaceutical formulations such as tablets, capsules, injectables and the like as will as topical ocular formulations in the form of solutions, ointments, inserts, gels, and the like. Pharmaceutical formulations prepared to treat intraocular pressure would typically contain about 0.1% to 15% by weight, preferably 0.5% to 2% by weight, of a compound of this invention.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg. per patient per day which can be administered in single or multiple doses. Preferably, the dosage range will be about 2.5 to 250 mg. per patient per day; more preferably about 2.5 to 75 mg. per patient per day.

The compounds of this invention can also be administered in combination with other antihypertensives and/or diuretics and/or angiotensin converting enzyme inhibitors and/or calcium channel blockers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, metolazone, metoprolol tartate, methyclothiazide, methyldopa, methyldopate hydrochloride, minoxidil, pargyline hydrochloride, polythiazide, prazosin, propranolol, rauwolfia serpentina, rescinnamine, reserpine, sodium nitroprusside, spironolactone, timolol maleate, trichlormethiazide, trimethophan camsylate, benzthiazide, quinethazone, ticrynafan, triamterene, acetazolamide, aminophylline, cyclothiazide, ethacrynic acid, furosemide, merethoxylline procaine, sodium ethacrynate, captopril, delapril hydrochloride, enalapril, enalaprilat, fosinopril sodium, lisinopril, pentopril, quinapril hydrochloride, ramapril, teprotide, zofenopril calcium, diflusinal, diltiazem, felodipine, nicardipine, nifedipine, niludipine, nimodipine, nisoldipine, nitrendipine, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 2.5-250 milligrams per day range can be effectively combined at levels at the 0.5-250 milligrams per day range with the following compounds at the indicated per day dose range: hydrochlorothiazide (15-200 mg) chlorothiazide (125-2000 mg), ethacrynic acid (15-200 mg), amiloride (5-20 mg), furosemide (5-80 mg), propranolol (20-480 mg), timolol maleate (5-60 mg.), methyldopa (65-2000 mg), felodipine (5-60 mg), nifedipine (5-60 mg), and nitrendipine (5-60 mg). In addition, triple drug combinations of hydrochlorothiazide (15-200 mg) plus amiloride (5-20 mg) plus angiotensin II antagonist of this invention (3-200 mg) or hydrochlorothiazide (15-200 mg) plus timolol maleate (5-60) plus an angiotensin II antagonist of this invention (0.5-250 mg) or hydrochlorothiazide (15-200 mg) and nifedipine (5-60 mg) plus an angiotensin II antagonist of this invention (0.5-250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The compounds of this invention are also useful to treat elevated intraocular pressure and can be administered to patients in need of such treatment with typical pharmaceutical formulations such as tablets, capsules, injectables, as well as topical ocular formulations in the form of solutions, ointments, inserts, gels and the like. Pharmaceutical formulations prepared to treat intraocular pressure would typically contain about 0.1% to 15% by weight, and preferably 0.5% to 2.0% by weight of a compound of this invention.

Thus, the compounds of the invention are useful in treating hypertension. They are also of value in the management of acute and chronic congestive heart failure, in the treatment of secondary hyperaldosteronism, primary and secondary pulmonary hypertension, renal failure such as diabetic nephropathy, glomerulonephritis, scleroderma, and the like, renal vascular hypertension, left ventricular dysfunction, diabetic retinopathy, and in the management of vascular disorders such as migraine or Raynaud's disease. The application of the compounds of this invention for these and similar disorders will be apparent to those skilled in the art.

The useful central nervous system (CNS) activities of the compounds of this invention are demonstrated and exemplified by the ensuing assays.

COGNITIVE FUNCTION ASSAY

The efficacy of these compounds to enhance cognitive function can be demonstrated in a rat passive avoidance assay in which cholinomimetics such as physostigmine and nootropic agents are known to be active. In this assay, rats are trained to inhibit their natural tendency to enter dark areas. The test apparatus used consists of two chambers, one of which is brightly illuminated and the other is dark. Rats are placed in the illuminated chamber and the elapsed time it takes for them to enter the darkened chamber is recorded. On entering the dark chamber, they receive a brief electric shock to the feet. The test animals are pretreated with 0.2 mg/kg of the muscarinic antagonist scopolamine which disrupts learning or are treated with scopolamine and the compound which is to be tested for possible reversal of the scopolamine effect. Twenty-four hours later, the rats are returned to the illuminated chamber. Upon return to the illuminated chamber, normal young rats who have been subjected to this training and who have been treated only with control vehicle take longer to re-enter the dark chamber than test animals who have been exposed to the apparatus but who have not received a shock. Rats treated with scopolamine before training do not show this hesitation when tested 24 hours later. Efficacious test compounds can overcome the disruptive effect on learning which scopolamine produces. Typically, compounds of this invention should be efficacious in this passive avoidance assay in the dose range of from about 0.1 mg/kg to about 100 mg/kg.

ANXIOLYTIC ASSAY

The anxiolytic activity of the invention compounds can be demonstrated in a conditioned emotional response (CER) assay. Diazepam is a clinically useful anxiolytic which is active in this assay. In the CER protocol, male Sprague-Dawley rats (250–350 g) are trained to press a lever on a variable interval (VI) 60 second schedule for food reinforcement in a standard operant chamber over weekly (five days per week) training sessions. All animals then receive daily 20 minute conditioning sessions, each session partitioned into alternating 5 minute light (L) and 2 minute dark (D) periods in a fixed L1D1L2D2L3 sequence. During both periods (L or D), pressing a lever delivers food pellets on a VI 60 second schedule: in the dark (D), lever presses also elicit mild footshock (0.8 mA, 0.5 sec) on an independent shock presentation schedule of VI 20 seconds. Lever pressing is suppressed during the dark periods reflecting the formation of a conditioned emotional response (CER).

Drug testing in this paradigm is carried out under extinction conditions. During extinction, animals learn that responding for food in the dark is no longer punished by shock. Therefore, response rates gradually increase in the dark periods and animals treated with an anxiolytic drug show a more rapid increase in response rate than vehicle treated animals. Compounds of this invention should be efficacious in this test procedure in the range of from about 0.1 mg/kg to about 100 mg/kg.

DEPRESSION ASSAY

The antidepressant activity of the compounds of this invention can be demonstrated in a tail suspension test using mice. A clinically useful antidepressant which serves as a positive control in this assay is desipramine. The method is based on the observations that a mouse suspended by the tail shows alternate periods of agitation and immobility and that antidepressants modify the balance between these two forms of behavior in favor of agitation. Periods of immobility in a 5 minute test period are recorded using a keypad linked to a microcomputer which allows the experimenter to assign to each animal an identity code and to measure latency, duration and frequency of immobile periods. Compounds of this invention should be efficacious in this test procedure in the range of from about 0.1 mg/kg to about 100 mg/kg.

SCHIZOPHRENIA ASSAY

The antidopaminergic activity of the compounds of this invention can be demonstrated in an apomorphine-induced sterotypy model. A clinically useful antipsychotic drug that is used as a positive control in this assay is haloperidol. The assay method is based upon the observation that stimulation of the dopaminergic system in rats produces stereo-typed motor behavior. There is a strong correlation between the effectiveness of classical neuroleptic drugs to block apomorphine-induced stereotypy and to prevent schizophrenic symptoms. Stereotyped behavior induced by apomorphine, with and without pretreatment with test compounds, is recorded using a keypad linked to a microcomputer. Compounds of the invention should be efficacious in this assay in the range of from about 0.1 mg/kg to about 100 mg/kg.

In the treatment of the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 5 to 6000 mg. per patient per day which can be administered in single or multiple doses. Preferably, the dosage range will be about 10 to 4000 mg. per patient per day; more preferably about 20 to 2000 mg. per patient per day.

In order to obtain maximal enhancement of cognitive function, the compounds of this invention may be combined with other cognition-enhancing agents. These include acetylcholinesterase inhibitors such as heptylphysostigmine and tetrahydroacridine (THA; tacrine), muscarinic agonists such as oxotremorine, inhibitors of angiotensin-converting enzyme such as octylramipril, captopril, ceranapril, enalapril, lisinopril, fosinopril and zofenopril, centrally-acting calcium channel blockers and as nimodipine, and nootropic agents such as piracetam.

In order to achieve optimal anxiolytic activity, the compounds of this invention may be combined with other anxiolytic agents such as alprazolam, lorazepam, diazepam, and busipirone.

In order to achieve optimal antidepressant activity, combinations of the compounds of this invention with other antidepressants are of use. These include tricyclic antidepressants such as nortriptyline, amitryptyline and trazodone, and monoamine oxidase inhibitors such as tranylcypromine.

In order to obtain maximal antipsychotic activity, the compounds of this invention may be combined with other antipsychotic agents such as promethazine, fluphenazine and haloperidol.

The following examples illustrate the preparation of the compounds of formula (I) and their incorporation into pharmaceutical compositions and as such are not to be considered as limiting the invention set forth in the claims appended hereto. All $^1$H-NMR spectra were recorded on a Varian XL-300 Fourier transform spectrometer or on a Bruker 250 MHz spectrometer. Chemical shifts are reported as (parts per million) downfield from tetramethyl silane. Mass spectra were obtained from the Merck and Co. mass spectral facility in Rahway N.J. Analytical TLC was conducted on E.M. Merck precoated silica plates (0.25 mm in glass, Kieselgel 60 F254) with UV visualization. All chromatography was conducted on E.M. Merck silica gel. All reactions were carried out under an atmosphere of dry nitrogen under standard conditions for those skilled in the art.

PREPARATION OF INTERMEDIATES

2-t-BUTOXYCARBONYL-4'-METHYLBIPHENYL

To a solution of p-bromotoluene (30 g) in dry ether (150 ml) at −78° C., a solution of t-BuLi in pentane (1.7M) (210 ml) was added slowly over a period of 1.5 hr using a dropping funnel. The bath was then removed and the mixture was stirred at room temperature for an additional 2 hours. The content of the flask was then added slowly (using a cannula) at room temperature to a premixed solution of $ZnCl_2$ in ether (1M, 180 ml) and dry THF (360 ml). The mixture was stirred for 2 hr at that temperature and then the slurry was added (using a cannula) to a solution of 2-t-butoxycarbonyl iodobenzene (35.6 g) and $NiCl_2(Ph_3P)_2$ (2.1 g) in dry THF (360 ml). The mixture, after stirring at room temperature overnight (18 hr), was poured slowly under stirring into ice-cold 0.5N HCl (1500 ml). The organic layer was separated, and the aqueous phase was extracted with ether (3×300 ml). The combined organic layer was washed with water, brine and then dried over $MgSO_4$. Removal of the solvent gave the crude product as an oil (32 g). The material was purified on a silica-gel flash column using ethyl acetate-hexane (1:12) to give the titled compound as an oil (24 g, 76%). $^1H$ NMR ($CDCl_3$): δ1.24 (s, 9H) 2.42 (s, 3H), 7.2–7.8 (m, 8H); FAB-MS: m/e 269(M+H).

4-BROMOMETHYL-2'-t-BUTOXYCARBONYL-BIPHENYL

To a solution of 2-t-butoxycarbonyl-4'-methylbiphenyl (25.3 g, 95 mmol) in $CCl_4$ (200 ml) were added freshly opened N-bromosuccinimide (17.6 g, 0.099 mole) and dibenzoyl peroxide (2.28 g, 0.0094 moles). The mixture was refluxed for 4 hours, cooled to room temperature and filtered. The filtrate was washed with sat. $NaHSO_3$ (1×50 ml), sat. $NaHCO_3$ (1×50 ml), water (1×50 ml), sat. NaCl (1×50 ml) and dried over $MgSO_4$. The solution was filtered and concentrated in vacuo. The residue was dissolved in 100 ml of hot hexane. Crystallization gradually took place as the solution cooled. The flask was finally cooled to −20° C. and the precipitate recovered by filtration. The solid was washed with ice cold hexanes and dried in vacuo to give 27 g (88%) of a white solid. $^1$H-NMR ($CDCl_3$): 1.23 (s, 9H), 4.53 (s, 2H), 7.2–7.5 (m, 7H), 7.68 (d, 1H).

2-CYANO-4'-METHYLBIPHENYL

To a solution of p-bromotoluene (30 g) in dry ether (150 ml) at −78° C., a solution of t-BuLi in pentane (1.7M) (210 ml) was added slowly over a period of 1.5 hr, using a dropping funnel. The bath was then removed and the mixture was stirred at room temperature for an additional 2 hr. The contents of the flask was then added slowly (using a cannula) at room temperature to a premixed solution of $ZnCl_2$ in ether (1M) (180 ml) and dry THF (360 ml). The mixture was stirred for 2 h at that temperature and then the slurry was added (using a cannula) to a solution of 2-bromobenzonitrile (21.3 g) and $NiCl_2(Ph_3P)_2$ (2.1 g) in dry THF (300 ml). The mixture, after stirring at room temperature overnight (18 h), was poured slowly under stirring into ice-cold 1N HCl (1500 ml). The organic layer was separated, and the aqueous phase was extracted with ether (3×300 ml). The combined organic layer was washed with water, brine and then dried over $MgSO_4$. Removal of the solvent gave the crude product as a semisolid mass (34 g). The material was purified on a silica-gel flash column using ethyl acetate-hexane (1:12) to give the desired nitrile as a low-melting solid (28 g, 88%). $^1H$ NMR ($CDCl_3$): 2.42 (s, 3H), 7.2–7.8 (m, 8H); FAB-MS: m/e 194 (M++1).

TRIMETHYLSTANNYL AZIDE

To a concentrated solution of $NaN_3$ (1.2 kg, 18.5 moles) in water (3 L), a solution of trimethyltin chloride (600 g, 3 moles) in dioxane (400 ml) was added in three portions under vigorous stirring. A precipitate formed instantaneously. The mixture, after stirring overnight at room temperature, was filtered. The residue was washed with water and dried under suction and then in vacuo over $P_2O_5$. Yield 541 g (88%), mp 120°–122° C.

5-[2-(4'-METHYLBIPHENYL)]TETRAZOLE

To a solution of 2-cyano-4'-methylbiphenyl (390 g, 2.02 moles) in toluene (2.3 L) was added trimethyltin azide (525 g, 2.55 moles) at r.t. The mixture was refluxed for 24 h, cooled to r.t., filtered, washed with toluene and sucked dry in a funnel. The precipitate was resuspended in toluene (3.5 L) and THF (250 mL) was added. Anhydrous HCl was bubbled in at a moderate rate at r.t. to give a clear solution (45 min). Addition of HCl gas was continued for another 20 min. with stirring whereupon a white precipitate formed. The reaction mixture was stirred over night. The solid product was filtered, washed with toluene followed with ether and then dried under vacuum. This produced 250 g (53% yield of the tetrazole. m.p. 152°–154° C.; $^1$H-NMR ($CDCl_3$): 2.40 (s, 3H), 7.19 (dd, 1H), 7.55 (m, 2H), 8.25 (dd, 1H).

N-TRIPHENYLMETHYL-5-[2-(4'-METHYLBIPHENYL)]TETRAZOLE

To a cloudy solution of 5-[2-(4'-methylbiphenyl)]tetrazole (250 g (1.06 mole) in $CH_2Cl_2$ (4 L) was added triphenylmethylchloride (310 g 1.11 mole) at r.t. The reaction mixture was stirred and triethylamine (190 mL, 138 g, 1.36 mole) was added portionwise. After addition, the mixture was stirred at reflux for 90 min. The solution was cooled to r.t., washed with water (2×1 L) and dried over $MgSO_4$, filtered through a silica gel plug and concentrated on the rotovap to a solid. This was crystallized from toluene to give the product as an off-white solid (425 g, 84%); m.p. 166°–168° C.; $^1$H-NMR ($CDCl_3$): 2.28 (s, 3H), 6.9–7.05 (m, 10H), 7.2–7.5 (m, 12H), 7.9 (dd, 1H).

N-TRIPHENYLMETHYL-5-[2-(4'-BROMOMETHYLBIPHENYL)]TETRAZOLE

To a solution of N-triphenylmethyl-5-[2-(4'-methylbiphenyl)]tetrazole (425 g, 0.89 moles) in $CCl_4$ (4.0 L) were added N-bromsuccinimide (159 g, 0.89 mole) and dibenzoyl peroxide (22 g, 0.089 moles). The mixture was refluxed for 2 hours, cooled to room temperature and filtered. The filtrate was concentrated in vacuo to give a thick oil. The addition of ether (2.0 L) to this oil resulted in a clear solution. Crystallization, followed by filtration, gave a white solid (367 g, 74%). m.p. 137°–139.5° C.; $^1$H-NMR ($CDCl_3$): 4.38 (s, 2H), 6.9–8.0 (m, 23H).

2-NITRO-4'-METHYLBIPHENYL

A solution of 5.0 g (19.6 mmol) 4-(trimethylstannyl)-toluene, 4.08 g (20.2 mmol) 1-bromo-2-nitrobenzene, and 138 mg (0.2 mmol) bis(triphenylphosphine)palladium(II) chloride in 100 mL DMF was heated to 110° C. for 4 hours. The mixture was cooled to room temperature, was poured into a mixture of brine and 1N KOH, then was extracted 3 times with ether. The combined organic material was washed with 1N KOH, was washed with brine, was dried over magnesium sulfate, was stripped of solvent in vacuo, and was chromatographed on silica gel under medium pressure using 5% ethyl acetate in hexanes to give 3.76 g (90% yield) of the title compound as a light lemon-yellow colored oil. Rf 0.31 in 10% EtOAc/hexane, visualized by UV and ammonium molybdate/ceric sulfate stain.

1H-NMR (400 MHz, CDCl3): δ7.82 (4 line m, 1H), 7.60 (6 line m, 1H), 7.44 (m, 2H), 7.23 (m, 4H), 2.40 (s, 3H).

4'-BROMOMETHYL-2-NITROBIPHENYL

A solution/suspension of 3.74 g (17.5 mmol) 2-nitro-4'-methylbiphenyl, 123 mg (0.9 mmol) AIBN, and 3.43 g (19.3 mmol) NBS in 180 mL CCl4 was refluxed for 30 minutes. The mixture was cooled to room temperature, was filtered through a medium fritted funnel, was washed with water, was dried over magnesium sulfate, was stripped of solvent in vacuo, and was chromatographed on silica gel under medium pressure using 7% ethyl acetate in hexanes to give 4.71 g (92% yield) of the title compound as a light yellow crystalline solid. Rf 0.21 in 10% EtOAc/hexane, visualized by UV and ammonium molybdate/ceric sulfate stain. 1H-NMR (400 MHz, CDCl3): δ7.88 (m, 1H), 7.63 (m, 2H), 7.52 (m, 1H), 7.45 (m, 2H), 7.31 (m, 2H), 4.54 (s, 2H); a small singlet at d 6.69 (benzylic proton) is observed for for the dibrominated material.

EXAMPLE 1

3-Cyclopropyl-3-oxopropanenitrile

To a mechanically stirred solution of 15.0 g (176 mmol) 2-cyanoacetic acid and 100 mg 1,10-phenanthroline in 500 mL THF at −78° C. was added 141 mL (352 mmol) 2.5M n-butyllithium in hexanes. The solution was warmed in a water bath to 0° C. After 15 minutes at 0° C. most of the brown color had faded. The mixture was cooled to −78° C. and to it was added a solution of 8.0 mL (88 mmol) cyclopropanecarbonyl chloride in 8 mL THF. The mixture was warmed to RT and stirred 15 minutes, was poured into 300 mL 5% HCl solution in water, and was extracted three times with ether. The combined organic material was washed with saturated aqueous sodium bicarbonate then with brine, was dried over magnesium sulfate, was stripped of solvent in vacuo, and was chromatographed on silica gel under medium pressure using 30% ethyl acetate in hexanes to give 6.5 g (54% yield) of the title compound. The title compound was stored with 1% w/w BHT in 40 mL CH2Cl2 at −5° C. Rf 0.12 in 20% EtOAc/hexane visualized by ninhydrin stain (green tint); 1H-NMR (300 MHz, CDCl3): δ3.63 (s, 2H), 2.10 (m, 1H), 1.20 (m, 2H), 1.10 (m, 2H).

EXAMPLE 2

3-Oxoheptanenitrile

The title compound was prepared similarly to the example above. The title compound was isolated as a clear oil, 6.32 g, 60% yield. Rf 0.18 in 20% EtOAc/hexane, visualized by ninhydrin stain; 1H-NMR (300 MHz, CDCl3): δ3.46 (s, 2H), 2.62 (3 line m, 2H), 1.61 (m, 2H), 1.35 (m, 2H), 0.92 (t, J=7.3 Hz, 3H); 13C-NMR (75.4 MHz, CDCl3): δ197.6, 113.8, 41.9, 31.9, 25.3, 22.0, 13.7.

EXAMPLE 3

3-Oxohexanenitrile

This material was prepared similarly to the examples above. The title compounds was isolated as a clear oil. Rf 0.22 in 25% EtOAc/hexane, visualized by ninhydrin stain.

EXAMPLE 4

3-Oxohexanenitrile

This material was prepared similarly to the examples above. The title compounds was isolated as a clear oil, 13.8 g, 39% yield. Rf 0.20 in 30% EtOAc/hexane, visualized by ninhydrin stain; 1H-NMR (300 MHz, CDCl3): δ3.49 (s, 2H), 2.68 (q, 2H), 1.15 (t, 3H).

EXAMPLE 5

2-[(2'-(N-triphenylmethyl-tetrazol-5-yl)biphen-4-yl)methyl]-3-oxoheptanenitrile To a solution of 1.80 g (14.4 mmol) 3-oxoheptanenitrile in 80 mL DMSO was added 1.15 g (28.7 mmol) 60% NaH in oil. After 30 minutes, 4.00 g (7.18 mmol) N-triphenylmethyl-5-[2-(4'-bromomethylbiphenyl)]tetrazole was added all at once to the solution. After 3 hours the solution was poured into brine. An indicator quantity of phenolphthalein was added followed by HOAc just until the pink color disappeared. The mixture was extracted 3 times with ether. The combined organic material was washed with saturated aqueous NaHCO3 then with brine, was dried over MgSO4, was stripped of solvent in vacuo, and was chromatographed on silica gel under medium pressure using 15% EtOAc/hexane to give 2.08 g (48% yield) of the title compound as a white foam. Rf 0.23 in 20% EtOAc/hexane, visualized by UV and ammonium molybdate/ceric sulfate stain; 1H-NMR (300 MHz, CDCl3): δ7.93 (m, 1H), 7.47 (10 line m, 2H), 7.40–7.20 (m, 10H), 7.04 (m, 4H), 6.90 (m, 6H), 3.44 (X of ABX, 1H), 3.03 (AB of ABX, $J_{AB}$=13.8 Hz, $J_{AX}$=8.6 Hz, $J_{BX}$=5.3 Hz, Δν=43.5 Hz, 2H), 2.59 (sym. 12 line m, 2H), 1.55 (m, 2H), 1.28 (m, 2H), 0.88 (t, J=7.3 Hz, 3H).

EXAMPLE 6

3-Cyclopropyl-3-oxo-2-[(2'-(N-triphenylmethyltetrazol-5-yl)biphen-4-yl)methyl]propanenitrile To a solution of 1.18 g (10.8 mmol) 3-cyclopropyl-3-oxopropanenitrile in 80 mL DMSO was added 861 mg (21.5 mmol) 60% NaH in oil. After 1 hour, 3.00 g (5.38 mmol) N-triphenylmethyl-5-[2-(4'-bromomethylbiphenyl)]tetrazole was added all at once to the solution. After 3 hours, the solution was poured into brine and extracted 3 times with ether. The combined organic material was dried over MgSO4, stripped of solvent in vacuo, and was chromatographed on silica gel under medium pressure using 20% EtOAc/hexane. The title compound was isolated as a white foam, 2.36 g, 75% yield. Rf 0.23 in 25% EtOAc/hexane, visualized by UV and ammonium molybdate/ceric sulfate stain;

1H-NMR (300 MHz, CDCl3): δ7.91 (m, 1H), 7.53–7.15 (overlapping m's, 12H), 7.13–6.84 (m, 10H), 3.58 (X of ABX, 1H), 3.05 (AB of ABX, 2H), 2.13 (m, 1H), 1.14 (m, 2H), 1.03 (m, 2H).

EXAMPLE 7

2-Cyclopropyl-5,7-dimethyl-3-[(2'-(tetrazol-5-yl)biphen-4-yl)methyl]pyrazolo[1,5-a]pyrimidine To a solution of 1.21 g (2.06 mmol) 3-cyclopropyl-2-[(2'-(N-triphenylmethyl-tetrazol-5-yl)biphen-4-yl)methyl]-3-oxopropanenitrile in 20 mL ethanol was added 0.196 mL (6.18 mmol) anhydrous hydrazine. The mixture was refluxed for five hours then was stripped of solvent in vacuo. The crude material was exposed to 0.1 Torr for one hour to give a light yellow foam then was redissolved in 20 mL DMF. To the solution was added 0.706 mL (12.3 mmol) acetic acid and 1.27 mL (12.4 mmol) 2,4-pentanedione. The solution was heated to 120° C. for 6 hours then was cooled to RT and diluted with brine. The mixture was extracted 3 times with ether then the aqueous material was discarded. The combined organic material was extracted twice with 5% aqueous NaOH solution then the organic layer was discarded. The combined aqueous extracts were washed once with ether. An indicator quantity of phenolphthalein was added to the aqueous material followed by concentrated HCl just until the pink color disappeared. A few drops of 10% NaOH was added just until the pink color returned then 4 mL acetic acid was added. The mixture was extracted twice with a combination of ether/methylene chloride then twice with just ether. The combined organic material was dried over $MgSO_4$ and decolorized with activated charcoal, was filtered through a powdered cellulose filter aid, was stripped of solvent in vacuo, then was chromatographed on silica gel under medium pressure using 1/50/49 acetic acid/ethyl acetate/hexanes then again on silica gel under medium pressure uding 1/15/84 concentrated ammonium hydroxide/methanol/methylene chloride. The purified material was stripped of solvent in vacuo, was converted to foam at 0.1 Torr, was crushed to a powder with a spatula, then was exposed to 0.1 Torr overnight to remove traces of ammonia. A final weight of 314 mg (36% yield) of the title compound was obtained. $R_f$ 0.23 in 1/15/84 concentrated ammonium hydroxide/methanol/methylene chloride, visualized by UV and ammonium molybdate/ceric sulfate stain;

$^1$H-NMR (300 MHz, DMSO): δ7.59–7.45 (m, 2H), 7.45–7.35 (m, 2H), 7.14–6.94 (4 line m, 4H), 6.71 (s, 1H), 4.08 (s, 2H), 2.56 (s, 3H), 2.46 (s, 3H), 2.02 (m, 1H), 0.90 (m, 4H); MS (FAB) m/e 422 (M+1).

EXAMPLE 8

2-Cyclopropyl-7-methyl-3-[(2'-(tetrazol-5-yl)biphen-4-yl)methyl]-5-(trifluoromethyl)pyrazolo[1,5-a]pyrimidine The title compound was prepared similarly to the example above beginning with 1.17 g (2.00 mmol) 3-cyclopropyl-2-[(2'-(N-triphenylmethyl-tetrazol-5-yl)biphen-4-yl)methyl]-3-oxopropanenitrile. The title compound was purified by medium pressure chromatography on silica gel using 1/14/85 concentrated ammonium hydroxide/methanol/methylene chloride and was isolated as an amorphous solid, 504 mg, 53% yield. $R_f$ 0.13 in 1/12/87 concentrated ammonium hydroxide/methanol/methylene chloride, visualized by UV;

$^1$H-NMR (300 MHz, CD$_3$OD): δ7.59–7.48 (m, 2H), 7.48–7.38 (m, 2H), 7.16–6.95 (4 line m, 4H), 7.12 (s, 1H), 4.18 (s, 2H), 2.62 (s, 3H), 1.94 (m, 1H), 0.95 (m, 4H); MS (FAB) m/e 476 (M+1).

EXAMPLE 9

2-Cyclopropyl-3-[(2'-(tetrazol-5-yl)biphen-4-yl)methyl]-5,7-bis(trifluoromethyl)pyrazolo[1,5-a]pyrimidine The title compound was prepared similarly to the examples above beginning with 1.17 g (2.00 mmol) 3-cyclopropyl-2-[(2'-(N-triphenylmethyl-tetrazol-5-yl)biphen-4-yl)methyl]-3-oxopropanenitrile. The title compound was chromatographed on silica gel under medium pressure using 1/33/66 acetic acid/ethyl acetate/hexanes then again on silica gel under medium pressure using 1/10/89 concentrated ammonium hydroxide/methanol/methylene chloride and was isolated as a canary yellow amorphous solid after exposure to 0.1 Torr overnight at 80° C., 434 mg (41% yield). Rf 0.21 in 1/15/84 concentrated ammonium hydroxide/methanol/methylene chloride, visualized by UV;

$^1$H-NMR (300 MHz, CDCl$_3$): δ8.23 (m, 1H), 7.56 (m, 2H), 7.46–7.13 (4 line m, 4H), 7.31 (s, 1H), 7.25 (m, 1H), 4.38 (s, 2H), 2.07 (m, 1H), 1.16 (m, 2H), 1.10 (m, 2H); MS (FAB) m/e 530 (M+1).

EXAMPLE 10

5-(trimethylstannyl)toluene

To a solution of 21.5 g (100 mmol) trimethyltin chloride in 500 mL THF at −35° C. was added 113 mL (113 mmol) 1.0M p-tolylmagnesium bromide over 3 minutes. The mixture was allowed to warm to RT and stir for 1 hour after which time was added saturated aqueous ammonium chloride. The mixture was extracted three times with ether. The comined organic material was washed with brine, was dried over $MgSO_4$, was stripped of solvent in vacuo, then was distilled at 0.1 Torr with the title compound distilling between 66°–74° C. The bitolyl remaining in the still pot crystallized upon cooling. The title compound was isolated as a clear, shiny liquid, 25.4 (92% yield).

EXAMPLE 11

N-tert-butyl-2-bromobenzenesulfonamide

To a solution of 4.0 g (16 mmol) 2-bromobenzenesulfonyl chloride in 75 mL methylene chloride at 0° C. was added 3.7 mL (35 mmol) tert-butylamine. The mixture was allowed to warm to RT and stir for 1 hour. The mixture was poured into aqueous 5% HCl and extracted three times with ether. The combined organic material was dried over $MgSO_4$, was stripped of solvent in vacuo, then was recrystallized from hexane/acetone to give 3.19 g (70% yield) of the title compound. $R_f$ 0.17 in 10% EtOAc/hexane, visualized by UV;

$^1$H-NMR (300 MHz, CDCl$_3$): δ8.17 (m, 1H), 7.72 (m, 1H), 7.50–7.33 (m, 2H), 5.12 (s, 1H), 1.22 (s, 9H).

EXAMPLE 12

N-tert-butyl-4'-methyl-2-sulfonamidobiphenyl

A solution of 3.19 g (10.9 mmol) N-tert-butyl-2-bromobenzenesulfonamide, 2.97 g (11.7 mmol) 5-(trimethylstannyl)toluene, and 153 mg (0.218 mmol) (Ph$_3$P)$_2$PdCl$_2$ in 50 mL DMF was heated to 120° C. for 4 hours. The mixture was diluted with brine and concentrated aqueous NH$_4$OH solution then was extracted 3 times with ether. The combined organic material was washed with 5% aqueous NaOH solution then with brine. The organic material was treated with 1 mL HOAc, was stripped of solvent in vacuo, was stripped from toluene, then was recrystallized from hexanes/CH$_2$Cl$_2$ to give 2.13 g (64% yield) of the title compound as white crystals. A second crop of crystals was obtained but was contaminated with the bromobenzenesulfonamide starting material. This material was set aside for future purification. R$_f$ 0.17 in 7% EtOAc/hexane, visualized by UV and ammonium molybdate/ceric sulfate stain;

$^1$H-NMR (300 MHz, CDCl$_3$): δ8.16 (m, 1H), 7.59–7.22 (m, 7H), 3.56 (s, 1H), 2.42 (s, 3H), 0.99 (s, 9H).

EXAMPLE 13

4'-Bromomethyl-N-tert-butyl-2-sulfonamidobiphenyl

A solution/suspension of 2.12 g (6.99 mmol) N-tert-butyl-4'-methyl-2-sulfonamidobiphenyl, 1.37 g (7.69 mmol) NBS, and 49 mg (0.35 mmol) AIBN in 70 mL CCl$_4$ was refluxed for ~90 minutes. The resulting mixture was filtered through a fritted funnel, washed twice with water, then was purified by medium pressure chromatography on silica gel using 10% EtOAc/hexane to give 1.61 g (60% yield) of the title compound. R$_f$ 0.10 in 10% EtOAc/hexane, visualized by UV and ammonium molybdate/ceric sulfate stain.

EXAMPLE 14

3-Cyclopropyl-3-oxo-2-[(2'-(N-tert-butylsulfonamido)-biphen-4-yl)methyl]propanenitrile To a solution of 303 mg (2.77 mmol) 3-cyclopropyl-3-oxopropanenitrile in 7 mL DMSO was added 116 mg (2.91 mmol) 60% NaH in oil. After 10 minutes, 530 mg (1.39 mmol) 4'-bromomethyl-N-tert-butyl-2-sulfonamidobiphenyl was added in ~3 mL DMSO. After stirring at RT for 1 hour, the mixture was poured into brine and extracted three times with ether. The organic material was dried over MgSO$_4$, stripped of solvent in vacuo, and was chromatographed on silica gel under medium pressure using 25% EtOAc/hexane to give 480 mg (84% yield) of the title compound. R$_f$ 0.17 in 30% EtOAc/hexane, visualized by UV and ammonium molybdate/ceric sulfate stain; $^1$H-NMR (300 MHz, CDCl$_3$): δ8.18 (m, 1H), 7.61–7.27 (overlapping m's, 7H), 3.86 (X of ABX, 1H), 3.50 (s, 1H), 3.26 (AB of ABX, 2H), 2.28 (m, 1H), 1.21 (m, 2H), 1.13 (m, 2H), 1.00 (s, 9H).

EXAMPLE 15

2-Cyclopropyl-5,7-dimethyl-3-[(2'-sulfonamidobiphen-4-yl)methyl]pyrazolo[1,5-a]pyrimidine A solution of 480 mg (1.17 mmol) 3-cyclopropyl-3-oxo-2-[(2'-(N-tert-butylsulfonamido)biphen-4-yl)methyl]propanenitrile and 0.632 mL (19.9 mmol) anhydrous hydrazine in 15 mL ethanol was refluxed for five hours then was stripped of solvent in vacuo. The crude material was exposed to 0.1 Torr for one hour to give a light yellow foam then was redissolved in 15 mL DMF. To the solution was added 0.796 mL (13.9 mmol) acetic acid and 1.43 mL (13.9 mmol) 2,4-pentanedione. The solution was heated to 120° C. for 6 hours then was cooled to RT and diluted with brine. The mixture was extracted 3 times with ether. The combined organic material was dried over MgSO$_4$ and was stripped of solvent in vacuo. The product mixture contained both the title compound and the tert-butyl protected sulfonamide 2-cyclopropyl-5,7-dimethyl-3-[(2'-(N-tert-butylsulfonamido)biphen-4-yl)methyl]pyrazolo[1,5-a]pyrimidine. The mixture was fully deprotected by dissolving the mixture in 7 mL TFA and stirred overnight at RT. TFA was removed in vacuo, the crude material was purified by medium pressure chromatography on silica gel using 40% EtOAc/hexane to give 136 mg (27% yield) of the title compound. R$_f$ 0.13 in 40% EtOAc/hexane, visualized by UV;

$^1$H-NMR (300 MHz, CDCl$_3$): δ8.10 (m, 1H), 7.59–7.21 (m, 7H), 6.42 (s, 1H), 4.25 (s, 2H), 4.12 ((NH$_2$) s, 2H), 2.62 (s, 3H), 2.51 (s, 3H), 1.92 (m, 1H), 0.98 (m, 2H), 0.91 (m, 2H).

EXAMPLE 16

2-Cyclopropyl-5,7-dimethyl-3-[(2'-(N-benzoylsulfonamido)biphen-4-yl)methyl]pyrazolo[1,5-a]pyrimidine To a solution of 136 mg (0.314 mmol) 2-cyclopropyl-5,7-dimethyl-3-[(2'-sulfonamidobiphen-4-yl)methyl]pyrazolo[1,5-a]pyrimidine in 5 mL DMF was added 26 mg (0.660 mmol) 60% NaH in oil. After 10 minutes, 0.047 mL (0.409) benzoyl chloride was added. After 30 minutes, the mixture was poured into brine followed by 1 mL of acetic acid. The mixture was extracted 3 times with ether. The combined organic material was washed with brine, was dried over MgSO$_4$, was stripped of solvent in vacuo, and was chromatographed on silica gel under medium pressure using 1/9/90 concentrated ammonium hydroxide/methanol/methylene chloride to give 66 mg (39% yield) of the title compound. R$_f$ 0.10 in 20% 1/8/91 concentrated ammonium hydroxide/methanol/methylene chloride, visualized by UV;

$^1$H-NMR (300 MHz, CDCl$_3$): δ8.17 (m, 1H), 7.60 (m, 2H), 7.46 (m, 1H), 7.38–7.23 (m, 5H), 7.15 (m, 4H), 6.47 (s, 1H), 4.21 (s, 2H), 2.68 (s, 3H), 2.54 (s, 3H), 1.95 (m, 1H), 1.04 (m, 2H), 0.96 (m, 2H); MS (FAB) m/e 537 (M+1).

EXAMPLE 17

3-Cyclopropyl-3-oxo-2-[(2'-nitrobiphen-4-yl)methyl]propanenitrile

To a solution of 2.61 g (24.0 mmol) 3-cyclopropyl-3-oxopropanenitrile in 150 mL DMSO was added 1.01 g (25.2 mmol) 60% NaH in oil. After 1 hour, 3.50 g (12.0 mmol) 4'-bromomethyl-2-nitrobiphenyl was added all at once to the solution. After 3 hours, the solution was poured into brine and extracted 3 times with ether. The combined organic material was dried over MgSO4, stripped of solvent in vacuo, and was chromatographed on silica gel under medium pressure using 3/40/57 EtOAc/CH2Cl2/hexanes to give 1.29 g (34% yield) of the title compound as a yellow glass. Rf 0.13 in 3/40/57 EtOAc/CH2Cl2/hexanes, visualized by UV and ammonium molybdate/ceric sulfate stain; Rf of the dialkylated material is 0.19 in the same solvent mixture.

$^1$H-NMR (400 MHz, CDCl13): δ7.87 (4 line m, 1H), 7.63 (6 line m, 1H), 7.50 (m, 1H), 7.44 (4 line m, 1H), 7.32 (m, 4H), 3.84 (X of ABX, 1H), 3.25 (AB of ABX, 2H), 2.19 (m, 1H), 1.18 (m, 2H), 1.08 (m, 2H).

EXAMPLE 18

2-Cyclopropyl-7-methyl-5-methylthio-3-[(2'-nitrobiphen-4-yl)methyl]pyrazolo[1,5-a]pyrimidine A solution of 11.1 g (34.7 mmol) 3-cyclopropyl-3-oxo-2-[(2'-nitrobiphen-4-yl)methyl]propanenitrile and 4.0 mL (126 mmol) hydrazine in 400 mL dry ethanol was refluxed for 4 hours. The mixture was cooled to room temperature then stripped of solvent in vacuo.

The resulting foam was kept under vacuum overnight (final weight 11.8 g) then was redissolved in 600 mL acetic acid along with 1 mL piperidine and 9.14 g (56.4 mmol) 1,1-bis(methylthio)but-1-en-3-one. The mixture was heated to 90° C. for 5 hours, was cooled to room temperature, was stripped of solvent in vacuo, then was stripped from toluene. The crude material was chromatographed on silica gel under medium pressure using 10% ethyl acetate in hexanes to give 2.50 g (17% yield) of the title compound as a light yellow crystalline solid. Rf 0.24 in 20% EtOAc/hexane, visualized by UV, iodine, and ammonium molybdate/ceric sulfate stain.

1H-NMR (400 MHz, CDCl3): δ7.81 (4 line m, 1H), 7.58 (6 line m, 1H), 7.43 (m, 2H), 7.38 (m, 2H), 7.20 (m, 2H), 6.38 (s, 1H), 4.21 (s, 2H), 2.59 (s, 3H), 2.58 (s, 3H), 1.96 (m, 1H), 0.99 (m, 2H), 0.94 (m, 2H). MS (FAB) m/e 431 (M+1).

EXAMPLE 19

2-Cyclopropyl-7-methyl-5-methylsulfonyl-3-[(2'-nitrobiphen-4-yl)methyl]pyrazolo[1,5-a]pyrimidine A solution of 2.40 g (5.57 mmol), 2.4 mL (23 mmol) hydrogen peroxide was warmed to 55° C. for 9 hours. The mixture was cooled to room temperature, was stripped of solvent in vacuo, was stripped from toluene, then was used without further purification. Rf 0.24 in 20% EtOAc/hexane, visualized by UV, iodine, and ninhydrin stain.

1H-NMR (400 MHz, CDCl3): characteristic peaks-δ4.30 (s, 2H), 3.29 (s, 3H), 2.80 (s, 3H).

EXAMPLE 20

2-Cyclopropyl-7-methyl-5-cyano-3-[(2'-nitrobiphen-4-yl)methyl]pyrazolo[1,5-a]pyrimidine A suspension of 3.0 g (61 mmol) NaCN in 400 mL DMSO was heated to 55° C. until all of the NaCN dissolved. The mixture was cooled to room temperature and a solution of the crude product from the above reaction Example 19 in DMSO was added. The mixture was warmed to 50° C. for 1 hour. The mixture was cooled to room temperature then poured into crushed ice and water. The mixture was extracted three times with ether. The combined organic material was dried over MgSO4, stripped of solvent in vacuo, and was used without further purification. Obtained 1.85 g crude title compound (81% crude yield over two steps). Rf 0.60 in 35% EtOAc/hexane, visualized by UV, iodine, ninhydrin, and ammonium molybdate/ceric sulfate stain.

1H-NMR (400 MHz, CDCl3): δ7.82 (4 line m, 1H), 7.59 (6 line m, 1H), 7.44 (m, 2H), 7.33 (2 line m, 2H), 7.22 (2 line m, 2H), 6.84 (s, 1H), 4.30 (s, 2H), 2.75 (s, 3H), 2.04 (m, 1H), 1.08 (m, 2H), 1.04 (m, 2H).

EXAMPLE 21

Methyl 2-cyclopropyl-7-methyl-3-[(2'-nitrobiphen-4-yl)methyl]pyrazolo[1,5-a]pyrimidine-5-carboxylate A solution of 1.80 g 2-cyclopropyl-7-methyl-5-cyano-3-[(2'-nitrobiphen-4-yl)methyl]pyrazolo[1,5-a]pyrimidine in 350 mL dry methanol was cooled to 0° C. HCl gas was bubbled through for 30 minutes. The ice bath was removed and the mixture was allowed to stir overnight. To the mixture was added 0.8 mL water. After 2 hours the mixture was cooled in an ice bath and saturated sodium bicarbonate solution was added slowly until basic. The solution was extracted 4 times with ether. The aqueous layer was saturated with sodium chloride then extracted twice with methylene chloride. The combined organic material was dried over MgSO4, stripped of solvent in vacuo, and was used without further purification. Obtained 1.59 g crude title compound (82% crude yield). Rf 0.63 in 50% EtOAc/hexane, visualized by UV, iodine, and ninhydrin stain.

1H-NMR (400 MHz, CDCl3): δ7.80 (4 line m, 1H), 7.59 (6 line m, 1H), 7.42 (m, 2H), 7.35 (s, 1H), 7.33 (2 line m, 2H), 7.20 (2 line m, 2H), 4.37 (s, 2H), 4.01 (s, 3H), 2.76 (s, 3H), 1.97 (m, 1H), 1.05 (m, 2H), 0.98 (m, 2H). MS (FAB) m/e 443 (M+1).

EXAMPLE 22

Methyl 2-cyclopropyl-7-methyl-3-[(2'-aminobiphen-4-yl)methyl]pyrazolo[1,5-a]pyrimidine-5-carboxylate A solution/suspension of 1.59 g methyl 2-cyclopropyl-7-methyl-3-[(2'-nitrobiphen-4-yl)methyl]pyrazolo[1,5-a]pyrimidine-5-carboxylate and/0.5 g Raney Nickel in 30 mL methanol and 150 mL THF was stirred under 1 atm hydrogen for 2.5 hours. The mixture was filtered through Celite, stripped of solvent in vacuo, then was chromatographed on silica gel under medium pressure using 10% ethyl acetate in hexanes to give 2.50 g (17% yield) of the title compound as a light yellow crystalline solid. Rf 0.24 in 20% EtOAc/hexanes, visualized by UV, iodine, and ammonium molybdate/ceric sulfate stain.

1H-NMR (400 MHz, CDCl3): δ7.32 (m, 5H), 7.11 (m, 2H), 6.80 (6 line m, 1H), 6.74 (4 line m, 1H), 4.37 (s, 2H), 4.02 (s, 3H), 3.73 (br s, 2H), 2.76 (s, 3H), 2.02 (m, 1H), 1.09 (m, 2H), 0.99 (m, 2H). MS (FAB) m/e 413 (M+1).

EXAMPLE 23

2-Cyclopropyl-7-methyl-3-[(-2'-(((trifluoromethyl)sulfonyl)amino)biphen-4-yl)methyl]pyrazolo[1,5-a]pyrimidine-5-carboxylic acid To a solution of 78 mg (0.189 mmol) methyl 2-cyclopropyl-7-methyl-3-[(2'-aminobiphen-4-yl)methyl]pyrazolo[1,5-a]pyrimidine-5-carboxylate and 312 mg (1.52 mmol) 2,6-di-t-butyl-4-methylpyridine in 10 mL methylene chloride at 0° C. was added 0.128 mL (0.761 mmol) trifluoromethanesulfonic anhydride in 0.5 mL methylene chloride. After 20 minutes the mixture was diluted with 20 mL methylene chloride, was made basic with 5% sodium bicarbonate solution, was reacidified with acetic acid, then was extracted 3 times with methylene chloride. The combined organic material was dried over MgSO4, stripped of solvent in vacuo, was stripped from toluene, then was chromatographed on silica gel under medium pressure using 20% EtOAc/hexanes to give 110 mg (86% yield) of methyl 2-cyclopropyl-7-methyl-3-[(-2'-(bis((trifluoromethyl)sulfonyl)amino)biphen-4-yl)methyl]pyrazolo[1,5-a]pyrimidine-5-carboxylate. Rf 0.42 in 35% EtOAc/hexanes, visualized by UV, iodine, and ammonium molybdate/ceric sulfate stain. MS (FAB) m/e 677 (M+1).

To a solution of 110 mg of the product from above in 30 mL methanol was added 5 mL 2.5N NaOH. The mixture stirred for 15 minutes (until clear). Phenolphthalein was added and acidified with concentrated HCl until colorless. The mixture was further acidified with several mL acetic acid. The volatile organics were removed in vacuo and the crude material was repartitioned between water and methylene chloride. The aqueous layer was extracted twice more with methylene chloride. The combined organic material was dried over MgSO4, stripped of solvent in vacuo, then was chromatographed on silica gel under medium pressure using 1/3/96 HOAc/MeOH/CH2Cl2 to give 79 mg of the title compound (92% yield). Rf 0.15 in 1/5/94 HOAc/MeOH/CH2Cl2, visualized by UV, iodine, and ammonium molybdate/ceric sulfate stain.

1H-NMR (400 MHz, CDCl3): δ7.61 (d, J=7.9 Hz, 1H), 7.43 (s, 1H), 7.38 (m, 3H), 7.27 (m, 4H), 4.35 (s, 2H), 2.81 (s, 3H), 2.06 (m, 1H), 1.14 (m, 2H), 1.07 (m, 2H).

MS (FAB) m/e 531 (M+1).

EXAMPLE 25

Methyl 2-cyclopropyl-7-methyl-3-[(-2'-(((trifluoromethyl)sulfonyl)amino)biphen-4-yl)methyl]pyrazolo[1,5-a]pyrimidine-5-carboxylate To a solution of 273 mg 2-cyclopropyl-7-methyl-3-[(-2'-(((trifluoromethyl)sulfonyl)amino)biphen-4-yl)methyl]pyrazolo[1,5-a]pyrimidine-5-carboxylic acid in 150 mL methanol was added 5 g Amberlyst-15. The mixture was heated to 60° C. for 9 hours (overnight generally preferred). After cooling to room temperature, 5 mL pyridine was added and the mixture was stirred for 30 minutes. The mixture was filtered, was stripped of solvent in vacuo, was stripped from toluene, then was chromatographed on silica gel under medium pressure using 1/1/98 HOAc/MeOH/CH2Cl2 to give 91 mg of the title compound (32% yield) as a yellow solid. Rf 0.58 in 1/3/96 HOAc/MeOH/CH2Cl2, visualized by white light, UV, iodine, and ammonium molybdate/ceric sulfate stain.

1H-NMR (400 MHz, CDCl3): δ7.61 (d, J=8.3 Hz, 1H), 7.42 (2 line m, 2H), 7.38 (m, 1H), 7.35 (s, 1H), 7.23 (m, 4H), 4.40 (s, 2H), 4.02 (s, 3H), 2.77 (s, 3H), 2.00 (m, 1H), 1.09 (m, 2H), 1.01 (m, 2H). MS (FAB) m/e 545 (M+1).

EXAMPLE 26

3-[(2'-carboxybiphen-4-yl)methyl]-6,8-dimethyl-2-ethyl imidazo[1,2-b]pyridazine

Step A: Preparation of ethyl (2-ethyl-6,8-dimethylimidazo[1,2-b]pyridazin-3-yl)carboxylate.

To a suspension of 0.598 g (4.86 mmol) of 3-amino-4,6-dimethylpyridazine in 10 mL of CH2Cl2 in a high pressure vessel was added 0.941 g (1.27 mL; 7.28 mmol) of diisopropylethylamine and 1.301 g (7.28 mmol) of ethyl a-chloropropionylacetate. The reaction mixture was equipped with a magnetic stir bar, tightly sealed, then heated and stirred in an oil bath at 75° C. for 16 hours. The flask was then cooled to room temperature, opened and the reaction mixture was evaporated in vacuo. The residue was partitioned between EtOAc and water, and the organic layer was separated. The organic layer was washed with brine, dried (MgSO4), filtered and evaporated. The residual brown solid was purified on a silica gel flash chromatography column eluted with 50% EtOAc-hexane. Combination of the purified fractions and evaporation in vacuo afforded 0.874 g (73%) of the title compound.

1H NMR (300 MHz, CDCl3, ppm): δ1.32 (t, J=7.6 Hz, 3H), 1.42 (t, J=8.0 Hz, 3H), 2.58 (s, 3H), 2.60 (s, 3H), 3.10 (q, J=7.6 Hz, 2H), 4.44 (q, J=8.0 Hz, 2H), 6.86 (s, 1H).

FAB-MS: m/e 248 (M+1).

Step B: Preparation of 2-ethyl-6,8-dimethyl-3-hydroxymethylimidazo[1,2-b]pyridazine To a solution of 2.702 g (10.9 mmol) of the product of Step A dissolved in 21 mL of anhydrous THF was added 6.0 mL of a 1.0M solution of lithium aluminum hydride in THF at 0° C., and the reaction mixture was stirred under a nitrogen atmosphere. After 1 hour TLC analysis (75% EtOAc-hexane) indicated complete reduction of the ester, and the reaction mixture was quenched by stepwise addition of 0.23 mL water, 0.23 mL of 15% sodium hydroxide solution, and finally 0.69 mL of water. The reaction mixture was filtered and the filtrate was evaporated in vacuo. The residual oil was redissolved in EtOAc and dried (MgSO4), filtered, evaporated and dried in vacuo to afford 1.884 g (84%) of a tan solid which was used in the next step without further purification.

1H NMR (300 MHz, CDCl3, ppm): δ1.32 (t, J=7.6 Hz, 3H), 2.49 (s, 3H), 2.58 (s, 3H), 2.83 (q, J=7.6 Hz, 2H), 2.95 (t, J=8 Hz, 1H), 4.98 (d, J=8 Hz, 2H), 6.70 (s, 1H).

FAB-MS: m/e 206 (M+1).

Step C: Preparation of 2-ethyl-6,8-dimethylimidazo[1,2-b]pyridazin-3-carboxaldehyde To a solution of 0.886 g (4.32 mmol) of the product of Step B dissolved in 15 mL of CH2Cl2 was added 1.772 g of powdered 4A molecular sieves and 4.430 g (51 mmol) of manganese dioxide and the reaction mixture was magnetically stirred at room temperature. After 16 h, TLC analysis (50% EtOAc-hexane) indicated complete reaction and the mixture was filtered. The filtrate was concentrated in vacuo, and the residue was redissolved in 50% EtOAc-hexane and purified by filtration through a short plug of silica gel. Evaporation of the filtrate and drying in vacuo afforded 0.781 g (89%) of the title compound as a tan solid.

1H NMR (400 MHz, CDCl3, ppm): δ1.33 (t, J=7.6 Hz, 3H), 2.57 (s, 3H), 2.62 (s, 3H), 3.11 (q, J=7.6 Hz, 2H), 6.95 (s, 1H), 10.42 (s, 1H). FAB-MS: m/e 204 (M+1).

Step D: Preparation of 1-(2-ethyl-6,8-dimethylimidazo[1,2-b]pyridazin-3-yl)-1-(4-hydroxyphenyl)-methanol.

A 100 mL three necked round bottom flask equipped with a magnetic stir bar, septum, reflux condenser and a nitrogen inlet was dried and charged with 0.608 g (25 mmol) of magnesium turnings and 15 mL of dry THF. A solution of 7.182 g (25 mmol) of the t-butyldimethylsilylether derived from 4-bromophenol dissolved in 10 mL of dry THF was added via syringe and the reaction mixture was stirred at reflux for 3 hours. A separate 50 mL flask equipped with a magnetic stir bar, septum and containing a solution of 0.747 g (3.7 mmol) of the product of Step C was stirred at 0° C. in an ice-water bath. The Grignard reaction mixture was cooled to 35° C. and 5 mL (5 mmol) of the approximately 1.0M solution was transferred to the second reaction mixture via syringe. The reaction mixture was stirred at 0° C. for 30 min, at which point TLC analysis (50% EtOAc-hexane) indicated complete reaction of the aldehyde. The reaction mixture was quenched with 10% aqueous sodium bisulfate, then partitioned between THF and saturated brine. The organic layer was separated, evaporated in vacuo, redissolved in THF, dried (MgSO4), filtered and concentrated to an oil. The residual oil was again redissolved in 10 mL THF and treated with 5 mL of a 1.0M solution of tetra-n-butylammonium fluoride in THF. After stirring 1 h at room temperature the reaction mixture was evaporated in vacuo, and the residual oil was purified by filtration through a short plug of silica gel eluted with THF. The filtrate was concentrated and the product was precipitated from THF/hexane to afford 0.896 g (82%) of title compound as an off-white crystalline solid.

$^1$H NMR (400 MHz, CDCl$_3$/10% CD$_3$OD, ppm): δ1.04 (t, J=7.6 Hz, 3H), 2.35 (s, 3H), 2.42 (, 3H), 2.53 (m, 2H), 6.16 (s, 1H), 6.60 (s, 1H), 6.63 (d, J=8.8 Hz, 2H), 7.09 (d, J=8.8 Hz, 2H). FAB-MS: m/e 298 (M+1).

Step E: Preparation of 4-[(2-ethyl-6,8-dimethylimidazo[1,2-b]pyridazin-3-yl)methyl]phenol To a stirred suspension of 2.607 g (8.8 mmol) of the product of Step D and 5.257 g (35.1 mmol) of sodium iodide in 12 mL of acetonitrile was added 2.13 mL (17.5 mmol) of dichlorodimethylsilane via syringe under a nitrogen atmosphere. The reaction mixture which immediately darkened was stirred for 20 min at room temperature, then partitioned between EtOAc and brine. The organic layer was washed with aqueous sodium bicarbonate, 10% aqueous sodium thiosulfate, then dried (MgSO$_4$), filtered and evaporated. The residue was crystallized from EtOAc-hexane to afford 2.214 g (90%) of the title compound as a pale yellow solid.

$^1$H NMR (400 MHz, CD$_3$OD, ppm): δ1.25 (t, J=7.6 Hz, 3H), 2.56 (s, 3H), 2.59 (s, 3H), 2.84 (q, J=7.6 Hz, 2H), 4.26 (s, 2H), 6.66 (d, J=8.8 Hz, 2H), 7.05 (d, J=8.8 Hz, 2H), 7.18 (s, 1H). FAB-MS: m/e 282 (M+1).

Step F: Preparation of 4-[(2-ethyl-6,8-dimethylimidazo[1,2-b]pyridazin-3-yl)methyl]phenyl triflate To a magnetically stirred solution of 1.006 g (3.6 mmol) of the product of Step E dissolved in 18 mL of dry pyridine at 0° C. was added 0.9 mL (1.513 g, 5.4 mmol) of trifluoromethanesulfonic anhydride under a nitrogen atmosphere. The reaction mixture was stirred at 0° C. for 15 minutes, allowed to warm to room temperature and stirred an additional 2 hours. The pyridine was removed in vacuo, and the residue was dissolved in EtOAc. The organic layer was washed twice with 1N hydrochloric acid, saturated aqueous sodium bicarbonate and finally brine, then dried (MgSO$_4$), filtered and evaporated. The residue was purified on a silica gel flash chromatography column eluted with 50% EtOAc-hexane. Evaporation of the purified fractions and drying in vacuo afforded 1.448 g (98%) of the title compound as an off-white crystalline solid.

$^1$H NMR (400 MHz, CDCl$_3$, ppm): δ1.26 (t, J=7.6 Hz, 3H), 2.46 (s, 3H), 2.58 (s, 3H), 2.79 (q, J=7.6 Hz, 2H), 4.32 (s, 2H), 6.66 (s, 1H), 7.12 (d, J=8.4 Hz, 2H), 7.28 (d, J=8.4 Hz, 2H). FAB-MS: m/e 414 (M+1).

Step G: Preparation of 4-[(2-ethyl-6,8-dimethylimidazo[1,2-b]pyridazin-3-yl)methyl]phenyltrimethylstannane To a solution of 1.390 g (3.4 mmol) of the product of Step F, 1.652 g (5.0 mmol) of hexamethylditin, and 0.194 g (5 mol %) tetrakis(triphenylphosphine)palladium(0) dissolved in 13.5 mL of 1,4-dioxane was added 0.855 g (20.2 mmol) of anhydrous lithium chloride. The reaction mixture was degassed, flushed with nitrogen, then magnetically stirred under a nitrogen atmosphere at 60° C. for 24 hours. At this point the reaction was cooled to room temperature, the dioxane was removed in vacuo, and the residue was partitioned between EtOAc and water. The organic layer was extracted, washed with brine, dried (MgSO$_4$), filtered and evaporated. The residual oil was purified on a silica flash chromatography eluted with 35% EtOAc-hexane to afford after concentration and drying in vacuo, 0.677 g (47%, 84% based on recovered starting material) of the title compound as a yellow oil. Further elution of the column with 35% EtOAc-hexane afforded 0.612 g (44%) of recovered starting material.

$^1$H NMR (400 MHz, CDCl$_3$, ppm): δ0.22 (s, 9H), 1.28 (t, J=7.6 Hz, 3H), 2.47 (s, 3H), 2.59 (s, 3H), 2.82 (q, J=7.6 Hz, 2H), 4.29 (s, 2H), 6.64 (s, 1H), 7.21 (d, J=8.0 Hz, 2H), 7.36 (d, J=8.0 Hz, 2H). FAB-MS: m/e 428 (M+1, $_{50}$Sn$^{118}$).

Step H: Preparation of t-butyl 2-[4-[(2-ethyl-6,8-dimethylimidazo[1,2-b]pyridazin-3-yl)methyl]phenyl]benzoate To a solution of 0.149 g (0.35 mmol) of the product of Step G and 0.132 g (0.43 mmol) of t-butyl 2-iodobenzoate in 1 mL of anhydrous DMF was added 5 mg of bis(triphenylphosphine)palladium(II) chloride. The mixture was degassed, flushed with nitrogen, then magnetically stirred under a nitrogen atmosphere for 12 hours at 100° C. The reaction mixture was cooled to room temperature, then partitioned between EtOAc and water. The organic layer was extracted, separated, dried (MgSO$_4$), filtered and evaporated. The residue was purified on a silica gel flash chromatography column eluted with 50% EtOAc-hexane. Evaporation of the purified fractions and drying in vacuo afforded 0.111 g (73%) of the title compound as an off-white amorphous solid.

$^1$H NMR (400 MHz, CDCl$_3$, ppm): δ1.12 (s, 9H), 1.31 (t, J=7.6 Hz, 3H), 2.47 (s, 3H), 2.61 (s, 3H), 2.86 (q, J=7.6 Hz, 2H), 4.36 (s, 2H), 6.67 (s, 1H), 7.17 (d, J=8.4 Hz, 2H), 7.23 (d, J=8.4 Hz, 2H), 7.26 (dd, J=1.2, 7.8 Hz, 1H), 7.33 (dt, J=1.6, 7.6 Hz, 1H), 7.43 (dt, J=1.6, 7.6 Hz, 1H), 7.72 (dd, J=1.2, 8.0 Hz, 1H). FAB-MS: m/e 442 (M+1).

Step I: Preparation of 3-[(2'-carboxybiphen-4-yl)methyl]-6,8-dimethyl-2-ethylimidazo[1,2-b]pyridazine To a solution of 0.111 g (0.25 mmol) of the product of Step H and 0.055 g (0.51 mmol) of anisole dissolved in 0.25 mL of methylene chloride was added 0.4 mL of trifluoroacetic acid and the reaction mixture was stirred under a nitrogen atmosphere at room temperature for 14 hours. The reaction mixture was then evaporated in vacuo and purified on a silica gel flash chromatography column eluted with CHCl$_3$-MeOH-NH$_4$OH (80:15:1). Evaporation of the purified fractions and drying in vacuo afforded 0.083 g (86%) of the title compound as a white amorphous solid.

$^1$H NMR (400 MHz, CD$_3$OD, ppm): δ1.26 (t, J=7.6 Hz, 3H), 2.49 (s, 3H), 2.54 (s, 3H), 2.81 (q, J=7.6 Hz, 2H), 4.34 (s, 2H), 6.86 (s, 1H), 7.21 (d, J=8.0 Hz, 2H), 7.25-7.35 (m, 3H), 7.34 (d, J=8.0 Hz, 2H), 7.52 (dd, J=1.6, 7.6 Hz, 1H).

FAB-MS: m/e 386 (M+1).

EXAMPLE 27

6,8-Dimethyl-2-ethyl-3-[(2'-(tetrazol-5-yl)biphen-4-yl)methyl]imi azo[1,2-b]pyridazine Step A: Preparation of 6,8-dimethyl-2-ethyl-3-[(2'-cyanobiphen-4-yl)methyl]-5,7-dimethyl-2-imidazo[1,2-b]pyridazine To a solution of 0.313 g (0.73 mmol) of the product of Step G in Example 1 and 0.200 g (1.1 mmol) of 2-bromobenzonitrile dissolved in 3 mL of anhydrous DMF was added 10 mg of bis(triphenylphosphine)palladium(II) chloride. The mixture was degrassed, flushed with nitrogen, then magnetically stirred under a nitrogen atmosphere for 12 hours at 100° C. The reaction mixture was then cooled to room temperature, partitioned between EtOAc and water. The organic layer was extracted, separated, dried (MgSO₄), filtered and evaporated. The residue was purified on a silica gel flash chromatography column eluted with 50% EtOAc-hexane. Evaporation of the purified fractions and drying in vacuo afforded 0.226 g (83%) of the title compound as a white amorphous solid.

$^1$H NMR (400 MHz, CDCl₃, ppm): δ1.29 (t, J=7.6 Hz, 3H), 2.48 (s, 3H), 2.59 (s, 3H), 2.83 (q, J=7.6 Hz, 2H), 4.37 (s, 2H), 6.65 (s, 1H), 7.33 (d, J=8.0 Hz, 2H), 7.37 (dt, J=1.6, 7.8 Hz, 1H), 7.41–7.45 (m, 1H), 7.42 (d, J=8.0 Hz, 2H), 7.58 (dt, J=1.6, 7.8 Hz, 1H), 7.71 (dd, J=1.6, 7.6 Hz, 1H). FAB-MS: m/e 367 (M+1).

Step B: Preparation of 6,8-dimethyl-2-ethyl-3-[(2'-(tetrazol-5-yl)biphen-4-yl)methyl]imidazo[1,2-b]pyridazine A 20 mL heavy walled pressure tube was equipped with a magnetic stir-bar and charged with a solution of 0.226 g (0.60 mmol) of the product of Step A, 1.2 mL of anhydrous toluene and 0.373 g (1.8 mmol) of trimethyltin azide. The reaction mixture was dissolved, degassed, flushed with nitrogen, then tightly sealed and stirred at 125° C. for 12 hours. At the end of this period, the reaction mixture was cooled to room temperature, and evaporated in vacuo. The residue was purified on a silica gel flash chromatography column eluted with CHCl₃—MeOH—NH₄OH (80:15:1). Evaporation of the purified fractions and drying in vacuo afforded 0.142 g (57%) of the title compound as a white amorphous solid.

$^1$H NMR (400 MHz, CD₃OD, ppm): δ1.23 (t, J=7.6 Hz, 3H), 2.51 (s, 3H), 2.57 (s, 3H), 2.80 (q, J=7.6 Hz, 2H), 4.34 (s, 2H), 6.99 (s, 1H), 7.00 (d, J=8.0 Hz, 2H), 7.15 (d, J=8.0 Hz, 2H), 7.48–7.51 (m, 2H), 7.59–7.62 (m, 2H). FAB-MS: m/e 410 (M+1).

EXAMPLE 28

6,8-Dimethyl-2-ethyl-3-[(2'-trifluoromethanesulfonylamino)biphen-4-yl)methyl]imidazo[1,2-b]pyridazine Step A: Preparation of 6,8-dimethyl-2-ethyl-3-[(2'-nitrobiphen-4-yl)methyl]-5,7-dimethyl-1,2-imidazo[1,2-b]pyridazine To a solution of 0.220 g (0.51 mmol) of the product of Step G in Example 1 and 0.104 g (0.51 mmol) of 2-bromonitrobenzene dissolved in 2 mL of anhydrous DMF was added 11 mg of bis(triphenylphosphine)palladium(II) chloride. The mixture was degassed, flushed with nitrogen, then magnetically stirred under a nitrogen atmosphere for 14 hours at 100° C. The reaction mixture was then cooled to room temperature, partitioned between EtOAc and water. The organic layer was extracted, separated, dried (MgSO₄), filtered and evaporated. The residue was purified on a silica gel flash chromatography column eluted with 50% EtOAc-hexane. Evaporation of the purified fractions and drying in vacuo afforded 0.147 g (74%) of the title compound as a white amorphous solid.

$^1$H NMR (400 MHz, CDCl₃, ppm): δ1.28 (t, J=7.6 Hz, 3H), 2.48 (s, 3H), 2.60 (s, 3H), 2.82 (q, J=7.6 Hz, 2H), 4.35 (s, 2H), 6.66 (s, 1H), 7.18 (d, J=8.0 Hz, 2H), 7.27 (d, J=8.0 Hz, 2H), 7.38 (d, J=8.4 Hz, 1H), 7.42 (dt, J=1.2, 7.0 Hz, 1H), 7.55 (dt, J=1.2, 7.2 Hz, 1H), 7.78 (dd, J=1.2, 8.0 Hz, 1H). FAB-MS: m/e 387 (M+1).

Step B: Preparation of 6,8-dimethyl-2-ethyl-3-[(2'-aminobiphen-4-yl)methyl]-5,7-dimethyl-1-2-imidazo[1,2-b]pyridazine A 50 mL Parr hydrogenation vessel was charged with 0.147 g (0.38 mmol) of the product of Step A, 10 mL of ethanol and 40 mg of a 10% palladium on powdered carbon catalyst. The flask was mounted in a Parr hydrogenation apparatus and the reaction mixture was shaken under a hydrogen atmosphere (45 psig) for 20 minutes. At the end of this period, the reaction mixture was removed from the Parr apparatus, filtered and evaporated in vacuo to afford 0.132 g (97%) of the title compound which was used directly in the next step without further purification.

$^1$H NMR (400 MHz, CDCl₃, ppm): δ1.29 (t, J=7.6 Hz, 3H), 2.49 (s, 3H), 2.61 (s, 3H), 2.85 (q, J=7.6 Hz, 2H), 3.60–3.80 (br s, 2H), 4.35 (s, 2H), 6.67 (s, 1H), 6.72 (dd, J=1.2, 8.0 HZ, 1H), 6.77 (dt, J=1.2, 7.0 Hz, 1H), 7.06 (dd, J=1.2, 7.0 Hz, 1H), 7.11 (dt, J=1.2, 7.0 Hz, 1H), 7.27–7.33 (m, 4H). FAB-MS: m/e 357 (M+1).

Step C: Preparation of 6,8-dimethyl-2-ethyl-3-[(2'(trifluoromethanesulfonylamino)biphen-4-yl)-methyl]imidazo[1,2-b]pyridazine A 0.1–0.5M solution of the product of Step B in anhydrous pyridine is magnetically stirred under a nitrogen atmosphere at 0° C. The reaction mixture is treated dropwise with 1.2 equivalents of trifluoromethanesulfonic anhydride and stirring is continued for about 2 hours. The reaction mixture is then warmed to room temperature, the pyridine is removed in vacuo and the residue is partitioned between EtOAc and water. The organic layer is separated, washed several times with 1.0N hydrochloric acid, then 5% aqueous sodium bicarbonate, dried (MgSO₄), filtered and evaporated. The product may be purified by chromatography on silica gel.

EXAMPLE 29

6,8-Dimethyl-2-ethyl-3-[(2'-(N-benzoylsulfonamido)biphen-4-yl)methyl]imidazo[1,2-b]pyridazine Step A: Preparation of 6,8-dimethyl-2-ethyl-3-[(2'-(N-t-butylsulfonamido)biphen-4-yl)methyl]-5,7-dimethyl-2-imidazo[1,2-b]pyridazine To a solution of 0.336 g (0.78 mmol) of the product of Step G in Example 1 and 0.229 g (0.51 mmol) of N-t-butyl-2-bromobenzenesulfonamide dissolved in 3 mL of anhydrous DMF was added 30 mg of bis(triphenylphosphine)palladium(II) chloride. The mixture was degassed, flushed with nitrogen, then magnetically stirred under a nitrogen atmosphere for 12 hours at 100° C. The reaction mixture was then cooled to room temperature, partitioned between EtOAc and water. The organic layer was extracted, separated, dried (MgSO₄), filtered and evaporated. The residue was purified on a silica gel flash chromatography column eluted with 50% EtOAc-hexane. Evaporation of the purified fractions and drying in vacuo afforded 0.104 g (28%) of the title compound as an amorphous white solid.

$^1$H NMR (400 MHz, CDCl₃, ppm): δ0.90 (s, 9H), 1.36 (t, J=7.6 Hz, 3H), 2.53 (s, 3H), 2.60 (s, 3H), 2.93 (q, J=7.6 Hz, 2H), 4.37 (s, 2H), 7.25–7.34 (m, 1H), 7.28 (d, J=8.0 Hz, 2H), 7.29–7.52 (m, 3H), 7.32 (d, J=8.0 Hz, 2H), 8.14 (d, J=8.0 Hz, 1H).

Step B: Preparation of 6,8-dimethyl-2-ethyl-3-[(2'-(sulfonamido)biphen-4-yl)methyl]-5,7-dimethyl-2-imidazo[1,2-b]pyridazine The product of Step A is reacted with trifluoroacetic acid in a suitable solvent such as methylene chloride and in the presence of 1-2 equivalents of anisole for about 24 hours at room temperature. The reaction mixture is diluted with methylene chloride and washed with water, and then several times with 5% aqueous sodium bicarbonate. The organic layer is next dried (MgSO4), filtered and evaporated. The product may be purified on a silica gel flash chromatography column eluted with an appropriate solvent system. Evaporation of the purified fractions and drying in vacuo affords the title compound.

Step C: Preparation of 6,8-Dimethyl-2-ethyl-3-[(2'-(N-benzoylsulfonamido)biphen-4-yl)methyl]imidazo[1,2-b]pyridazine An oven-dried round bottom flask equipped with a magnetic stir bar and a nitrogen inlet is charged with benzoic acid (1.25 equivalents) and dissolved in anhydrous THF to a final concentration of about 0.5M. The reaction mixture is degassed, stirred under a nitrogen atmosphere, and 1,1'-carbonyldiimidazole (1.25 equivalents) is added. The mixture is next stirred at reflux for several hours, then cooled to room temperature. The product of Step B (1 equivalent) is then added, followed by addition of a base such as 1,4-diazabicyclo[5.4.0]undec-7-ene (1.25 equivalents). The reaction mixture is stirred again at reflux for an additional 6-24 hours, then cooled to room temperature and evaporated in vacuo. The residue is purified by chromatography on silica gel eluted with an appropriate solvent system. Evaporation of the purified fractions and drying in vacuo affords the title compound.

EXAMPLE 30

2-[4-[(2-ethyl-6,8-dimethylimidazo[1,2-b]pyridazin-3-yl)methyl]phenoxy]phenylacetic acid Step A: Preparation of methyl 2-[4-[(2-ethyl-6,8-dimethylimidazo[1,2-b]pyridazin-3-yl)methyl]phenoxy]phenylacetate To a solution of 0.108 g (0.38 mmol) of the product of Step E of Example 1 dissolved in 4 mL of acetone was added 0.132 g (0.58 mmol) of methyl a-bromophenylacetate and 0.106 g (0.78 mmol) of powdered potassium carbonate. The reaction mixture was stirred and gently refluxed for 12 hours, then cooled to room temperature, filtered and evaporated. The residual oil was purified on a silica gel flash chromatography column eluted with 20% EtOAc-CH$_2$Cl$_2$. Evaporation of the purified fractions and drying in vacuo afforded 0.063 g (38%) of the title compound as a glassy solid.

$^1$H NMR (400 MHz, CDCl$_3$, ppm): δ1.23 (t, J=7.6 Hz, 3H), 2.45 (s, 3H), 2.56 (s, 3H), 2.76 (q, J=7.6 Hz, 2H), 3.69 (s, 3H), 4.21 (s, 2H), 5.55 (s, 1H), 6.60 (s, 1H), 6.79 (d, J=8.8 Hz, 2H), 7.11 (d, J=8.8 Hz, 2H), 7.30-7.38 (m, 3H), 7.50-7.54 (m, 2H). FAB-MS: m/e 430 (M+1).

Step B: Preparation of 2-[4-[(2-ethyl-6,8-dimethylimidazo[1,2-b]pyridazin-3-yl)methyl]phenoxy]phenylacetic acid To a solution of 0.063 g (0.15 mmol) of the product of Step F dissolved in 2 mL of methanol was added 0.2 mL of a 5.0N sodium hydroxide solution. The reaction mixture was stirred at room temperature and monitored by TLC (CHCl$_3$-MeOH-NH$_4$OH, 80:15:1). After 3 hours the reaction mixture was adjusted to pH=6 with 1.0N hydrochloric acid, then evaporated in vacuo. The residue was then purified on a silica gel flash chromatography column eluted with CHCl$_3$-MeOH-NH$_4$OH (80:15:1). The purified fractions were combined, evaporated, and dried in vacuo to afford 0.039 g (63%) of the title compound as a pale yellow amorphous solid.

$^1$H NMR (400 MHz, CD$_3$OD, ppm): δ1.22 (t, J=7.6 Hz, 3H), 2.50 (s, 3H), 2.55 (s, 3H), 2.78 (q, J=7.6 Hz, 2H), 4.88 (s, 2H), 5.50 (s, 1H), 6.85 (d, J=8.8 Hz, 2H), 6.96 (s, 1H), 7.11 (d, J=8.8 Hz, 2H), 7.25-7.34 (m, 3H), 7.54-7.57 (m, 2H). FAB-MS: m/e 416 (M+1).

EXAMPLE 31

2-[4-[(2-ethyl-6,8-dimethylimidazo[1,2-b]pyridazin-3-yl)methyl]phenoxy]-2-(2-methylphenyl)acetic acid Step A: Preparation of 2-[4-[(2-ethyl-6,8-dimethylimidazo[1,2-b]pyridazin-3-yl)methyl]phenoxy]-2-(2-methylphenyl)acetic acid To a suspension of 0.050 g (0.18 mmol) of the product of Example 1, Step E and 0.049 g (0.35 mmol) of potassium carbonate in 1 mL of acetone was added 0.052 g (0.21 mmol) of methyl 2-bromo-2-(2-methylphenyl)acetate and the reaction mixture was stirred and heated at reflux for 15 hours. At the end of this period TLC analysis (50% EtOAc-hexane) revealed only starting materials in the reaction mixture. Dimethylformamide (1 mL) and a second portion of potassium carbonate (0.050 g, 0.36 mmol) were added to the reaction mixture and the reaction was stirred and heated at 80° C. for an additional 15 hours. At the end of this period, TLC analysis indicated a complete reaction and formation of a more polar product than the anticipated methyl ester. The reaction mixture was evaporated in vacuo, and the residue was purified on a silica gel flash chromatography column eluted with CHCl$_3$-MeOH-NH$_4$OH (80:15:1). The purified fractions were combined, evaporated, and dried in vacuo to afford 0.088 g (78%) of the title carboxylic acid as an amorphous solid.

$^1$H NMR (400 MHz, CD$_3$OD, ppm): δ1.22 (t, J=7.6 Hz, 3H), 2.44 (s, 3H), 2.52 (s, 3H), 2.57 (s, 3H), 2.79 (q, J=7.6 Hz, 2H), 4.28 (s, 2H), 5.77 (s, 1H), 6.83 (d, J=8.8 Hz, 2H), 7.04 (s, 1H), 7.11 (d, J=8.8 Hz, 2H), 7.13-7.28 (m, 3H), 7.47 (d, J=7.2 Hz, 1H). FAB-MS: m/e 430 (M+1).

EXAMPLE 32

2-[4-[(2-ethyl-6,8-dimethylimidazo[1,2-b]pyridazin-3-yl)methyl]phenoxy]-2-(2-chlorophenyl)acetic acid Step A: Preparation of methyl 2-[4-[(2-ethyl-6,8-dimethylimidazo[1,2-b]pyridazin-3-yl)methyl]phenoxy]-2-(2-chlorophenyl)acetate A 10 mL round bottom flask equipped with a magnetic stir bar and a reflux condenser was charged with 0.050 g (0.18 mmol) of the product of Step E in Example 1, 0.049 g (0.35 mmol) of potassium carbonate, 0.056 g (0.21 mmol) of methyl 2-bromo-2-(2-chlorophenyl)acetate and 1 mL of dimethylformamide. The reaction mixture was stirred and heated at 60° C. for 15 hours at which point TLC analysis (50% EtOAc-hexane) indicated remaining phenol. A second portion of methyl 2-bromo-2-(2-chlorophenyl)acetate (0.050 g; 0.19 mmol) and 0.050 g (0.36 mmol) of potassium carbonate were added and the reaction was heated at 90° C. for an additional 15 hours. At this point TLC analysis revealed complete reaction and the mixture was cooled to room temperature and evaporated in vacuo. The residue was purified on a silica gel flash chromatography column eluted with 50% EtOAc-hexane. The purified fractions were combined, evaporated and dried in vacuo to afford 0.044 g (53%) of the title compound.

$^1$H NMR (400 MHz, CDCl$_3$, ppm): δ1.26 (t, J=7.6 Hz, 3H), 2.49 (s, 3H), 2.65 (s, 3H), 2.81 (q, J=7.6 Hz, 2H), 3.72 (s, 3H), 4.22 (s, 2H), 6.06 (s, 1H), 6.81 (d, J=8.4 Hz, 2H), 7.09 (d, J=8.4 Hz, 2H), 7.24-7.28 (m, 3H), 7.37-7.39 (m, 1H), 7.58-7.61 (m, 1H). FAB-MS: m/e 464 (M+1).

Step B: Preparation of 2-[4-[(2-ethyl-6,8-dimethylimidazo[1,2-b]pyridazin-3-yl)methyl]phenoxy]-2-(2-chlorophenyl)acetic acid To a solution of 0.041 g (0.09 mmol) of the product of Step A in 2 mL of methanol was added 0.5 mL of a 1.0N solution of sodium hydroxide and the reaction mixture was stirred at room temperature for 1 hour. The reaction mixture was then adjusted to pH=6 with 0.5 mL of 1.0N hydrochloric acid, then concentrated in vacuo. The residue was purified on a silica gel flash chromatography column eluted with CHCl$_3$-MeOH-NH$_4$OH (80:15:1). The purified fractions were combined, evaporated and dried in vacuo to afford 0.030 g (75%) of the title compound.

$^1$H NMR (400 MHz, CD$_3$OD, ppm): δ1.22 (t, J=7.6 Hz, 3H), 2.52 (s, 3H), 2.57 (s, 3H), 2.80 (q, J=7.6 Hz, 2H), 4.28 (s, 2H), 5.97 (s, 1H), 6.84 (d, J=8.4 Hz, 2H), 7.04 (s, 1H), 7.11 (d, J=8.4 Hz, 2H), 7.27-7.30 (m, 2H), 7.40-7.42 (m, 1H), 7.58-7.60 (m, 1H). FAB-MS: m/e 450 (M+1).

EXAMPLE 33

2-[4-[(2-ethyl-6,8-dimethylimidazo[1,2-b]pyridazin-3-yl)methyl]phenoxy]-2-(3-chlorophenyl)acetic acid Step A: Preparation of methyl 2-[4-[(2-ethyl-6,8-dimethylimidazo[1,2-b]pyridazin-3-yl)methyl]phenoxy]-2-(3-chlorophenyl)acetate A 10 mL round bottom flask equipped with a magnetic stir bar and a reflux condenser was charged with 0.050 g (0.18 mmol) of the product of Step E in Example 1, 0.049 g (0.35 mmol) of potassium carbonate, 0.056 g (0.21 mmol) of methyl 2-bromo-2-(3-chlorophenyl)acetate and 1 mL of dimethylformamide. The reaction mixture was stirred and heated at 90° C. for 15 hours at which point TLC analysis (50% EtOAc-hexane) indicated remaining phenol. A second portion of methyl 2-bromo-2-(3-chlorophenyl)acetate (0.050 g; 0.19 mmol) and 0.050 g (0.36 mmol) of potassium carbonate were added and the reaction was heated at 90° C. for an additional 24 hours. The reaction mixture was then cooled to room temperature, the excess potassium carbonate was removed by filtration and the filtrate was concentrated in vacuo. The residue was purified on a silica gel flash chromatography column eluted with 50% EtOAc-hexane. Combination of the purified fractions followed by evaporation and drying in vacuo afforded 0.043 g (52%) of the title compound.

$^1$H NMR (400 MHz, CDCl$_3$, ppm): δ1.25 (t, J=7.6 Hz, 3H), 2.47 (s, 3H), 2.60 (s, 3H), 2.79 (q, J=7.6 Hz, 2H), 3.70 (s, 3H), 4.23 (s, 2H), 5.52 (s, 1H), 6.68 (s, 1H), 6.79 (d, J=8.8 Hz, 2H), 7.12 (d, J=8.8 Hz, 2H), 7.28-7.30 (m, 2H), 7.39-7.42 (m, 1H), 7.54 (s, 1H). FAB-MS: m/e 464 (M+1).

Step B: Preparation of 2-[4-[(2-ethyl-6,8-dimethylimidazo[1,2-b]pyridazin-3-yl)methyl]phenoxy]-2-(3-chlorophenyl)acetic acid To a solution of 0.043 g (0.09 mmol) of the product of Step A in 1 mL of methanol was added 0.5 mL of a 1.0N solution of sodium hydroxide and the reaction mixture was stirred at room temperature for 15 hours. The reaction mixture was then adjusted to pH=6 with 0.5 mL of 1.0N hydrochloric acid, then concentrated in vacuo. The residue was purified on a silica gel flash chromatography column eluted with CHCl$_3$-MeOH-NH$_4$OH (80:15:1). The purified fractions were combined, evaporated and dried in vacuo to afford 0.028 g (67%) of the title compound.

$^1$H NMR (400 MHz, CD$_3$OD, ppm): δ1.22 (t, J=7.6 Hz, 3H), 2.52 (s, 3H), 2.57 (s, 3H), 2.80 (q, J=7.6 Hz, 2H), 4.28 (s, 2H), 5.52 (s, 1H), 6.86 (d, J=8.8 Hz, 2H), 7.03 (s, 1H), 7.12 (d, J=8.8 Hz, 2H), 7.30-7.34 (m, 2H), 7.49 (d, J=6.8 Hz, 1H), 7.59 (s, 1H). FAB-MS: m/e 450 (M+1).

Table 1 below lists additional compounds which were prepared using the procedures of the foregoing examples.

TABLE 1

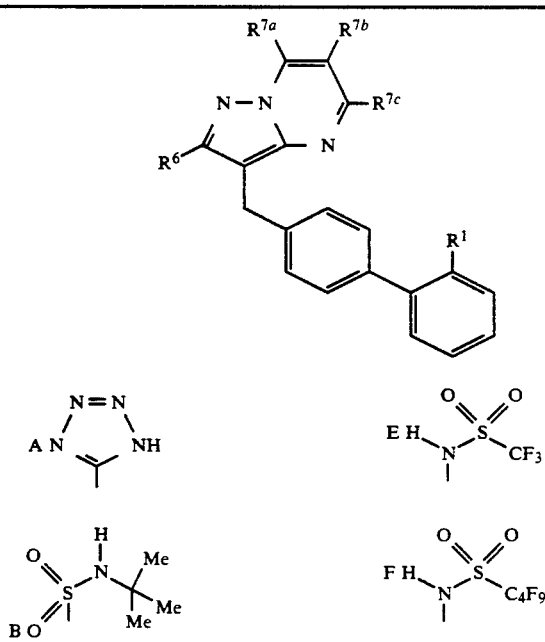

TABLE 1-continued

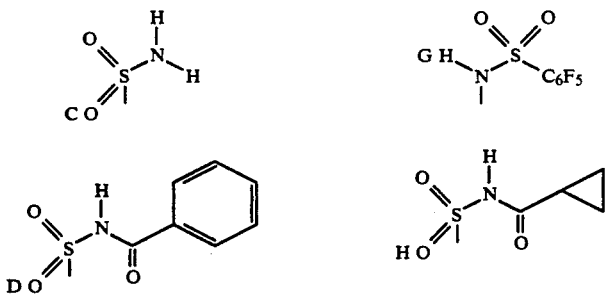

| # | R[1] | R[6] | R[7a] | R[7b] | R[7c] | Characteristic |
|---|------|------|-------|-------|-------|----------------|
| 1 (Ex 7) | A | cyPr | Me | H | Me | MS m/e 422 (M + 1) |
| 2 | A | Et | Me | H | Me | MS m/e 410 (M + 1) |
| 3 | A | cyPr | Et | H | Et | MS m/e 450 (M + 1) |
| 4 | A | cyPr | COOEt | H | Me | MS m/e 480 (M + 1) |
| 5 | A | cyPr | COOH | H | Me | MS m/e 452 (M + 1) |
| 6 | A | cyPr | Me | Me | Me | MS m/e 436 (M + 1) |
| 7 | A | cyPr | Me | nPr | Me | MS m/e 464 (M + 1) |
| 8 | A | cyPr | Me | iPr | Me | MS m/e 464 (M + 1) |
| 9 | A | cyPr | Me | nBu | Me | MS m/e 478 (M + 1) |
| 10 | A | cyPr | Me | nPen | Me | MS m/e 492 (M + 1) |
| 11 | A | cyPr | Me | Ph | Me | MS m/e 498 (M + 1) |
| 12 | A | cyPr | Me | $(CH_2)_2CO_2Et$ | Me | MS m/e 522 (M + 1) |
| 13 | A | cyPr | Me | $(CH_2)_2CO_2H$ | Me | MS m/e 494 (M + 1) |
| 14 | B | nPr | Me | H | Me | Rf 0.40 |
| 15 | C | nPr | Me | H | Me | Rf 0.21 |
| 16 | D | nPr | Me | H | Me | MS m/e 539 (M + 1) |
| 17 | B | cyPr | Me | H | Me | Rf 0.46 |
| 18 (Ex 15) | C | cyPr | Me | H | Me | Rf 0.36 |
| 19 (Ex 16) | D | cyPr | Me | H | Me | MS m/e 537 (M + 1) |
| 20 | C | Et | Me | H | Me | Rf 0.19 |
| 21 (Ex 8) | A | cyPr | Me | H | $CF_3$ | MS m/e 476 (M + 1) |
| 22 (Ex 9) | A | cyPr | $CF_3$ | H | $CF_3$ | MS m/e 530 (M + 1) |
| 23 | G | cyPr | Me | H | Me | MS m/e 599 (M + 1) |
| 24 | D | cyPr | Me | H | Me | MS m/e 537 (M + 1) |
| 25 | F | cyPr | Me | H | Me | MS m/e 651 (M + 1) |
| 26 | A | cyPr | Me | H | SMe | MS m/e 454 (M + 1) |
| 27 | A | cyPr | Me | H | COOMe | MS m/e 466 (M + 1) |
| 28 | A | cyPr | Me | H | S(O)Me | MS m/e 470 (M + 1) |
| 29 | A | cyPr | Me | H | $S(O)_2Me$ | MS m/e 486 (M + 1) |
| 30 | E | cyPr | Me | H | Me | MS m/e 501 (M + 1) |
| 31 | A | cyPr | Me | H | COOH | MS m/e 452 (M + 1) |
| 32 | E | cyPr | Me | H | COOH | MS m/e 531 (M + 1) |
| 33 | E | cyPr | Me | H | COOMe | MS m/e 545 (M + 1) |
| 34 | H | cyPr | Me | H | COOMe | MS m/e 545 (M + 1) |
| 35 | H | cyPr | Me | H | COOH | MS m/e 531 (M + 1) |
| 36 | A | cyPr | Me | H | CN | MS m/e 433 (M + 1) |
| 37 | $NO_2$ | cyPr | Me | H | SMe | MS m/e 431 (M + 1) |
| 38 | $NO_2$ | cyPr | Me | H | COOMe | MS m/e 443 (M + 1) |
| 39 | $NH_2$ | cyPr | Me | H | COOMe | MS m/e 413 (M + 1) |

Fast atom bombardment mass spectrometry and the Rf was measured in 50% EtOAc/Hex.

EXAMPLE 34

Typical Pharmaceutical Compositions Containing a Compound of the Invention

A: Dry Filled Capsules Containing 50 mg of Active Ingredient Per Capsule

| Ingredient | Amount per capsule (mg) |
|---|---|
| 5-carboethoxy-2-cyclopropyl-7-methyl-3-[(2'-(tetrazol 5-yl)-biphen-4-yl)methyl]pyrazolo[1,5-a]pyrimidine | 50 |
| Lactose | 149 |
| Magnesium stearate | 1 |
| Capsule (size No. 1) | 200 |

The 5-carboethoxy-2-cyclopropyl-7-methyl-3-[(2'(tetrazol-5-yl)biphen-4-yl)methyl]pyrazolo[1,5-a]pyrimidine can be reduced to a No. 60 powder and the lactose and magnesium stearate can then be passed through a No. 60 blotting cloth onto the powder. The combined ingredients can then be mixed for about 10 minutes and filled into a No. 1 dry gelatin capsule.

B: Tablet

A typical tablet would contain 5-carboethoxy-2-cyclopropyl-7-methyl-3 [(2'-(tetrazol-5-yl)biphen-4-yl)methyl]pyrazolo[1,5-a]pyrimidine (25 mg), pregelatinized starch USP (82 mg), microcrystalline cellulose (82 mg) and magnesium stearate (1 mg).

C: Combination Tablet

A typical combination tablet would contain, for example, 5-carboethoxy-2-cyclopropyl-7-methyl-3-[(2'-(tetrazol-5-yl)biphen-4-yl)methyl]pyrazolo[1,5-a]pyrimidine, a diuretic such as hydrochlorothiazide and consist of (50 mg) pregelatinized starch USP (82 mg), micro-crystalline cellulose (82 mg) and magnesium stearate (1 mg).

D: Suppository

Typical suppository formulations for rectal administration can contain 5-carboethoxy-2-cyclopropyl-7-methyl-3-[(2'-(tetrazol-5-yl)biphen-4-yl)methyl]-pyrazolo[1,5-a]pyrimidine, (0.08–1.0 mg), disodium calcium edetate (0.25–0.5 mg), and polyethylene glycol (775–1600 mg). Other suppository formulations can be made by substituting, for example, butylated hydroxytoluene (0.04–0.08 mg) for the disodium calcium edetate and a hydrogenated vegetable oil (675–1400 mg) such as Suppocire L, Wecobee FS, Wecobee M, Witepsols, and the like, for the polyethylene glycol. Further, these suppository formulations can also include another active ingredient such as another antihypertensive and/or a diuretic and/or an antiotensin converting enzyme and/or a calcium channel blocker in pharmaceutically effective amount as described, for example, in C above.

E: Injection

A typical injectible formulation would contain, 5-carboethoxy-2-cyclopropyl-7-methyl-3-[(2'-(tetrazol-5yl)-biphen-4yl)methyl]pyrazolo[1,5-a]pyrimidine, sodium phosphate dibasic anhydrous (11.4 mg) benzyl alcohol (0.01 ml) and water for injection (1.0 ml). Such an injectible formulation can also include a pharmaceutically effective amount of another active ingredient such as another antihypertensive and/or a diuretic and/or an angiotensin converting enzyme inhibitor and/or a calcium channel blocker.

What is claimed is:

1. A compound having the formula:

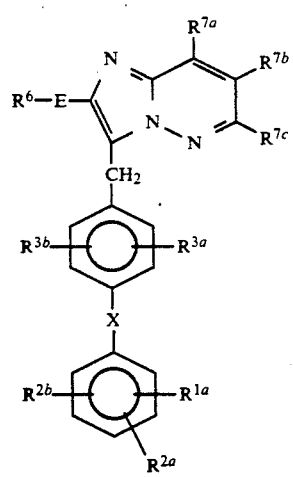

or a pharmaceutically acceptable salt thereof, wherein:
$R^{1a}$ is (a) —H, (b) —$CO_2 R^4$, (c) —$SO_3 R^5$, (d) —NHSO_2 CF_3, (e) —PO(OR^5)_2, (f) —SO_2—NH—R^8, (g) —CONHOR^5, (h)

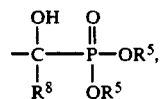

(i) —CN, (j) —PO(OR^5)R^4, (k), (l), (m),

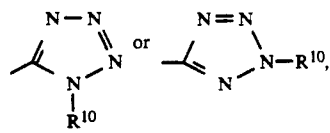

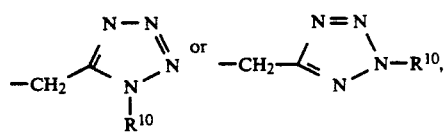

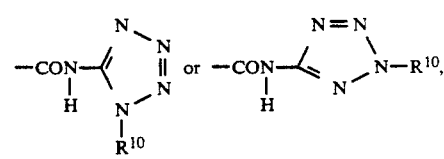

(n) —CONHNHSO_2 CF_3, (o), (p), (q), (r), (s)

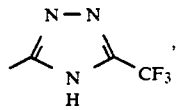

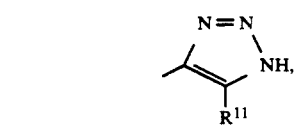

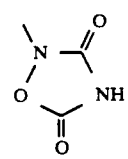

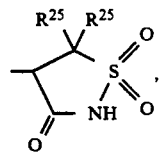
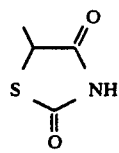
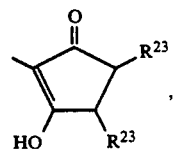
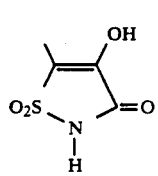
(t) —CONHSO₂ R²⁰, (u) —SO₂ NHCOR²⁰, (v) —CH₂ SO₂ NHCO—R²⁰, (w) —CH₂ CONH—SO₂ R²⁰, (x) —NHSO₂ NHCO—R²⁰, (y) —NHCONHSO₂ —R²⁰, (z) —CONHSO₂ NR⁴ R²⁰, (aa) —SO₂ N(R²² )OR²², (ab) —SO₂ NHSO₂ R²¹, (ac) —SO₂ NHPO(R²⁴ )₂, (ad) —CONHPO(R²⁴ )₂, (ae) —SO₂ NHCN, (af) —SO₂ NHSO₂ NR²⁶ R²⁷, (ag)
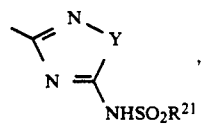
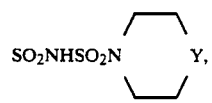
wherein Y is O or S, (ah) —NHSO₂ NHSO₂ R²¹, (ai) —NHSO₂ NHPO(R²⁴ )₂, (aj) —NHSO₂ R²¹, (ak) —NR²⁶ COCO₂ H, (al) —SO₂ NHCO₂ R²⁰, (am), (an), (ao), (a0), (aq), (ar),
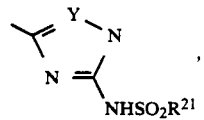
wherein n is 0 to 2, (as), (at), (au), or (av)
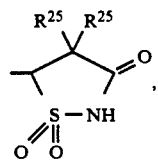
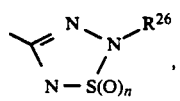

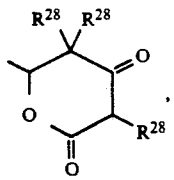

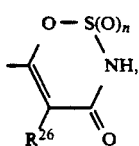

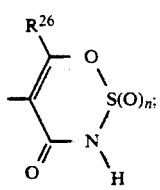

$R^{2a}$ and $R^{2b}$ are each independently (a) H, (b) Br, Cl, F, I, (c) $NO_2$, (d) $NH_2$, (e) $NH[(C_1 - C_4)$-alkyl], (f) $N[(C_1 - C_4)$-alkyl]$_2$ (g) $SO_2 NHR^8$, (h) $CF_3$, (i) $(C_1 - C_6)$-alkyl, $(C_2 - C_6)$-alkenyl, or $(C_2 - C_6)$-alkynyl, or (j) $(C_1 - C_4)$-alkoxy;

$R^{3a}$ is (a) H, (b) Cl, Br, I, or F, (c) $(C_1 - C_6)$-alkyl, (d) $(C_1 - C_6)$-alkoxy, (e) $(C_1 - C_6)$-alkoxy-$(C_1 - C_4)$-alkyl;

$R^{3b}$ is (a) H, (b) Cl, Br, I, or F, (c) $NO_2$, (d) $(C_1 - C_6)$-alkyl, $(C_2 - C_6)$-alkenyl, or $(C_2 - C_6)$-alkynyl, (e) $(C_1 - C_6)$-alkanoyloxy, (f) $(C_3 - C_6)$-cycloalkyl, (g) $(C_1 - C_6)$-alkoxy, (h) —$NHSO_2 R^4$, (i) hydroxy-$(C_1 - C_4)$-alkyl, (j) furyl, (k) $(C_1 - C_4)$-alkylthio, (l) $(C_1 - C_4)$-alkylsulfinyl, (m) $(C_1 - C_4)$-alkylsulfonyl, (n) $NH_2$, (o) $NH[(C_1 - C_4)$-alkyl], (p) $N[(C_1 - C_4)$-alkyl]$_2$, (q) $(C_1 - C_4)$-perfluoroalkyl, (r) —$SO_2$ —$NHR^8$, (s) aryl, wherein aryl is phenyl, unsubstituted or substituted with one or two substituents selected from the group consisting of Cl, Br, I, F or $(C_1 - C_4)$-alkyl, which is substituted or unsubstituted with members selected from the group consisting of: $N(R^4)_2$, $CO_2 R^4$, OH, $N(R^4)CO_2 R^{20}$, $S(O)_n R^{20}$, wherein n is 0 to 2 ; $(C_1 - C_4)$-alkoxy, $NO_2$, $CF_3$, $(C_1 - C_4)$-alkylthio, OH, $NH_2$, —$NH[(C_1 - C_4)$-alkyl], —$N[(C_1 - C_4)$-alkyl]$_2$, —$CO_2 H$, —$CO_2$ —$(C_1 - C_4)$-alkyl, $N(R^4)CO_2 R^{20}$, or

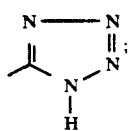

or (t) aryl-$(C_1 - C_4)$-alkyl;

$R^4$ is H, $(C_1 - C_6)$-alkyl unsubstituted or substituted with aryl;

$R^{4a}$ is $(C_1 - C_6)$-alkyl, aryl or aryl—$CH_2$—;

$R^5$ is H, or —$CHR^4 OCOR^{4a}$;

E is a single bond, —$NR^{12} (CH_2)_s$—, —$S(O)_n(CH_2)_s$—wherein s is 0 to 5, —$CH(OH)$—, —O—, —CO—;

$R^6$ is (a) aryl, (b) $(C_1 - C_6)$-alkyl, $(C_2 - C_5)$-alkenyl or $(C_2 - C_5)$-alkynyl each of which is unsubstituted or substituted with a substituent selected from the group consisting of: aryl, $C_3 - C_7$-cycloalkyl, Cl, Br, I, F, —OH, $CF_3$, —$CF_2 CF_3$, $CCl_3$, —$NH_2$, —$NH[(C_1 - C_4)$-alkyl], —$N[(C_1 - C_4)$-alkyl]$_2$, —$NH$—$SO_2 R^4$, —$COOR^4$, —$SO_2 NHR^8$, $(C_1 - C_4)$-alkoxy, $(C_1 - C_4)$-alkyl-S; (c) $(C_3 - C_7)$-cycloalkyl;

$R^{7a}$, $R^{7b}$ and $R^{7c}$ are independently (a) H, (b) aryl-$(C_1 - C_4)$-alkyl-, (c) heteroaryl-$(C_1 - C_4)$-alkyl-, (d) $(C_1 - C_4)$-alkyl, unsubstituted or substituted with a substituent selected from the group consisting of: —OH, —$NH_2$, guanidino, $(C_1 - C_4)$-alkoxy, —$S(O)_n R^{20}$, $(C_1 - C_4)$-alkylamino, $(C_1 - C_4)$-dialkylamino, —$COOR^4$, —$CON(R^4)R^{20}$, —$OCON(R^4)R^{20}$, —O—$COR^4$, $(C_3 - C_5)$-cycloalkyl, —$N(R^4)CON(R^4)R^{20}$, —$N(R^4)COOR^{20}$, —$CONHSO_2 R^{20}$, —$N(R^4)SO_2 R^{20}$; (e) $(C_2 - C_4)$-alkenyl, (f) —CO-aryl, (g) $(C_3 - C_7)$-cycloalkyl, (h) Cl, Br, I, or, F (i) —OH, (j) —$OR^{20}$, (k) $(C_1 - C_4)$-perfluoroalkyl, (l) —SH, (m) —$S(O)_n R^{20}$, (n) —CHO, (o) —$CO_2 R^4$, (p) —$SO_3 H$, (q) —$N(R^4)_2$, (r) —$N(R^4)CO_2 R^{20}$, (s) —$N(R^4)CONR^4 R^{20}$, (t) —$N(R^4)CSNR^4 R^{20}$, (u)

wherein G is —$CH_2$—, —O——$N(R^4)$—, or —N(-$COR^{20}$)—, (v) —$SO_2 NR^8 R^9$, (w) —$CH_2 OCOR^4$, (x) —$N(R^4)$—$SO_2$—$(C_1 - C_4)$-alkyl, (y) 5 or 6 membered saturated heterocycle containing one nitrogen atom and containing one other heteroatom selected from N, O or S, selected from pyrrolidine, morpholine, and piperazine, (z) aryl.

2. (aa)

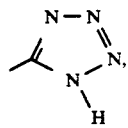

(ab) —$NHSO_2$—$(C_1 - C_4)$-perfluoroalkyl, (ac) —$CONHSO_2 R^{20}$, (ad) —$SO_2 NHCOR^{20}$, (ae) —$S(O)_n$-aryl, (af) —$S(O)_n CH_2$-aryl, (ag) —$CON(R^4)_2$, (ah) —$N[CH_2 CH_2]_2 G$, or (ai) —$CON[CH_2 CH_2]_2 G$;

$R^8$ is H, $(C_1 - C_5)$-alkyl, phenyl or benzyl;

$R^9$ is H, $(C_1 - C_4)$-alkyl;

$R^{10}$ is H, $(C_1 - C_6)$-alkyl, $(C_2 - C_4)$-alkenyl, $C_1 - C_4$-alkoxy alkyl, or —$CH_2$—$C_6 H_4 R^{19}$;

$R^{11}$ is —CN, —NO$_2$ or —CO$_2$R$^4$; perfluoroalkyl (C$_1$ - C$_4$)

$R^{12}$ is H, (C$_1$ - C$_4$)-acyl, (C$_1$ - C$_6$)-alkyl, allyl, (C$_3$ - C$_6$)-cycloalkyl, phenyl or benzyl;

$R^{13}$ is H, (C$_1$ - C$_8$)-alkyl, (C$_1$ - C$_8$)-perfluoroalkyl, (C$_3$ - C$_6$)-cycloalkyl, phenyl or benzyl;

$R^{14}$ is H or (C$_1$ - C$_6$)-alkyl;

$R^{15}$ is H, (C$_1$ - C$_6$)-alkyl, (C$_3$ - C$_6$)-cycloalkyl, phenyl or benzyl;

$R^{16}$ is —NR$^8$R$^9$, —OR$^9$, —NHCONH$_2$, —NHCSNH$_2$,

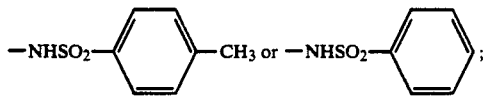

$R^{17}$ and $R^{18}$ are independently (C$_1$ - C$_4$)-alkyl or taken together are —(CH$_2$)$_q$—, wherein q is 2 or 3;

$R^{19}$ is H, —NO$_2$, —NH$_2$, —OH or —OCH$_3$;

$R^{20}$ is (a) aryl, (b) (C$_1$ - C$_8$)-alkyl, wherein the alkyl group is unsubstituted or substituted with a substituent selected from the group consisting of: aryl, —OH, —SH, (C$_3$ - C$_5$)-cycloalkyl, —O(C$_1$ - C$_4$)-alkyl, —S—(C$_1$ - C$_4$)-alkyl, —CF$_3$, Cl, Br, F, I, —NO$_2$, —CO$_2$H, —CO$_2$R$^4$, NHCOR$^{4a}$, —NH$_2$, —NH[(C$_1$ - C$_4$)-alkyl], —N[(C$_1$ - C$_4$)-alkyl]$_2$, PO$_3$H$_2$, PO(OH)(aryl), PO(OH)[(C$_1$ - C$_4$)-alkyl]; (c) C$_3$ - C$_5$-cycloalkyl, unsubstituted or substituted with one or two substitutents selected from the group consisting of: (C$_1$ - C$_6$)-alkyl, —OH, —NH$_2$, —NH[(C$_1$ - C$_4$)-alkyl], —N[(C$_1$ - C$_4$)-alkyl]$_2$, NHCOR$^{4a}$, —CO$_2$H, —CO$_2$R$^4$, Cl, Br, F, I, —CF$_3$, or (d) C$_1$ - C$_4$ perfluoroalkyl;

X is (a) a carbon-carbon single bond, (b) —O—, (c), (d)

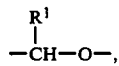

$R^2$ is: (a) —CO$_2$H, (b) —CO$_2$R$^{29}$, (c) —CONH—SO$_2$—R$^{20}$, (d) —CONHSO$_2$NR$^8$R$^8$, (e) —CONHOR$^5$, (f) CONHNHSO$_2$CF$_3$, (g) CH$_2$SO$_2$NHCOR$^{20}$, (h) CH$_2$CONHSO$_2$R$^{20}$, (i)

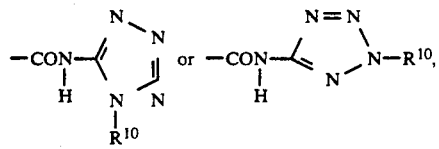

$R^{21}$ is (a) aryl, (b) (C$_3$ - C$_7$)-cycloalkyl, (c) (C$_1$ - C$_6$)-alkyl or a substituted (C$_1$ - C$_6$)-alkyl with one or two substituents selected from the group consisting of aryl, —OH, —SH, (C$_1$ - 7 C$_4$)-alklyl, (C$_3$ - C$_7$)-cycloalkyl, —O(C$_1$ - C$_4$)-alkyl, —S(C$_1$ - C$_4$)-alkyl, —CF$_3$, Cl, Br, F, I, —NO$_2$, —CO$_2$H, —CO$_2$—(C$_1$ - C$_4$)-alkyl, —N[(C$_1$ - C$_4$)-alkyl]$_2$, —PO$_3$H$_2$, —PO(OH) (O—(C$_1$ - C$_4$)-alkyl), PO(OR$^{26}$)(R$^{27}$), morpholinyl or (C$_1$ - C$_4$)-alkylpiperazinyl), or (d) —(C$_1$ - C$_4$)-perfluoroalkyl;

$R^{22}$ is (a) hydrogen, (b) aryl, (c) (C$_3$ - C$_7$)-cycloalkyl, (d) (C$_1$ - C$_6$)-alkyl or a substituted (C$_1$ - C$_6$)-alkyl with a substituent selected from the group consisting of aryl, —OH, —SH, (C$_1$ - C$_4$)-alkyl, —O(C$_1$ - C$_4$)-alkyl, —S(C$_1$ - C$_4$)-alkyl, —CF$_3$, Cl, Br, F, I, —NO$_2$, —CO$_2$H, —CO$_2$—(C$_1$ - C$_4$)-alkyl, —NH$_2$, —NH[(C$_1$ - C$_4$)-alkyl], —N[(C$_1$ - C$_4$)-alkyl]$_2$, —PO$_3$H$_2$, —PO(OH)-(O—(C$_1$ - C$_4$)-alkyl), —PO(OR$^{26}$)(R$^{27}$), morpholinyl or (C$_1$ - C$_4$)-alkylpiperazinyl, or (e) —(C$_1$ - C$_4$)-perfluoroalkyl;

$R^{23}$ is (a) H, (b) aryl as defined above, or (c) (C$_1$ - C$_6$)-alkyl optionally substituted with aryl, F, Cl, Br, —OH, —NH$_2$, —NH(C$_1$ - C$_4$)-alkyl, —N[(C$_1$ - C$_4$)-alkyl]$_2$, or CF$_3$;

$R^{24}$ is (a) aryl as defined above, (b) (C$_1$ - C$_6$)-alkyl optionally substituted with aryl, F, Cl, Br, —OH, —NH$_2$, —NH(C$_1$ - C$_4$)-alkyl, —N[(C$_1$ - C$_4$)-alkyl]$_2$, CF$_3$, —COOR$^{26}$, or CN, (c) —OCH(R$^{26}$)—O—R$^{26a}$, or (d) —OH, —O—(C$_1$ - C$_6$)-alkyl;

$R^{25}$ is (a) H, (b) (C$_1$ - C$_6$)-alkyl optionally substituted with aryl, F, Cl, Br, —OH, —NH$_2$, —NH[(C$_1$ - C$_4$)-alkyl], —N[(C$_1$ - C$_4$)-alkyl]$_2$, CF$_3$, —COOR$^{26}$, or CN, or (c) F, Cl, Br;

$R^{26}$ is H, aryl, (C$_1$ - C$_6$)-alkyl, or substituted (C$_1$ - C$_6$)-alkyl wherein the substituent is aryl;

$R^{26a}$ is aryl, (C$_1$ - C$_6$)-alkyl or aryl-(C$_1$ - C$_6$)-alkyl;

$R^{27}$ is H, (C$_1$ - C$_5$)-alkyl, aryl or arylmethyl;

$R^{28}$ is H, (C$_1$ - C$_6$)-alkyl, (C$_2$ - C$_4$)-alkenyl, or (C$_2$ - C$_4$)-alkoxyalkyl;

$R^{29}$ is: (a) (C$_1$ - C$_4$)-alkyl, (b) CHR$^{30}$—O—COR$^{31}$, (c) CH$_2$CH$_2$—N[(C$_1$ - C$_2$)-alkyl]$_2$, (d) CH$_2$CH$_2$—N[CH$_2$CH$_2$]$_2$O, (e) aryl or CH$_2$-aryl, where aryl is as defined above or optionally substituted with CO$_2$—(C$_1$ - C$_4$)-alkyl, (g), (h), (i) or (j)

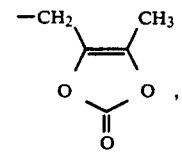

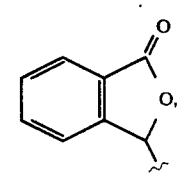

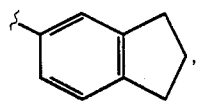

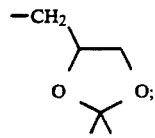

and R$^{30}$ and R$^{31}$ independently are (C$_1$ - C$_6$)-alkyl or phenyl.

2. A compound of claim 1 of formula (I)

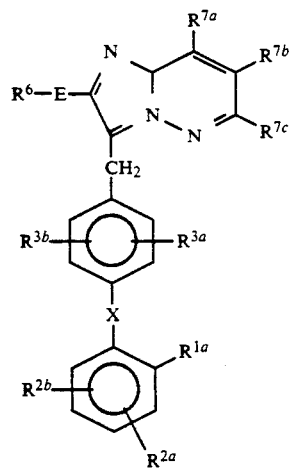

or a pharmaceutically acceptable salt thereof, wherein:
R$^{1a}$ is (a) —COOH, (b)

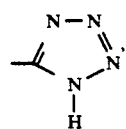

(c)

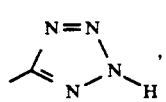

(d) —NH—SO$_2$ CF$_3$, (e) —CO$_2$ R$^4$, (f) —CONHSO$_2$ R$^{20}$, (g) —SO$_2$ NHCOR$^{20}$, (h) —CH$_2$ SO$_2$ NHCO—R$^{20}$, (i) —CH$_2$ CONHSO$_2$ —R$^{20}$, (j) —NH-SO$_2$ NHCO—R$^{20}$, (k) —NHCONHSO$_2$ —R$^{20}$, (l) —CONHSO$_2$ NR$^4$ R$^{20}$, (m) —SO$_2$ NHCONR$^4$ R$^{20}$, or (n) —SO$_2$ NHCO$_2$ R$^{20}$;

R$^{2a}$ and R$^{2b}$ are H, F, Cl, CF$_3$, (C$_1$ - C$_6$)-alkyl, (C$_2$ - C$_6$)-alkenyl or (C$_2$ - C$_6$)-alkynyl;

R$^{3a}$ is H, F or Cl;

R$^{3b}$ is H, F, Cl, CF$_3$, (C$_1$ - C$_6$)-alkyl, (C$_2$ - C$_6$)-alkyl, (C$_2$ - C$_6$)-alkynyl, (C$_5$ - C$_6$)-cycloalkyl, —COOCH$_3$, —COOC$_2$ H$_5$, —SO$_2$—CH$_3$, —N(R$^4$)$_2$ or —NH—SO$_2$ CH$_3$;

E is a single bond, —O—or —S—;

R$^6$ is
(a) C$_1$ - C$_5$-alkyl, unsubstituted or substituted with a substituent selected from the group consisting of Cl, CF$_3$, CCl$_3$, —O—CH$_3$, —OC$_2$ H$_5$, —S—CH$_3$, —S—C$_2$ H$_5$ or phenyl, (b) (C$_2$ - C$_5$)-alkenyl or (C$_2$ - C$_5$)-alkynyl, or (c) (C$_3$ - C$_5$)-cycloalkyl;

R$^{7a}$, R$^{7b}$ and R$^{7c}$ are independently
(a) H,
(b) (C$_1$ - C$_4$)-alkyl,
(c) (C$_2$ - C$_4$)-alkenyl,
(d) —OH,
(e) —CH$_2$ OCOR$^4$,
(f)

$$-NH-\overset{O}{\underset{\|}{C}}-O-(C_1-C_4)\text{-alkyl},$$

(g)

$$NH-\overset{O}{\underset{\|}{C}}-NHR^{20},$$

(h) —(C$_1$ - C$_4$)-alkoxy,
(i) —NH[(C$_1$ - C$_4$)-alkyl],
(j) —N[(C$_1$ - C$_4$)-alkyl]$_2$,
(k) Cl, F or Br,
(l) —CF$_3$,
(m) —CO$_2$ R$^4$,
(n) —CH$_2$ OH,
(o) 5 or 6 membered saturated heterocycle, containing one nitrogen atom and containing one other heteroatom selected from N, O or S, selected from pyrrolidine, morpholine, and piperazine.
(p) —CO-aryl,
(q) —S(O)$_n$—(C$_1$ - C$_4$)-alkyl,
(r) —SO$_2$ —NH—(C$_1$ - C$_4$)-alkyl,
(s) —SO$_2$ —NH-aryl,
(t) —NH—SO$_2$ CH$_3$,
(u) aryl,
(v)

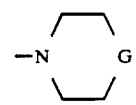

(w)

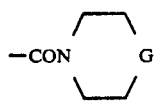

(x) —CON(R⁴)₂, or (y)

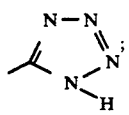

and,

X is a C—C single bond or —CO—.

3. A compound of claim 2 wherein:

R¹ᵃ is (a) —COOH, (b)

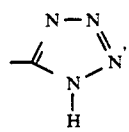

(c) —NH—SO₂—CF₃, (d) —CONHSO₂ R²⁰, (e) —SO₂ NHCOR²⁰, (f) —CH₂ SO₂ NHCO—R²⁰, (g) —CH₂ CONH—SOR²⁰, (h) —NHSO₂ NHCO—R²⁰, (i) —NHCONHSO₂—R²⁰, (j) —CONHSO₂ NR⁴ R²⁰, (k) —SO₂ NHCONR⁴ R²⁰, or (l) —SO₂ NHCO₂ R²⁰;

R²ᵃ, R²ᵇ, R³ᵃ and R³ᵇ are each H;

R⁶ is n-propyl, n-butyl, methyl, ethyl, cyclopropyl, —CH₂—S—CH₃;

R⁷ᵃ is H, —(C₁ - C₄)-alkyl, or aryl;

R⁷ᵇ is —H, —F, —Cl, —(C₁ - C₄)-alkyl;

R⁷ᶜ is —(C₁ - C₄)-alkyl, aryl, CON(R⁴)₂, CO₂ R⁴, 1H-tetrazol-5-yl, N[CH₂ CH₂]₂ NH, N[CH₂ CH₂]₂ NCOR²⁰, NHSO₂ CH₃, or E is a single bond or —S—; and, X is a single bond.

4. The compound of claim 1 of structural formula I

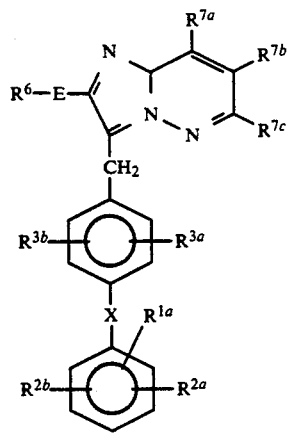

wherein:

R²ᵃ and R²ᵇ are independently:
- (a) Br, Cl, I, F,
- (b) (C₁ - C₄)-alkyl,
- (c) (C₂ - C₄)-alkenyl,
- (d) (C₂ - C₄)-alkynyl,
- (e) (C₁ - C₄)-alkoxyl,
- (f) CF₃,
- (g) SO₂ NHR⁸,
- (h) NO₂,
- (i) NH₂;

R³ᵃ and R³ᵇ are independently
- (a) (C₁ - C₆)-alkyl,
- (b) (C₂ - C₆)-alkenyl,
- (c) (C₂ - C₆)-alkynyl,
- (d) (C₁ - C₄)-alkoxyl, or
- (e) Cl, Br, I, F;

R⁶ is
- (a) cyclopropyl, or
- (b) (C₁ - C₄)-alkyl;

R⁷ᵃ is
- (a) (C₁ - C₄)-alkyl,
- (b) CO₂ R⁴,

R⁷ᵇ is
- (a) H,
- (b) —(C₁ - C₆)-alkyl,
- (c) phenyl,
- (d) —(C₁ - C₄)-alkyl-CO₂ R⁴, or
- (e) —(C₁ - C₄)-alkyl-CO₂ H;

R⁷ᶜ is
- (a) (C₁ - C₄)-alkyl;

X is:
- (a) —OCHR¹—,
- (b) —CHR¹—O—,

R¹ is
- (a) CO₂ R²⁹
- (b) 1H-tetrazol-5-yl,
- (c) CO₂ (C₁ - C₄)-alkyl, or
- (d) CONHSO₂ R²⁰

R¹⁵ is:
- (a) H,
- (b) (C₁ - C₄)-alkyl, or
- (c) phenyl.

5. The compound of claim 4 of structural formula I

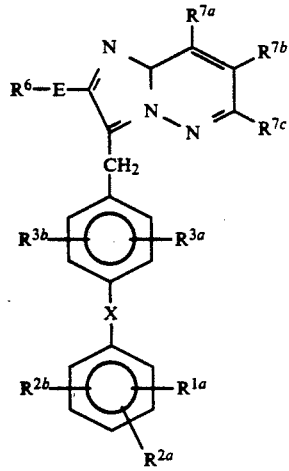

wherein:
X is —OCHR¹—.

6. A compound which is a member of the group:
(1) 2-Butyl-3-[(2'-carboxybiphen-4-yl)methyl]imidazo[1,2-b]pyridazine;
(2) 3-[(2'-Carboxybiphen-4-yl)methyl]-2-propylimidazo[1,2-b]pyridazine;
(3) 3-[(2'-Carboxybiphen-4-yl)methyl]-2-ethylimidazo[1,2-b]pyridazine;
(4) 3-[(2'-Carboxybiphen-4-yl)methyl]-2-isopropylimidazo[1,2-b]pyridazine;
(5) 3-[(2'-Carboxybiphen-4-yl)methyl]-2-cyclopropylimidazo[1,2-b]pyridazine;
(6) 3-[(2'-Carboxybiphen-4-yl)methyl]-7-methyl-2-propylimidazo[1,2-b]pyridazine;
(7) 3-[(2'-Carboxybiphen-4-yl)methyl]-7-ethyl-2-propylimidazo[1,2-b]pyridazine;
(8) 3-[(2'-Carboxybiphen-4-yl)methyl]-2-ethyl-7-methylimidazo[1,2-b]pyridazine;
(9) 3-[(2'-Carboxybiphen-4-yl)methyl]-2,7-diethylimidazo[1,2-b]pyridazine;
(10) 3-[(2'-Carboxybiphen-4-yl)methyl]-5,7-dimethyl-2-propylimidazo[1,2-b]pyridazine;
(11) 3-[(2'-Carboxybiphen-4-yl)methyl]-5,7-dimethyl-2-ethylimidazo[1,2-b]pyridazine;
(12) 3-[(2'-Carboxybiphen-4-yl)methyl]-2-cyclopropyl-5,7-dimethylimidazo[1,2-b]pyridazine;
(13) 3-[(2'-Carboxybiphen-4-yl)methyl]-5-ethyl-7-methyl-2-propylimidazo[1,2-]pyridazine;
(14) 3-[(2'-Carboxybiphen-4-yl)methyl]-2,5-diethyl-7-methylimidazo[1,2-b]pyridazine;
(15) 3-[(2'-Carboxybiphen-4-yl)methyl]-2-ethyl-7-methyl-5-methylaminoimidazo[1,2-b]pyridazine;
(16) 5-Amino-3-[(2'-carboxybiphen-4-yl)methyl]-7-methyl-2-ethylimidazo[1,2-b]pyridazine;
(17) 3-[(2'-Carboxybiphen-4-yl)methyl]-2-ethyl-5-methylamino-7-trifluoromethylimidazo[1,2-b]pyridazine;
(18) 3-[(2'-Carboxybiphen-4-yl)methyl]-2-ethyl-5-methyl-7-methylaminoimidazo[1,2-b]pyridazine;
(19) 3-[(2'-Carboxybiphen-4-yl)methyl]-7-dimethylamino-2-ethyl-5-methylimidazo[1,2-b]pyridazine;
(20) 3-[(2'-Carboxybiphen-4-yl)methyl]-2-ethyl-5-methyl-7-phenylaminoimidazo[1,2-b]pyridazine;
(21) 3-[(2'-Carboxybiphen-4-yl)methyl]-2-ethyl-5-methyl-7-(morpholin-4-yl)imidazo[1,2-b]pyridazine;
(22) 3-[(2'-Carboxybiphen-4-yl)methyl]-2-ethyl-7-methyl-5-(morpholin-4-yl)imidazo[1,2-b]pyridazine;
(23) 3-[(2'-Carboxybiphen-4-yl)methyl]-2-ethyl-7-methoxy-5-methylimidazo[1,2-b]pyridazine;
(24) 3-[(2'-Carboxybiphen-4-yl)methyl]-2-ethyl-5-hydroxymethyl-7-methylimidazo[1,2-b]pyridazine;
(25) 5-Carboxy-3-[(2'-carboxybiphen-4-yl)methyl]-2-ethyl-7-methylimidazo[1,2-b]pyridazine;
(26) 5-Carbomethoxy-3-[(2'-carboxybiphen-4-yl)methyl]-2-ethyl-7-methylimidazo[1,2-b]pyridazine;
(27) 3-[(2'-Carboxybiphen-4-yl)methyl]-2-ethyl-7-methyl-5-phenylimidazo[1,2-b]pyridazine;
(28) 3-[(2'-Carboxybiphen-4-yl)methyl]-5-(2-chloro)phenyl-2-ethyl-7-methylimidazo[1,2-b]pyridazine;
(29) 3-[(2'-Carboxybiphen-4-yl)methyl]-5-(4-chloro)phenyl-2-ethyl-7-methylimidazo[1,2-b]pyridazine;
(30) 3-[(2'-Carboxybiphen-4-yl)methyl]-2-ethyl-7-methyl-5-(2-trifluoromethyl)phenylimidazo[1,2-b]pyridazine;
(31) 6-Amino-3-[(2'-carboxybiphen-4-yl)methyl]-5,7-dimethyl-2-ethylimidazo[1,2-b]pyridazine;
(32) 3-[(2'-Carboxybiphen-4-yl)methyl]-5,7-dimethyl-2-ethyl-6-ethylaminoimidazo[1,2-b]pyridazine;
(33) 3-[(2'-Carboxybiphen-4-yl)methyl]-5,7-dimethyl-2-ethyl-6-fluoroimidazo[1,2-b]pyridazine;
(34) 3-[(2'-Carboxybiphen-4-yl)methyl]-5,7-dimethyl-2-(2,2,2-trifluoroethylimidazo[1,2-b]pyridazine;
(35) 3-[(2'-Carboxybiphen-4-yl)methyl]-5,7-dimethyl-2-(pentafluoroethylimidazo[1,2-b]pyridazine;
(36) 3-[(2'-Carboxybiphen-4-yl)methyl]-5,7-dimethyl-2-(2,2,2-trifluoroethylimidazo[1,2-b]pyridazine;
(37) 3-[(2'-Carboxybiphen-4-yl)methyl]-5,7-dimethyl-2-(4,4,4-trifluorobutylimidazo[1,2-b]pyridazine;
(38) 3-[(2'-Carboxybiphen-4-yl)methyl]-5,7-dimethyl-2-(2,2-difluoropropylimidazo[1,2-b]pyridazine;
(39) 3-[(2'-Carboxybiphen-4-yl)methyl]-5,7-dimethyl-2-trans-2-butenylimidazo[1,2-b]pyridazine;
(40) 3-[(2'-Carboxybiphen-4-yl)methyl]-5,7-dimethyl-2-trans-1-propenylimidazo[1,2-b]pyridazine;
(41) 2-Allyl-3-[(2'-carboxybiphen-4-yl)methyl]-5,7-dimethylimidazo[1,2-b]pyridazine;
(42) 3-[(2'-Carboxybiphen-4-yl)methyl]-5,7-dimethyl-2-(2-propynyl)imidazo[1,2-b]pyridazine;
(43) 2-(2-Butynyl)-3-[(2'-carboxybiphen-4-yl)methyl]-5,7-dimethylimidazo[1,2-b]pyridazine;
(44) 3-[(2'-Carboxybiphen-4-yl)methyl]-5,7-dimethyl-2-(4,4,4-trifluoro-2-butynyl)imidazo[1,2-b]pyridazine;
(45) 3-[(2'-Carboxybiphen-4-yl)methyl]-5,7-dimethyl-2-(2,2,2-trifluoroethoxy)imidazo[1,2-b]pyridazine;
(46) 2-Butyl-3-[(2'-(tetrazol-5-yl)biphen-4-yl)methyl]imidazo[1,2-b]pyridazine;
(47) 2-Propyl-3-[(2'-(tetrazol-5-yl)biphen-4-yl)methyl]imidazo[1,2-b]pyridazine;
(48) 2-Ethyl-3-[(2'-(tetrazol-5-yl)biphen-4-yl)methyl]imidazo[1,2-b]pyridazine;
(49) 2-Isopropyl-3-[(2'-(tetrazol-5-yl)biphen-4-yl)methyl]imidazo[1,2-b]pyridazine;
(50) 2-Cyclopropyl-3-[(2'-(tetrazol-5-yl)biphen-4-yl)methyl]imidazo[1,2-b]pyridazine;
(51) 7-Methyl-2-propyl-3-[(2'-(tetrazol-5-yl)biphen-4-yl)methyl]imidazo[1,2-b]pyridazine;
(52) 7-Ethyl-2-propyl-3-[(2'-(tetrazol-5-yl)biphen-4-yl)methyl]imidazo[1,2-b]pyridazine;
(53) 2-Ethyl-7-methyl-3-[(2'-(tetrazol-5-yl)biphen-4-yl)methyl]imidazo[1,2-b]pyridazine;
(54) 2,7-Diethyl-3-[(2'-(tetrazol-5-yl)biphen-4-yl)methyl]imidazo[1,2-b]pyridazine;

(55) 5,7-Dimethyl-2-propyl-3-[(2'-(tetrazol-5-yl)biphen-4-yl)methyl]imidazo[1,2-b]pyridazine;
(56) 5,7-Dimethyl-2-ethyl-3-[(2'-(tetrazol-5-yl)biphen-4-yl)methyl]imidazo[1,2-b]pyridazine;
(57) 2-Cyclopropyl-5,7-dimethyl-3-[(2'-(tetrazol-5-yl)biphen-4-yl)methyl]imidazo[1,2-b]pyridazine;
(58) 5-Ethyl-7-methyl-2-propyl-3-[(2'-(tetrazol-5-yl)biphen-4-yl)methyl]imidazo[1,2-b]pyridazine;
(59) 2,5-Diethyl-7-methyl-3-[(2'-(tetrazol-5-yl)biphen-4-yl)methyl]imidazo[1,2-b]pyridazine;
(60) 2-Ethyl-7-methyl-5-methylamino-3-[(2'-(tetrazol-5-yl)biphen-4-yl)methyl]imidazo[1,2-b]pyridazine;
(61) 5-Amino-7-methyl-2-ethyl-3-[(2'-(tetrazol-5-yl)biphen-4-yl)methyl]imidazo[1,2-b]pyridazine;
(62) 2-Ethyl-5-methylamino-7-trifluoromethyl-3-[(2'-(tetrazol-5-yl)biphen-4-yl)methyl]imidazo[1,2-b]pyridazine;
(63) 2-Ethyl-5-methyl-7-methylamino-3-[(2'-(tetrazol-5-yl)biphen-4-yl)methyl]imidazo[1,2-b]pyridazine;
(64) 7-Dimethylamino-2-ethyl-5-methyl-3-[(2'-(tetrazol-5-yl)biphen-4-yl)methyl]imidazo[1,2-b]pyridazine;
(65) 2-Ethyl-5-methyl-7-phenylamino-3-[(2'-(tetrazol-5-yl)biphen-4-yl)methyl]imidazo[1,2-b]pyridazine;
(66) 2-Ethyl-5-methyl-7-(morpholin-4-yl)-3-[(2'-(tetrazol-5-yl)biphen-4-yl)methyl]imidazo[1,2-b]pyridazine;
(67) 2-Ethyl-7-methyl-5-(morpholin-4-yl)-3-[(2'-(tetrazol-5-yl)biphen-4-yl)methyl]imidazo[1,2-b]pyridazine;
(68) 2-Ethyl-7-methoxy-5-methyl-3-[(2'-(tetrazol-5-yl)biphen-4-yl)methyl]imidazo[1,2-b]pyridazine;
(69) 2-Ethyl-5-hydroxymethyl-7-methyl-3-[(2'-(tetrazol-5-yl)biphen-4-yl)methyl]imidazo[1,2-b]pyridazine;
(70) 5-Carboxy-2-ethyl-7-methyl-3-[(2'-(tetrazol-5-yl)biphen-4-yl)methyl]imidazo[1,2-b]pyridazine;
(71) 5-Carbomethoxy-2-ethyl-7-methyl-3-[(2'-(tetrazol-5-yl)biphen-4-yl)methyl]imidazo[1,2-b]pyridazine;
(72) 2-Ethyl-7-methyl-5-phenyl-3-[(2'-(tetrazol-5-yl)biphen-4-yl)methyl]imidazo[1,2-b]pyridazine;
(73) 5-(2-Chloro)phenyl-2-ethyl-7-methyl-3-[(2'-(tetrazol-5-yl)biphen-4-yl)methyl]imidazo[1,2-b]pyridazine;
(74) 5-(4-Chloro)phenyl-2-ethyl-7-methyl-3-[(2'-(tetrazol-5-yl)biphen-4-yl)methyl]imidazo[1,2-b]pyridazine;
(75) 2-Ethyl-7-methyl-5-(2-trifluoromethyl)phenyl-3-[(2'-(tetrazol-5-yl)biphen-4-yl)methyl]imidazo[1,2-b]pyridazine;
(76) 6-Amino-5,7-dimethyl-2-ethyl-3-[(2'-(tetrazol-5-yl)biphen-4-yl)methyl]imidazo[1,2-b]pyridazine;
(77) 5,7-Dimethyl-2-ethyl-6-ethylamino-3-[(2'-(tetrazol-5-yl)biphen-4-yl)methyl]imidazo[1,2-b]pyridazine;
(78) 5,7-Dimethyl-2-ethyl-6-fluoro-3-[(2'-(tetrazol-5-yl)biphen-4-yl)methyl]imidazo[1,2-b]pyridazine;
(79) 5,7-Dimethyl-3-[(2'-(tetrazol-5-yl)biphen-4-yl)methyl]-2-(2,2,2-trifluoroethyl)imidazo[1,2-b]pyridazine;
(80) 5,7-Dimethyl-2-(pentafluoroethyl)-3-[(2'-(tetrazol-5-yl)biphen-4-yl)methyl]imidazo[1,2-b]pyridazine;
(81) 5,7-Dimethyl-3-[(2'-(tetrazol-5-yl)biphen-4-yl)methyl]-2-(3,3,3-trifluoropropyl)imidazo[1,2-b]pyridazine;
(82) 5,7-Dimethyl-3-[(2'-(tetrazol-5-yl)biphen-4-yl)methyl]-2-(4,4,4-trifluorobutyl)imidazo[1,2-b]pyridazine;
(83) 5,7-Dimethyl-2-(2,2-difluoropropyl)-3-[(2'-(tetrazol-5-yl)biphen-4-yl)methyl]imidazo[1,2-b]pyridazine;
(84) 5,7-Dimethyl-2-trans-2-butenyl-3-[(2'-(tetrazol-5-yl)biphen-4-yl)methyl]imidazo[1,2-b]pyridazine;
(85) 5,7-Dimethyl-3-[(2'-(tetrazol-5-yl)biphen-4-yl)methyl]-2-trans-1-propenylimidazo[1,2-b]pyridazine;
(86) 2-Allyl-5,7-dimethyl-3-[(2'-(tetrazol-5-yl)biphen-4-yl)methyl]imidazo[1,2-b]pyridazine;
(87) 5,7-Dimethyl-2-(2-propynyl)-3-[(2'-(tetrazol-5-yl)biphen-4-yl)methyl]imidazo[1,2-b]pyridazine;
(88) 2-(2-Butynyl)-5,7-dimethyl-3-[(2'-(tetrazol-5-yl)biphen-4-yl)methyl]imidazo[1,2-b]pyridazine;
(89) 5,7-Dimethyl-3-[(2'-(tetrazol-5-yl)biphen-4-yl)methyl]-2-(4,4,4-trifluoro-2-butynyl)imidazo[1,2-b]pyridazine;
(90) 5,7-Dimethyl-3-[(2'-(tetrazol-5-yl)biphen-4-yl)methyl]-2-(2,2,2-trifluoroethoxy)imidazo[1,2-b]pyridazine;
(91) 5,7-Dimethyl-2-ethyl-3-[(2'-(N-((phenylsulfonyl)carboxamido)biphen-4-yl)methyl]imidazo[1,2-b]pyridazine;
(92) 5,7-Dimethyl-2-ethyl-3-[(2'-(N-((methylsulfonyl)carboxamido)biphen-4-yl)methyl]imidazo[1,2-b]pyridazine;
(93) 5,7-Dimethyl-2-ethyl-3-[(2'-(N-((trifluoromethylsulfonyl)carboxamido)biphen-4-yl)methyl]imidazo[1,2-b]pyridazine;
(94) 3-[(2'-(N-((2-Aminoethyl)sulfonyl)carboxamido)biphen-4-yl)methyl]-5,7-dimethyl-2-ethylimidazo[1,2-b]pyridazine;
(95) 5,7-Dimethyl-2-ethyl-3-[(2'-(N-((morpholin-4-yl)sulfonyl)carboxamido)biphen-4-yl)methyl]imidazo[1,2-b]pyridazine;
(96) 5,7-Dimethyl-[(2'-(N-(N,N-dimethylaminosulfonyl)carboxamido)biphen-4-yl)methyl]-2-ethyl-3-imidazo[1,2-b]pyridazine;
(97) 3-[(2'-(N-(Cyclopentylsulfonyl)carboxamido)biphen-4-yl)methyl]-5,7-dimethyl-2-ethylimidazo[1,2-b]pyridazine;
(98) 5,7-Dimethyl-2-ethyl-3-[(2'-(N-(pyrimidin-2-yl)-biphen-4-yl)methyl]imidazo[1,2-b]pyridazine;
(99) 5,7-Dimethyl-3-[(2'-(N-(4,6-dimethylpyrimidin-2-yl)sulfonamido)biphen-4-yl)methyl]-2-ethylimidazo[1,2-b]pyridazine;
(101) 5,7-Dimethyl-2-ethyl-3-[(2'-(N-(oxazol-2-yl)sulfonamido)biphen-4-yl)methyl]imidazo[1,2-b]pyridazine;
(102) 3-[(2'-(N-(Acetyl)sulfonamido)biphen-4-yl)methyl]-5,7-dimethyl-2-ethylimidazo[1,2-b]pyridazine;
(103) 3-[(2'-(N-(Benzoyl)sulfonamido)biphen-4-yl)methyl]-5,7-dimethyl-2-ethylimidazo[1,2-b]pyridazine;
(104) 5,7-Dimethyl-2-ethyl-3-[(2'-(N-(4-nitrobenzoyl)sulfonamido)biphen-4-yl)methyl]imidazo[1,2-b]pyridazine;
(105) 3-[(2'-(N-(4-Chlorobenzoyl)sulfonamido)biphen-4-yl)methyl]-5,7-dimethyl-2-ethylimidazo[1,2-b]pyridazine;
(106) 5,7-Dimethyl-2-ethyl-3-[(2'-(N-((morpholin-4-yl)carbonyl)sulfonamido)biphen-4-yl)methyl]imidazo[1,2-b]pyridazine;
(107) 5,7-Dimethyl-2-ethyl-3-[(2'-(N-((piperazin-1-yl)carbonyl)sulfonamido)biphen-4-yl)methyl]imidazo[1,2-b]pyridazine;
(108) 5,7-Dimethyl-2-ethyl-3-[(2'-((N-(trifluoromethyl)carbonyl)sulfonamido)biphen-4-yl)methyl]imidazo[1,2-b]pyridazine;

(109) 3 -[(2'-(N-((2-Carboxyethyl)carbonyl)sulfonamido)biphen-4 -yl)methyl]-5,7-dimethyl-2 -ethylimidazo[1,2 -b]pyridazine;

(110) 5,7-Dimethyl-3 -[(2'-((N-(2-ethoxyethyl)carbonyl)sulfonamido)biphen-4 -yl)methyl]-2 -ethylimiadazo[1,2 -b]pyridazine;

(111) 5,7-Dimethyl-2 -ethyl-3 -[(2'-(N-((phenylsulfonyl)carboxamido)methylbiphen-4 -yl)methyl]imidazo[1,2 -b]pyridazine;

(112) 5,7-Dimethyl-3 -[(2'-(N-(4,6-dimethylpyrimidin-2 -yl)sulfonamido)methylbiphen-4 -yl)methyl]-2 -ethylimidazo[1,2 -b]pyridazine;

(113) 5-Carboethoxy-2 -cyclopropyl-7-methyl-3-[(2'-(tetrazol-5-yl)biphen-4 -yl)methyl]imidazo[1,2 -b]pyridazine;

(114) 5-Carboethoxy-7-methyl-2 -propyl-3 -[(2'-(tetrazol-5-yl)biphen-4 -yl)methyl]imidazo[1,2-b]pyridazine;

(115) 3 -[(2'-(N-(Benzoyl)sulfonamido)biphen-4-yl)methyl]-5-carboethoxy-2 -cyclopropyl-7-methylimidazo[1,2 -b]pyridazine; and, (116) 3 -[(2'-(N-(Benzoyl)sulfonamido)biphen-4-yl)methyl]-5-carboethoxy-7-methyl-2 -propylimidazo[1,2 -b]pyridazine;

(117) 2 -Cyclopropyl-5,7-dimethyl-3 -[(2'-(N-(butoxycarbonyl)sulfonamido)biphen-4 -yl)methyl]imidazo[1,2-b]pyridazine;

(118) 2 -Cyclopropyl-5,7-dimethyl-3 -[(2'-(N-(butoxycarbonyl)sulfonamido)-5'-isobutylbiphen-4-yl)methyl]imidazo[1,2 -b]pyridazine;

(119) 2 -Cyclopropyl-5,7-dimethyl-3 -[(2'-(N-(butoxycarbonyl)sulfonamido)-5'-propylbiphen-4-yl)methyl]imidazo[1,2 -b]pyridazine;

(120) 2 -Cyclopropyl-5,7-dimethyl-3 -[(2'-(N-(propoxycarbonyl)sulfonamido)-5'-isobutylbiphen-4-yl)methyl]imidazo[1,2 -b]pyridazine;

(121) 2 -Cyclopropyl-5,7-dimethyl-3 -[(2'-(N-(cyclopropanecarbonyl)sulfonamido)biphen-4 -yl)methyl]imidazo[1,2 -b]pyridazine;

(122) 2 -Cyclopropyl-5,7-dimethyl-3 -[(2'-(N-((R)-2,2 -dimethylcyclopropane-1-carbonyl)sulfonamido)biphen-4 -yl)methyl]imidazo[1,2 -b]pyridazine;

(123) 2 -Cyclopropyl-5,7-dimethyl-3 -[(2'-(N-((S)-2,2 -dimethylcyclopropane-1-carbonyl)sulfonamido)biphen-4 -yl)methyl]imidazo[1,2 -b]pyridazine;

(124) 2 -Cyclopropyl-5,7-dimethyl-3 -[(2'-(N-(cyano)sulfonamido)biphen-4 -yl)methyl]imidazo[1,2 -b]pyridazine;

(125) 2 -Cyclopropyl-5,7-dimethyl-3 -[(2'-(N-(2 -thiazolo)sulfonamido)biphen-4 -yl)methyl]imidazo[1,2-b]pyridazine;

(126) N,N,7-trimethyl-2 -cyclopropyl-3 -[(2'-(tetrazol-5-yl)biphen-4 -yl)methyl]imidazo[1,2 -b]pyridazine-5-carboxamide;

(127) N,N-diethyl-2 -cyclopropyl-7-methyl-3 -[(2'-(tetrazol-5-yl)biphen-4 -yl)methyl]imidazo[1,2 -b]pyridazine-5-carboxamide;

(128) N,N,7-trimethyl-2 -cyclopropyl-3 -[(2'-(N-(cyclopropanecarbonyl)sulfonamido)biphen-4 -yl)methyl]imidazo[1,2 -b]pyridazine-5-carboxamide;

(129) N,N,7-trimethyl-2 -cyclopropyl-3-[(2'-(N-((R)-2,2 -dimethylcyclopropane-1-carbonyl)sulfonamido)biphen-4 -yl)methyl]imidazo[1,2 -b]pyridazine-5-carboxamide;

(130) N,N,7-trimethyl-2 -cyclopropyl-3 -[(2'-(N-((S)-2,2 -dimethylcyclopropane-1-carbonyl)sulfonamido)biphen-4 -yl)methyl]imidazo[1,2 -b]pyridazine-5-carboxamide;

(131) N,N,7-trimethyl-2 -cyclopropyl-3 -[(2'-(N-(cyano)sulfonamido)biphen-4 -yl)methyl]imidazo[1,2 -b]pyridazine-5-carboxamide;

(132) N,N,7-trimethyl-2 -cyclopropyl-3 -[(2'-(N-(2 -thiazolo)sulfonamido)biphen-4 -yl)methyl]imidazo[1,2 -b]pyridazine-5-carboxamide.

7. The compound of structural formula:

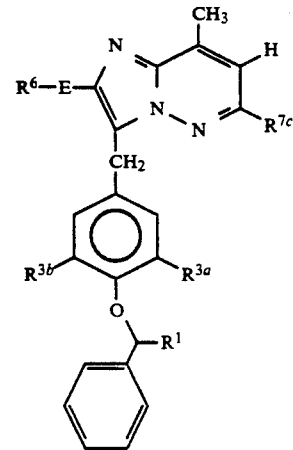

wherein the substituents are selected from the table below:

| $R^6$ | $R^{3b}$ | $R^{3a}$ | $R^{7c}$ | $R^1$ |
|---|---|---|---|---|
| cyPr | H | H | Me | —COOH |
| cyPr | H | H | Me | —COOMe |
| cyPr | H | H | Me | —CONHSO$_2$Ph |
| cyPr | H | H | Me | —CONHSO$_2$Me |
| cyPr | Cl | H | Me | —COOH |
| cyPr | Cl | H | Me | —COOMe |
| cyPr | Cl | H | Me | —CONHSO$_2$Ph |
| cyPr | Cl | H | Me | —CONHSO$_2$Me |
| cyPr | Cl | nPr | Me | —COOH |
| cyPr | Cl | nPr | Me | —COOMe |
| cyPr | Cl | nPr | Me | —CONHSO$_2$Ph |
| cyPr | Cl | nPr | Me | —CONHSO$_2$Me |
| cyPr | nPr | nPr | Me | —COOH |
| cyPr | nPr | nPr | Me | —COOMe |
| cyPr | nPr | nPr | Me | —CONHSO$_2$Ph |
| cyPr | nPr | nPr | Me | —CONHSO$_2$Me |
| cyPr | Cl | Cl | Me | —COOH |
| cyPr | Cl | Cl | Me | —COOMe |
| cyPr | Cl | Cl | Me | —CONHSO$_2$Ph |
| cyPr | Cl | Cl | Me | —CONHSO$_2$Me |
| Et | H | H | Me | —COOH |
| Et | H | H | Me | —COOMe |
| Et | H | H | Me | —CONHSO$_2$Ph |
| Et | H | H | Me | —CONHSO$_2$Me |
| Et | Cl | H | Me | —COOH |
| Et | Cl | H | Me | —COOMe |
| Et | Cl | H | Me | —CONHSO$_2$Ph |
| Et | Cl | H | Me | —CONHSO$_2$Me |
| Et | Cl | nPr | Me | —COOH |
| Et | Cl | nPr | Me | —COOMe |
| Et | Cl | nPr | Me | —CONHSO$_2$Ph |
| Et | Cl | nPr | Me | —CONHSO$_2$Me |
| Et | nPr | nPr | Me | —COOH |
| Et | nPr | nPr | Me | —COOMe |
| Et | nPr | nPr | Me | —CONHSO$_2$Ph |
| Et | nPr | nPr | Me | —CONHSO$_2$Me |
| Et | Cl | Cl | Me | —COOH |
| Et | Cl | Cl | Me | —COOMe |
| Et | Cl | Cl | Me | —CONHSO$_2$Ph |
| Et | Cl | Cl | Me | —CONHSO$_2$Me |
| Et | H | H | Me | —COOH |
| Et | H | H | Me | —COOMe |
| Et | H | H | Me | —CONHSO$_2$Ph |

| $R^6$ | $R^{3b}$ | $R^{3a}$ | $R^{7c}$ | $R^1$ |
|---|---|---|---|---|
| Et | H | H | Me | —CONHSO$_2$Me |
| Et | Cl | H | Me | —COOH |
| Et | Cl | H | Me | —COOMe |
| Et | Cl | H | Me | —CONHSO$_2$Ph |
| Et | Cl | H | Me | —CONHSO$_2$Me |
| Et | Cl | nPr | Me | —COOH |
| Et | Cl | nPr | Me | —COOMe |
| Et | Cl | nPr | Me | —CONHSO$_2$Ph |
| Et | Cl | nPr | Me | —CONHSO$_2$Me |
| Et | nPr | nPr | Me | —COOH |
| Et | nPr | nPr | Me | —COOMe |
| Et | nPr | nPr | Me | —CONHSO$_2$Ph |
| Et | nPr | nPr | Me | —CONHSO$_2$Me |
| Et | Cl | Cl | Me | —COOH |
| Et | Cl | Cl | Me | —COOMe |
| Et | Cl | Cl | Me | —CONHSO$_2$Ph |
| Et | Cl | Cl | Me | —CONHSO$_2$Me |
| nPr | H | H | Me | —COOH |
| nPr | H | H | Me | —COOMe |
| nPr | H | H | Me | —CONHSO$_2$Ph |
| nPr | H | H | Me | —CONHSO$_2$Me |
| nPr | Cl | H | Me | —COOH |
| nPr | Cl | H | Me | —COOMe |
| nPr | Cl | H | Me | —CONHSO$_2$Ph |
| nPr | Cl | H | Me | —CONHSO$_2$Me |
| nPr | Cl | nPr | Me | —COOH |
| nPr | Cl | nPr | Me | —COOMe |
| nPr | Cl | nPr | Me | —CONHSO$_2$Ph |
| nPr | Cl | nPr | Me | —CONHSO$_2$Me |
| nPr | nPr | nPr | Me | —COOH |
| nPr | nPr | nPr | Me | —COOMe |
| nPr | nPr | nPr | Me | —CONHSO$_2$Ph |
| nPr | nPr | nPr | Me | —CONHSO$_2$Me |
| nPr | Cl | Cl | Me | —COOH |
| nPr | Cl | Cl | Me | —COOMe |
| nPr | Cl | Cl | Me | —CONHSO$_2$Ph |
| nPr | Cl | Cl | Me | —CONHSO$_2$Me |
| nPr | H | H | Me | —COOH |
| nPr | H | H | Me | —COOMe |
| nPr | H | H | Me | —CONHSO$_2$Ph |
| nPr | H | H | Me | —CONHSO$_2$Me |
| nPr | Cl | H | Me | —COOH |
| nPr | Cl | H | Me | —COOMe |
| nPr | Cl | H | Me | —CONHSO$_2$Ph |
| nPr | Cl | H | Me | —CONHSO$_2$Me |
| nPr | Cl | nPr | Me | —COOH |
| nPr | Cl | nPr | Me | —COOMe |
| nPr | Cl | nPr | Me | —CONHSO$_2$Ph |
| nPr | Cl | nPr | Me | —CONHSO$_2$Me |
| nPr | nPr | nPr | Me | —COOH |
| nPr | nPr | nPr | Me | —COOMe |
| nPr | nPr | nPr | Me | —CONHSO$_2$Ph |
| nPr | nPr | nPr | Me | —CONHSO$_2$Me |
| nPr | Cl | Cl | Me | —COOH |
| nPr | Cl | Cl | Me | —COOMe |
| nPr | Cl | Cl | Me | —CONHSO$_2$Ph |
| nPr | Cl | Cl | Me | —CONHSO$_2$Me. | wherein:
cyPr represents cyclopropyl,
Et represents ethyl,
nPr represents n propyl,
Me represents methyl and
Ph represents phenyl.

8. A pharmaceutical composition useful in the treatment of hypertension which comprises a pharmaceutically acceptable carrier and a pharmaceutically effective amount of a compound of claim 1.

9. A method of treating hypertension which comprises administering to a patient in need of such treatment a therapeutically effective amount of a compound of claim 1.

10. An ophthalmological formulation for the treatment of ocular hypertension comprising an ophthalmologically acceptable carrier and an effective ocular antihypertensive amount of a compound of claim 1.

11. A method of treating ocular hypertension comprising topical ocular administration to a patient in need of such treatment of an effective ocular antihypertensive amount of a compound of claim 1.

* * * * *